US012161449B1

(12) United States Patent
Owsley et al.

(10) Patent No.: US 12,161,449 B1
(45) Date of Patent: Dec. 10, 2024

(54) SYSTEMS, APPARATUSES, AND METHODS FOR LOCATING BLOOD FLOW TURBULENCE IN THE CARDIOVASCULAR SYSTEM

(71) Applicant: PHONOFLOW MEDICAL, LLC, Gales Ferry, CT (US)

(72) Inventors: Norman Lee Owsley, Gales Ferry, CT (US); Ralph Walter Zaorski, Davenport, FL (US)

(73) Assignee: PHONOFLOW MEDICAL LLC, Gales Ferry, CT (US)

( * ) Notice: Subject to any disclaimer, the term of this patent is extended or adjusted under 35 U.S.C. 154(b) by 0 days.

(21) Appl. No.: 18/220,211

(22) Filed: Jul. 10, 2023

Related U.S. Application Data

(62) Division of application No. 17/467,118, filed on Sep. 3, 2021, now Pat. No. 11,730,381, which is a division
(Continued)

(51) Int. Cl.
*A61B 5/352* (2021.01)
*A61B 5/00* (2006.01)
(Continued)

(52) U.S. Cl.
CPC .............. *A61B 5/026* (2013.01); *A61B 5/352* (2021.01); *A61B 5/7257* (2013.01); *A61B 7/04* (2013.01);
(Continued)

(58) Field of Classification Search
None
See application file for complete search history.

(56) References Cited

U.S. PATENT DOCUMENTS 5,617,869 A 4/1997 Austin et al.
5,727,561 A 3/1998 Owsley
(Continued)

OTHER PUBLICATIONS

N. Owsley and A. Hull, "Beamformed Nearfield Imaging of a Simulated Coronary Artery Containing a Stenosis," IEEE Transactions on Medical Imaging, vol. 17, No. 6, Dec. 1998, pp. 900-909.
(Continued)

*Primary Examiner* — Ankit D Tejani
(74) *Attorney, Agent, or Firm* — PELOQUIN, PLLC; Mark S. Peloquin, Esq.

(57) ABSTRACT

An apparatus for locating a source of vibrational cardiac energy within a human, includes a data processing system configured to accept vibrational cardiac data collected by at least three transducers during a plurality of heart cycles. A computer readable medium containing executable computer program instructions which, when executed by the data processing system, cause the data processing system to perform steps that include, performing a time-to-frequency transformation on the vibrational cardiac data acquired within at least a portion of the heart cycles. The time-to-frequency transformation is applied to the vibrational cardiac data acquired synchronously from each transducer to obtain a plurality of complex frequency spectra. The steps include identifying a vernier band (VB) of frequency associated with a feature derived from the plurality of complex frequency spectra. The vibrational cardiac data are processed over the VB of frequency to obtain a first vibrational cardiac energy level for a first location within the human's chest. The first location corresponds to a source of the first vibrational cardiac energy level.

9 Claims, 42 Drawing Sheets

Related U.S. Application Data of application No. 16/055,086, filed on Aug. 4, 2018, now Pat. No. 11,134,858.

(51) Int. Cl.
  *A61B 5/026* (2006.01)
  *A61B 7/04* (2006.01)
  *A61B 5/364* (2021.01)
  *A61B 7/00* (2006.01)

(52) U.S. Cl.
  CPC ............. *A61B 5/364* (2021.01); *A61B 5/7282* (2013.01); *A61B 7/003* (2013.01); *A61B 2562/0204* (2013.01)

(56) References Cited

U.S. PATENT DOCUMENTS

| | | | |
|---|---|---|---|
| 6,056,703 | A | 5/2000 | Sandler et al. |
| 6,492,933 | B1 | 12/2002 | McEwan et al. |
| 6,776,776 | B2 | 8/2004 | Sandler et al. |
| 6,780,159 | B2 | 8/2004 | Sandler et al. |
| 8,419,651 | B2 | 4/2013 | Owsley et al. |
| 8,790,264 | B2 | 7/2014 | Sandler et al. |
| 8,961,427 | B2 | 2/2015 | Owsley et al. |
| 9,591,972 | B1 | 3/2017 | Owsley et al. |
| 2004/0249293 | A1 | 12/2004 | Sandler et al. |
| 2008/0119735 | A1 | 5/2008 | Lin et al. |
| 2011/0105932 | A1* | 5/2011 | Bauer .................. A61B 5/4818 600/528 |
| 2014/0187971 | A1* | 7/2014 | Owsley .................. A61B 7/00 600/479 |
| 2017/0188869 | A1* | 7/2017 | Kale ...................... A61B 5/335 |
| 2018/0085605 | A1 | 3/2018 | Maharbiz et al. |

OTHER PUBLICATIONS

N. Owsley, "Array Phonocardiography," Proceedings of the IEEE 2000 Adaptive Systems for Signal Processing, Communications and Control, Lake Louise, Alberta, Canada Oct. 2000, pp. 31-36.

T.O. Cheng, "Diastolic Murmer Caused by Coronary Artery Stenosis," Annals of Internal Medicine, 72:543-546, 1970.

J.L. Semmlow et al., "Coronary Artery Disease Correlates Between Diastolic Auditory Characteristics and Coronary Artery Stenosis," IEEE Trans, Biomedical Eng., vol. 37, No. 4, Apr. 1990, pp. 366-373.

J.L. Semmlow et al., "Utility of an advanced digital electronic stethoscope in the diagnosis of coronary artery disease compared with coronary computed tomographic angiography," American Jouranl of Cardiology, 2013, Elsevier, Inc., pp. 786-792.

Farzad Azimpour, MD, "Audible Coronary Artery Stenosis," pp. 515-521, The American Journal of Medicie, vol. 129, No. 5, May 2016.

J.L. Thomas et al., "The clinical evaluation of the CADence device in the acoustic detection of coronary artery disease," Int J. Cardiovascular Imaging 34, 1841-1848 (2018).

Verberg, Transmission of Vibrations of the Heart to the Chestwall, Adv. cardiovasc. Physics., (Karger, Basel 1983), pp. 84-103, vol. 5 (Part III).

\* cited by examiner

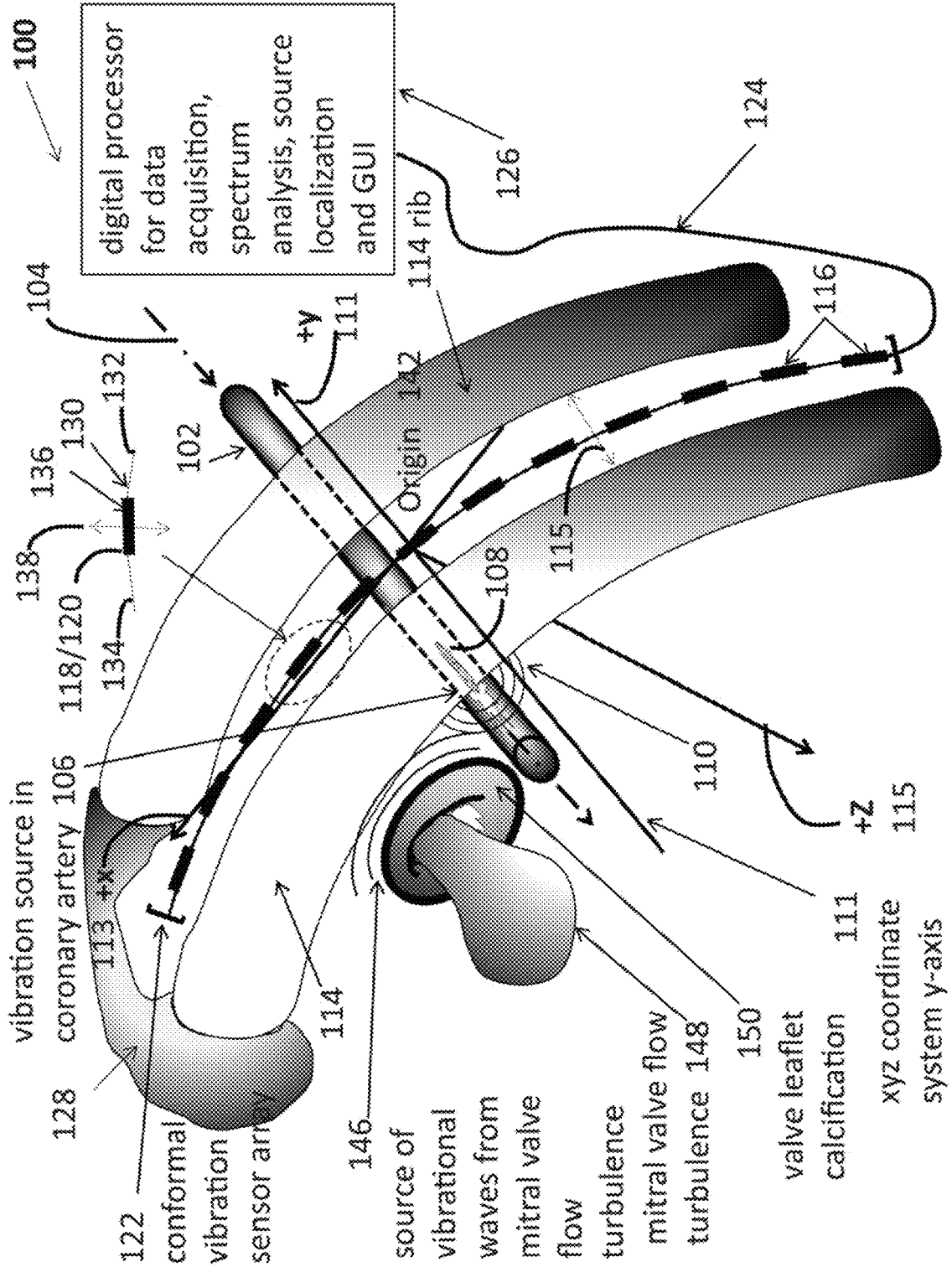

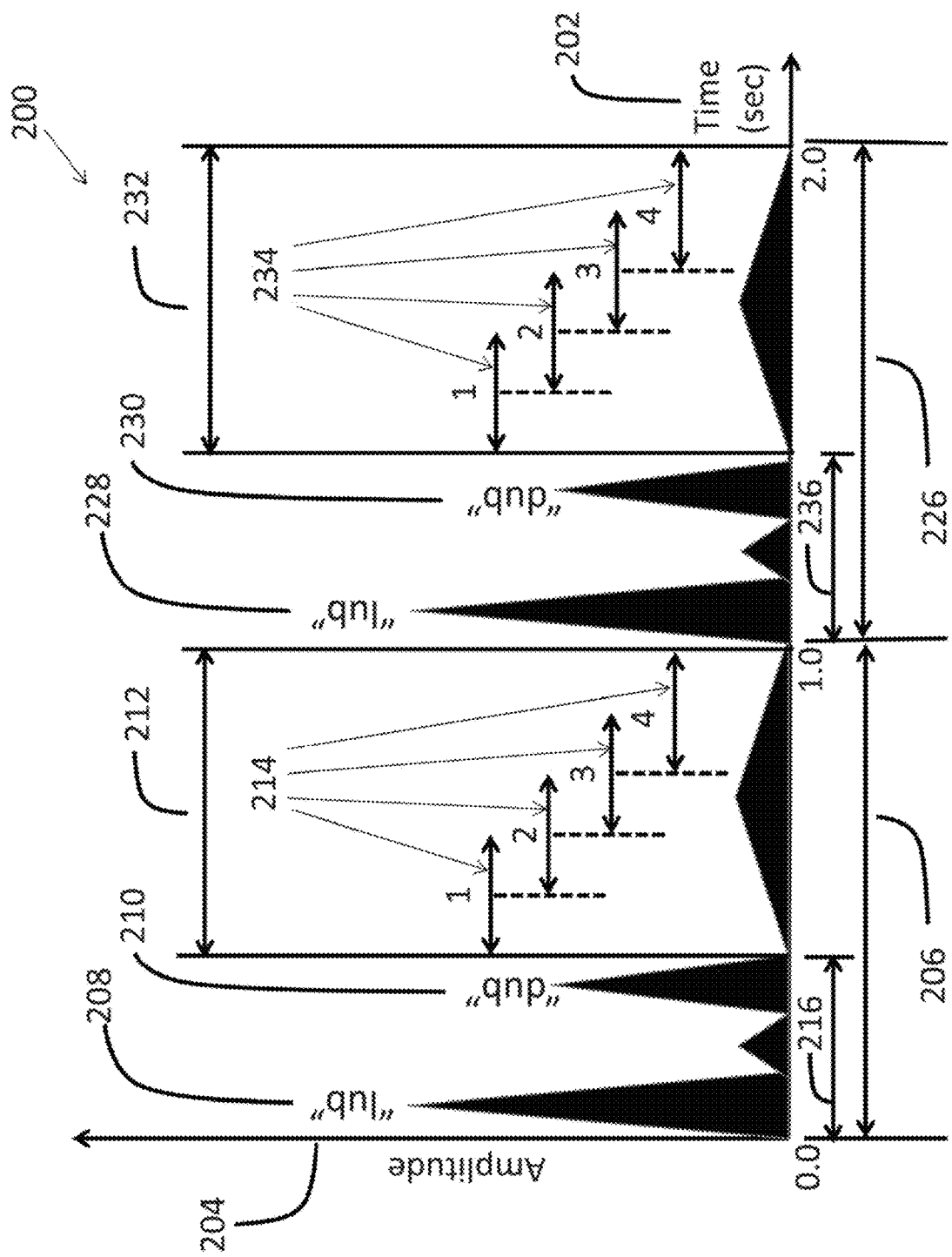
Figure 2 Heart cycle definitions

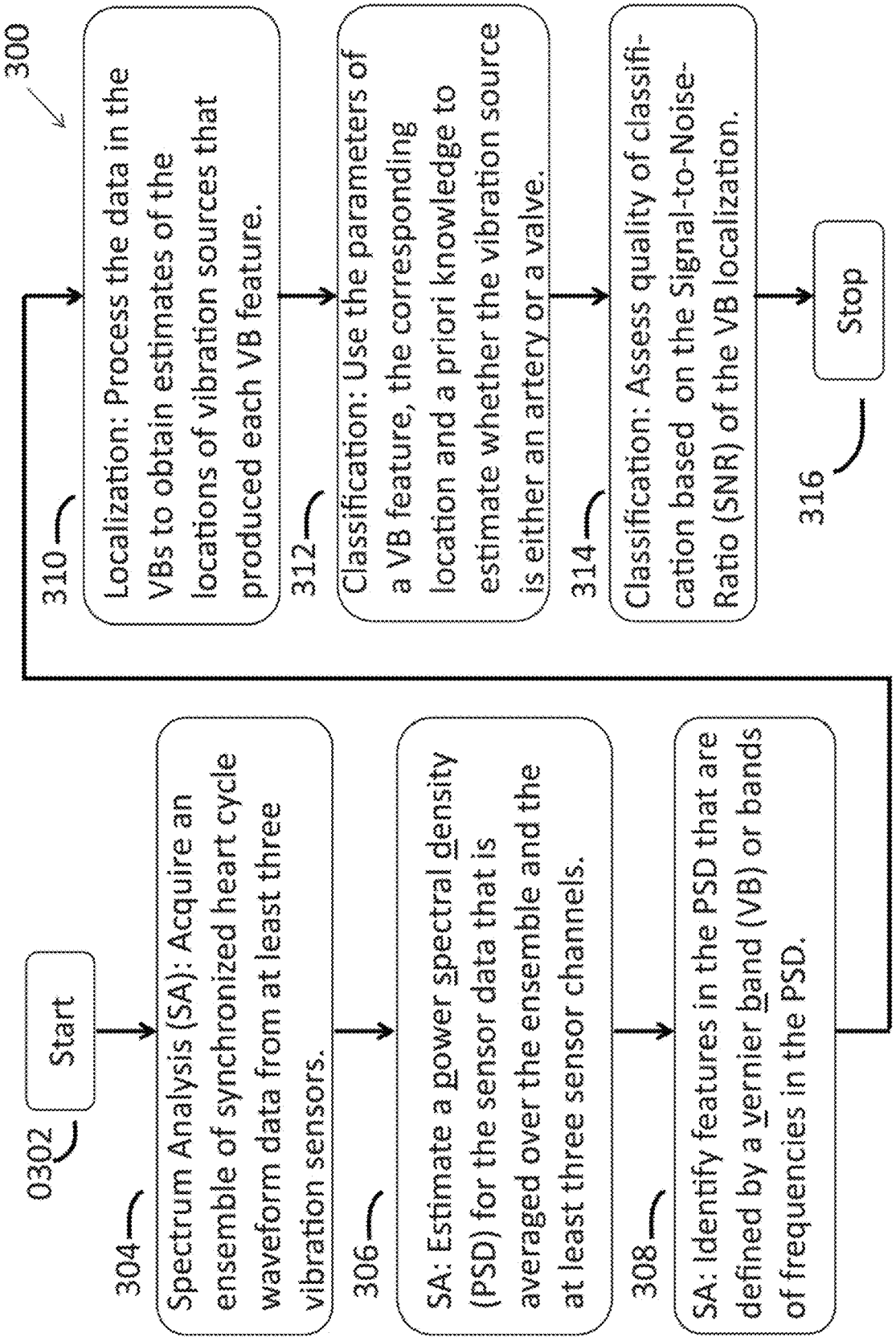
Figure 3    Post (spectrum) Analysis Localization (PAL)

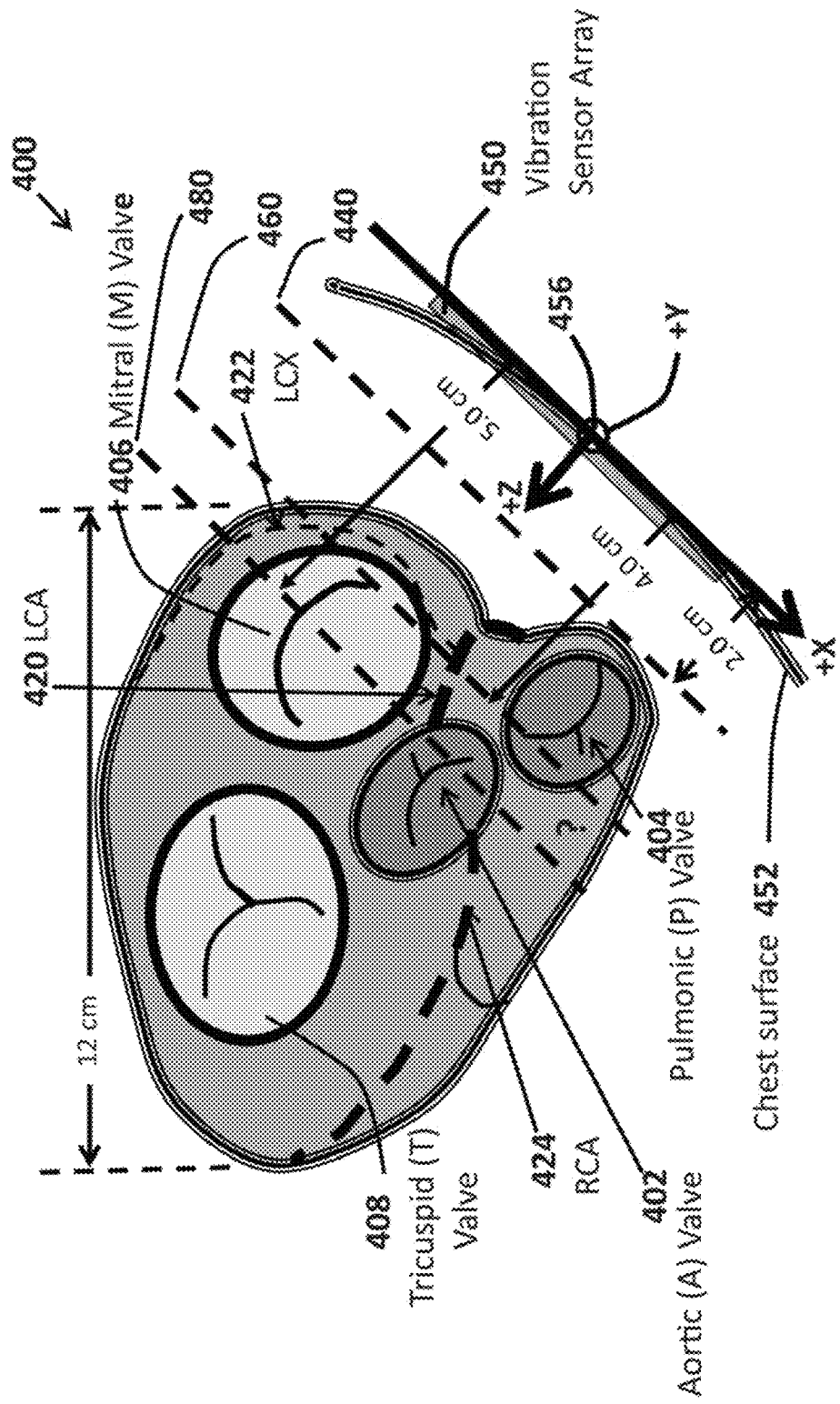
Figure 4 Locations of vibration sources and an array of vibration sensors

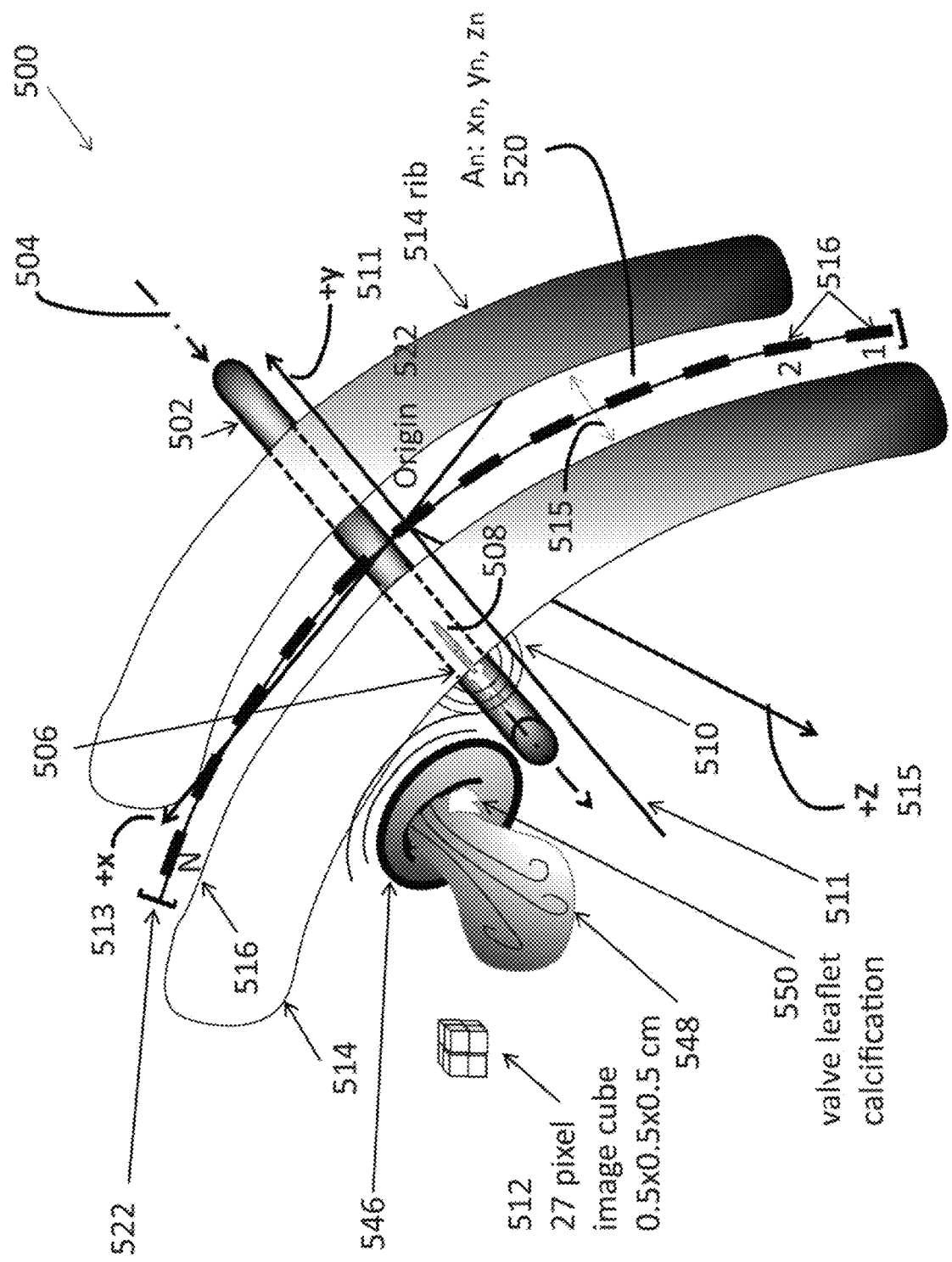
Figure 5 Diagram of a conformal array of chest vibration sensors

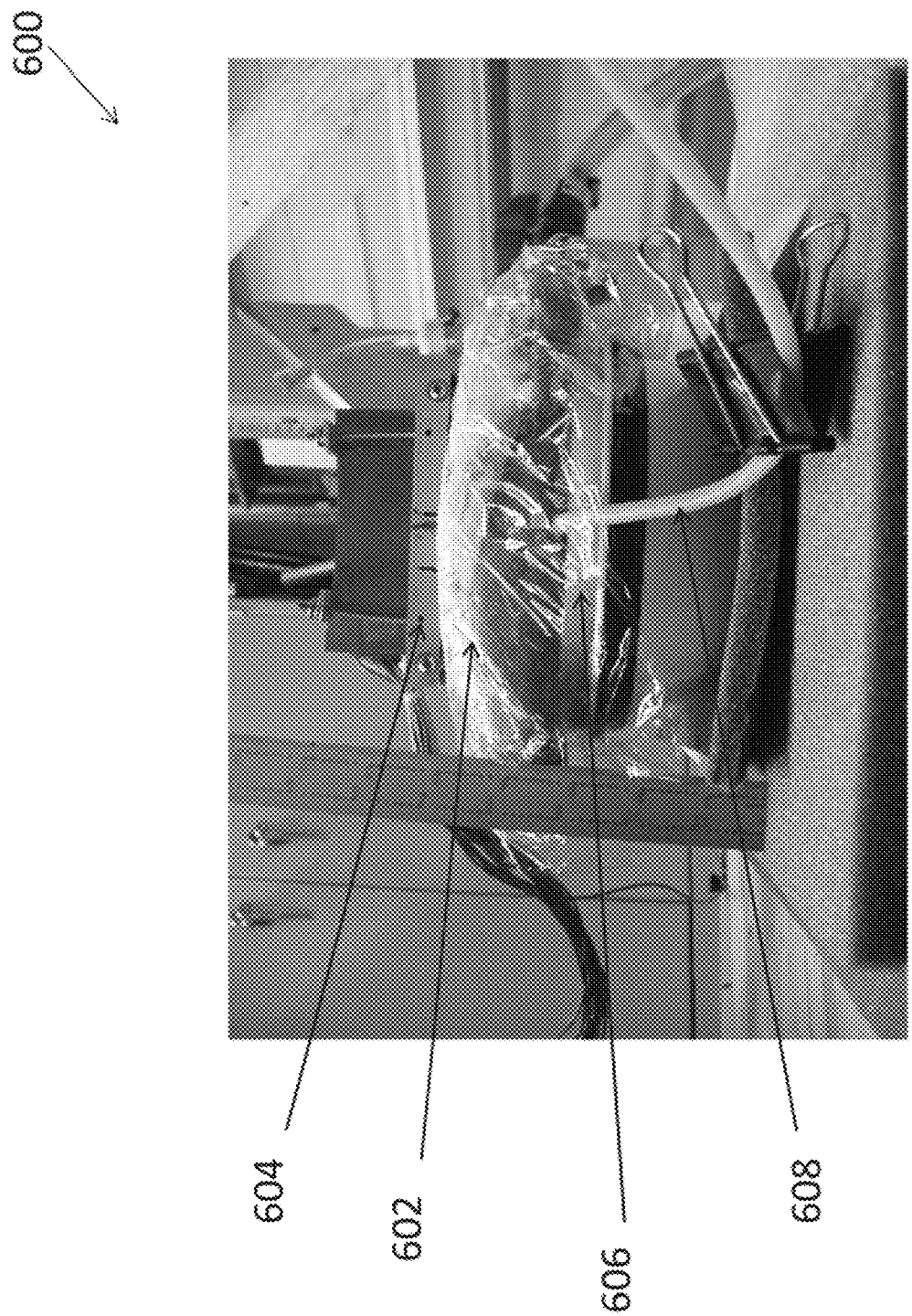
Figure 6 Tissue wave speed measurement apparatus

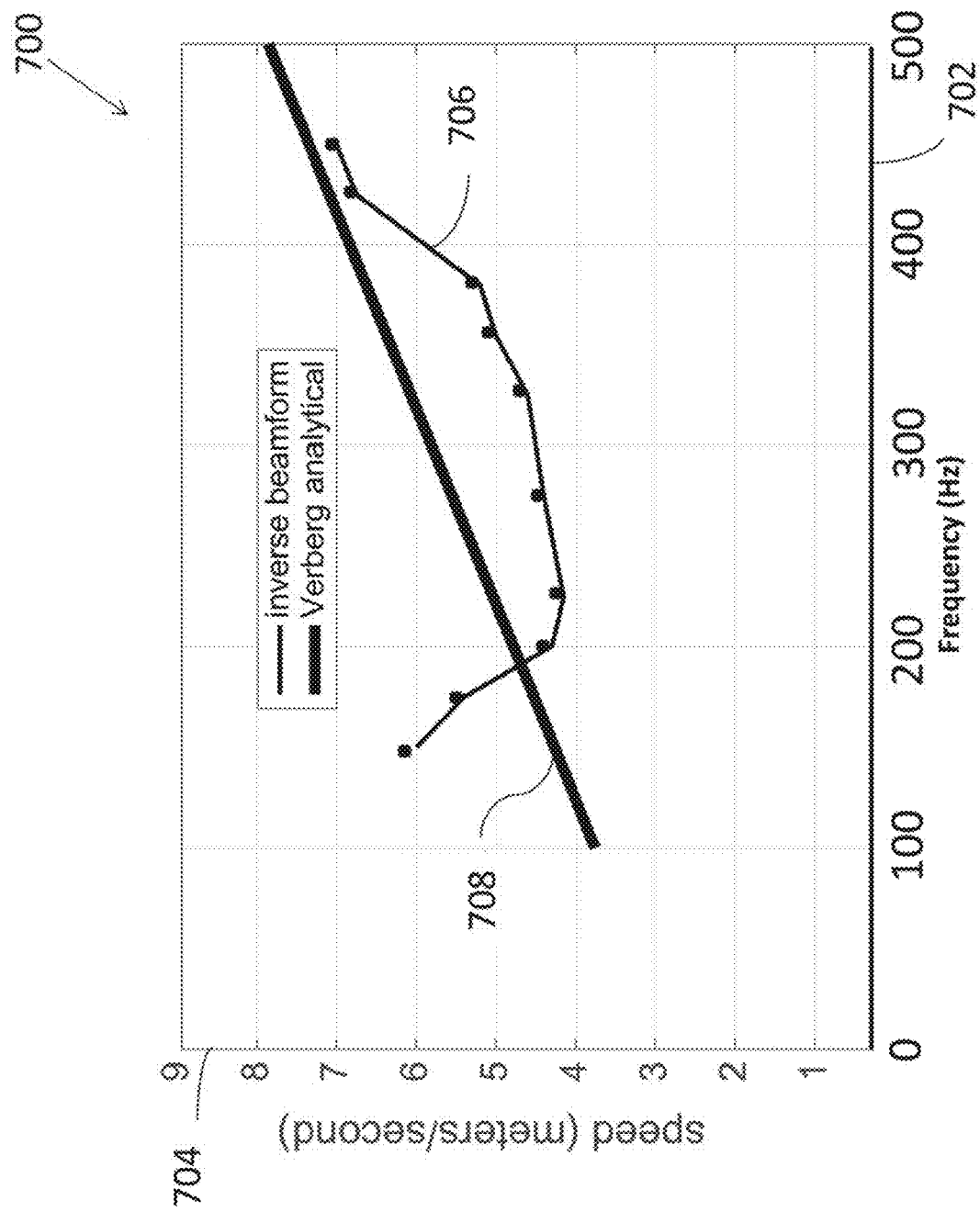
Figure 7 Wave speed dispersion curve in porcine tissue

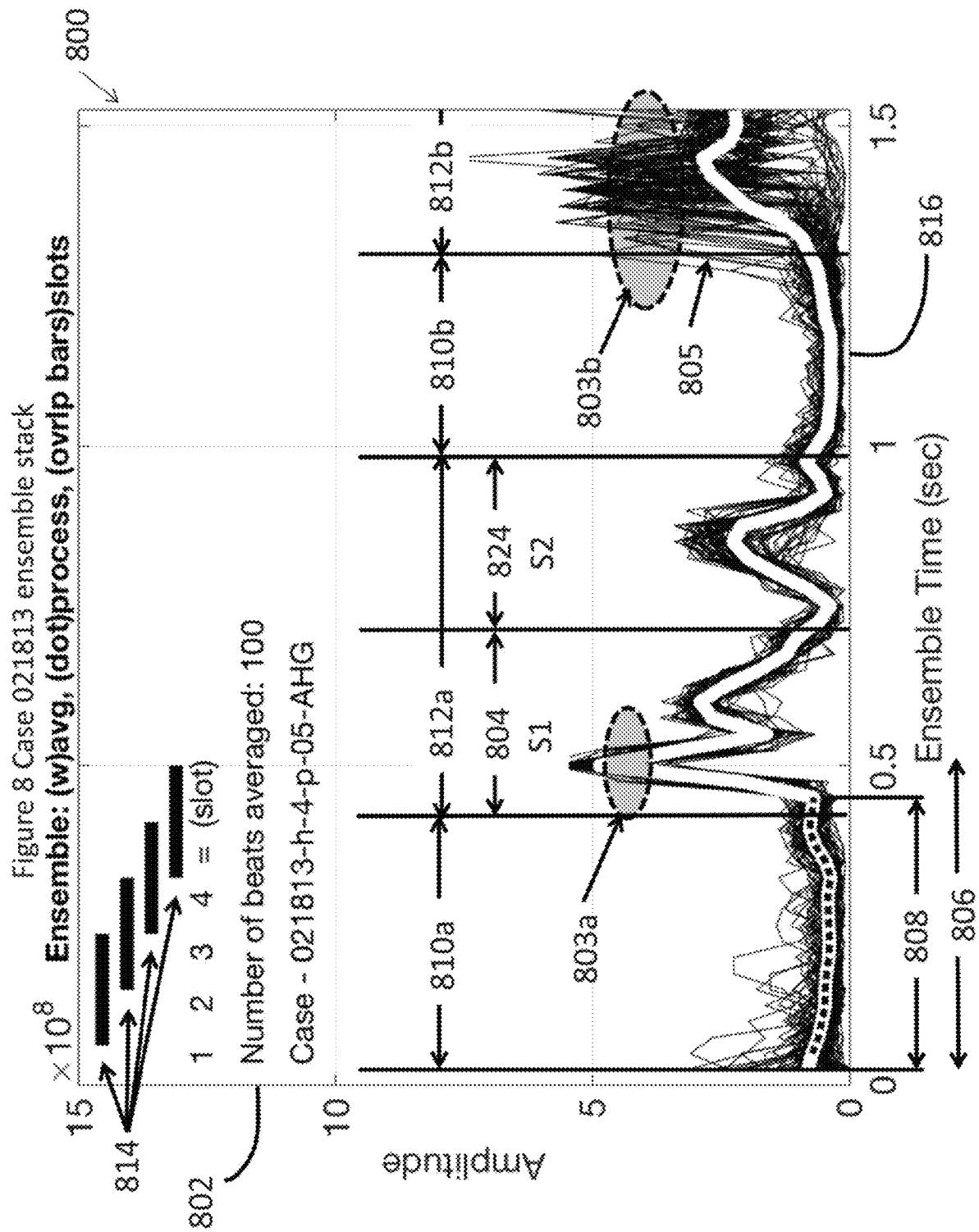

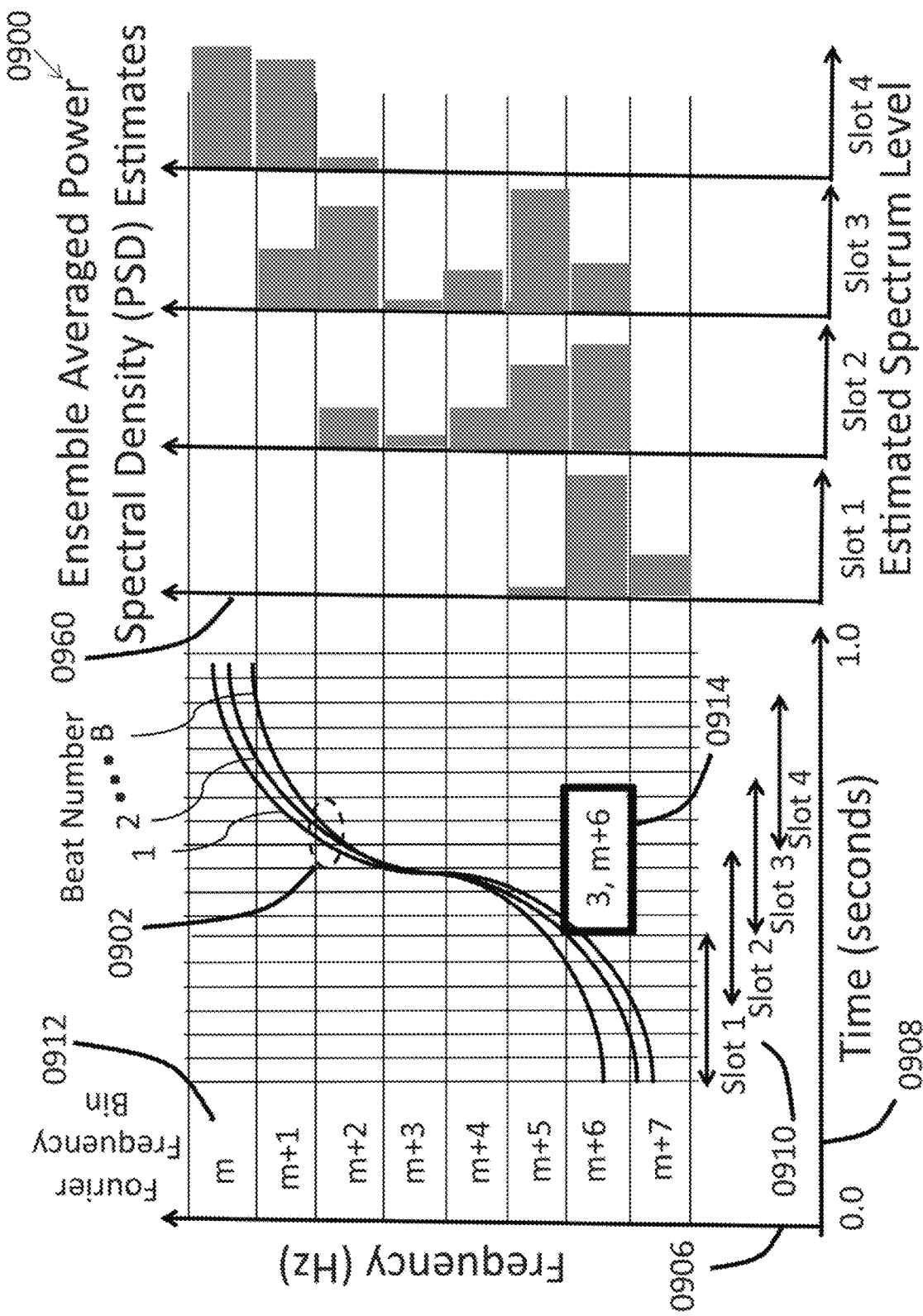

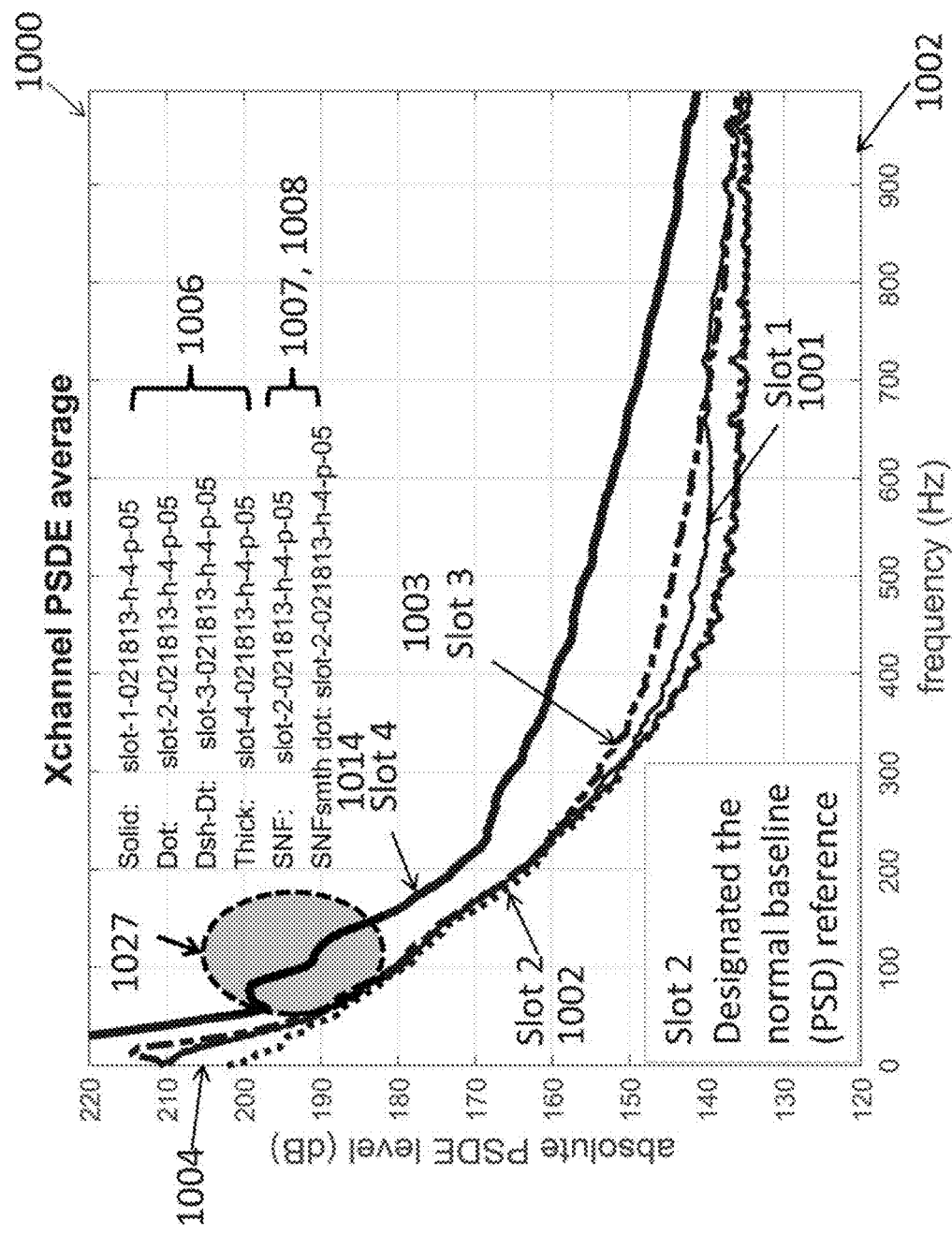
Figure 10 Case 021813 "normal" baseline

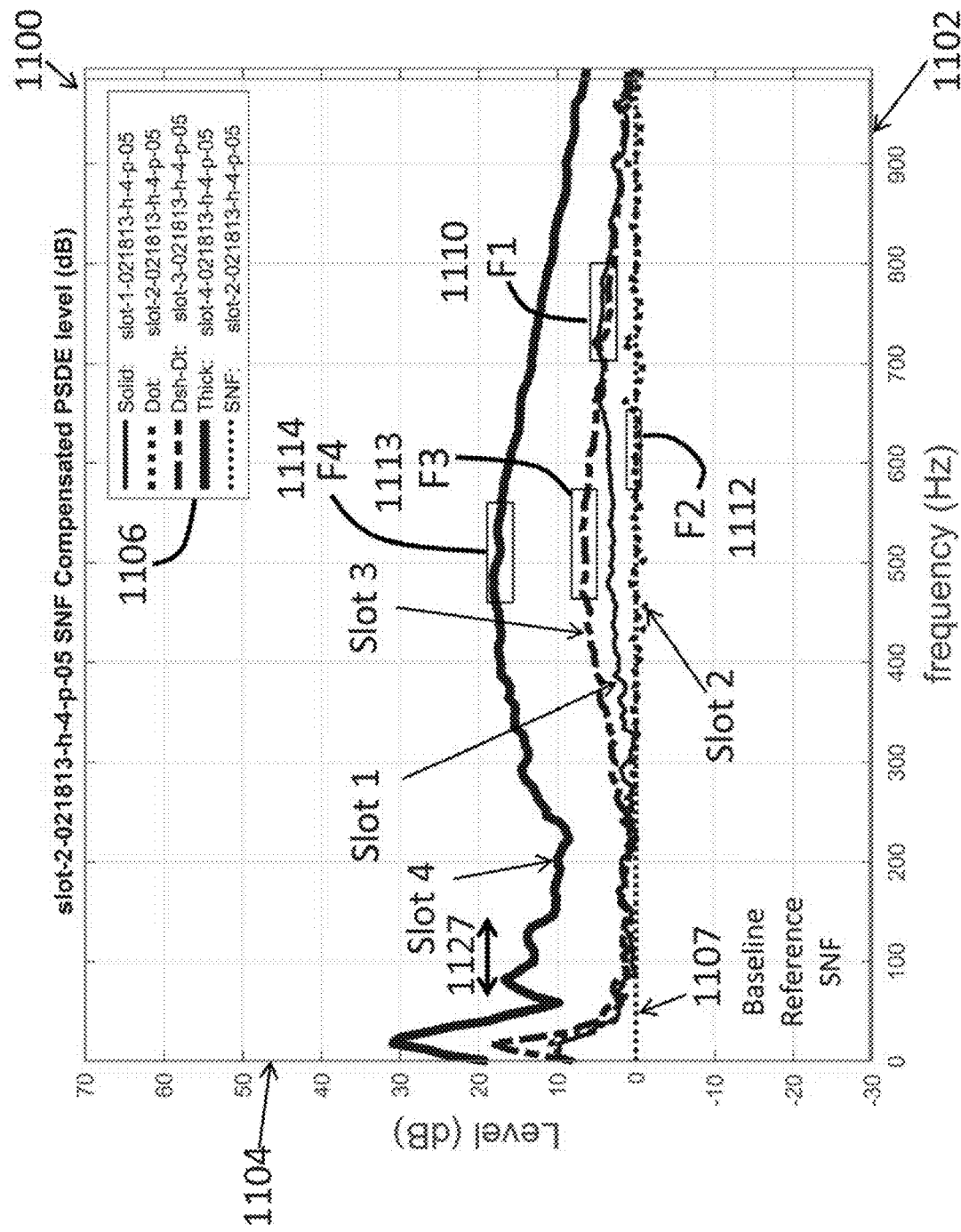
Figure 11 Case 021813 referenced to "Baseline"

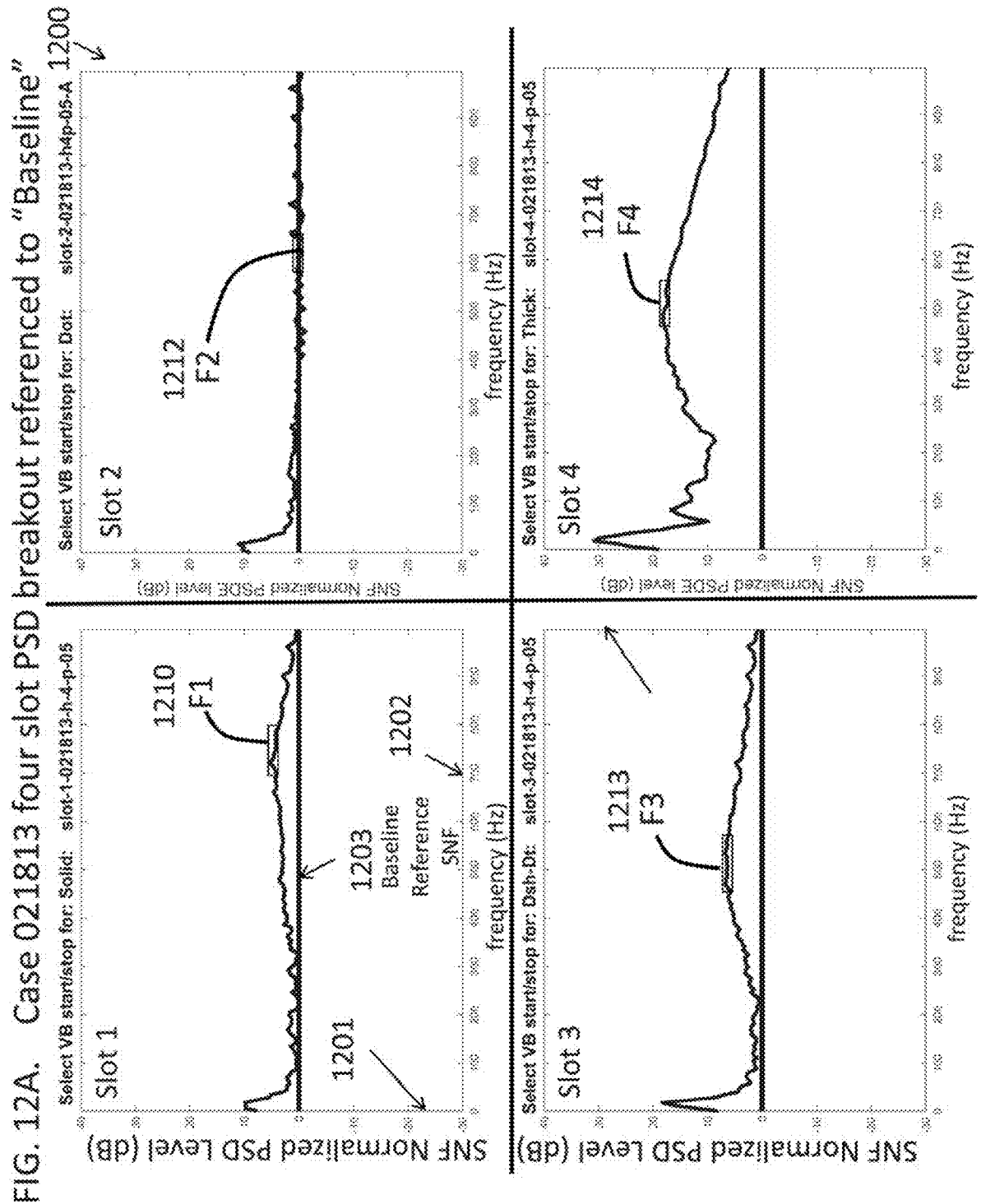
FIG. 12A. Case 021813 four slot PSD breakout referenced to "Baseline"

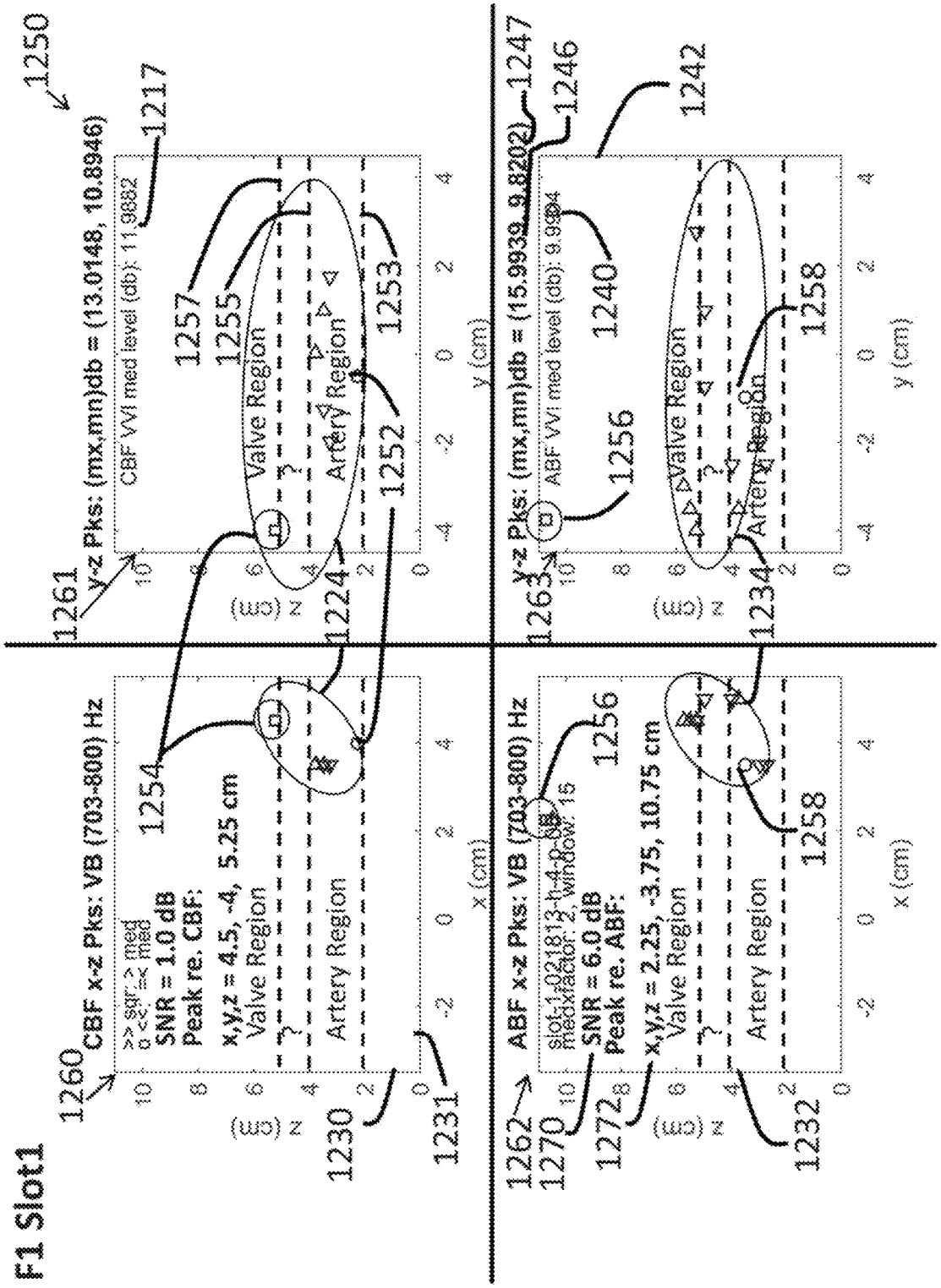
Figure 12B. Case 021813 Diastolic baseline normal VVI localization F1 Slot1

Figure 13  Case 021813 PAL results
| Case | Slot | Feature | VBand (Hz) | Beamform | SNR (dB.) | x, y, z (cm) |
|---|---|---|---|---|---|---|
| 21813_05 | 1 | F1 | 703 - 800 | CBF | 1.0 | 4.5, 3.75, 5.25 |
|  |  |  |  | ABF | 6.0 | 2.25, -3.75, 10.75 |
| 21813_05 | 2 | F2 | 566 - 655 | CBF | 0.8 | 2, -3.75, 3 |
|  |  |  |  | ABF | 0.6 | 2, -3.25, 3.5 |
| 21813_05 | 3 | F3 | 460 - 558 | CBF | < 0 | -3.5, -4.5, 2 |
|  |  |  |  | ABF | 0.1 | 1, -3.5, 5.75 |
| 21813_05 | 4 | F4 | 460 - 563 | CBF | < 0 | -3.5, -4.5, 2 |
|  |  |  |  | ABF | 2.3 | 1.75, -1, 2.5 |
Table I: Summary of PAL results for Case 021813

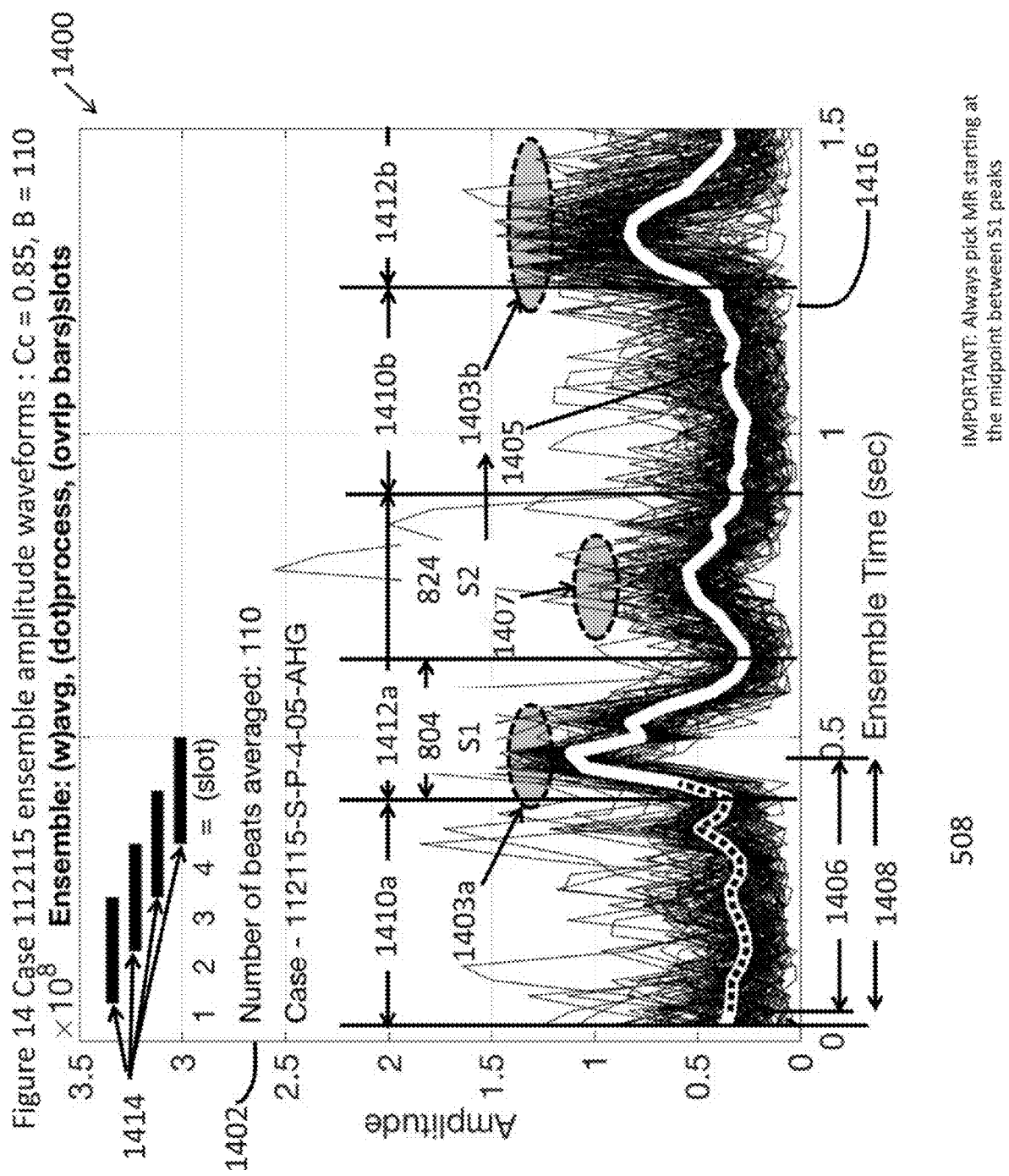

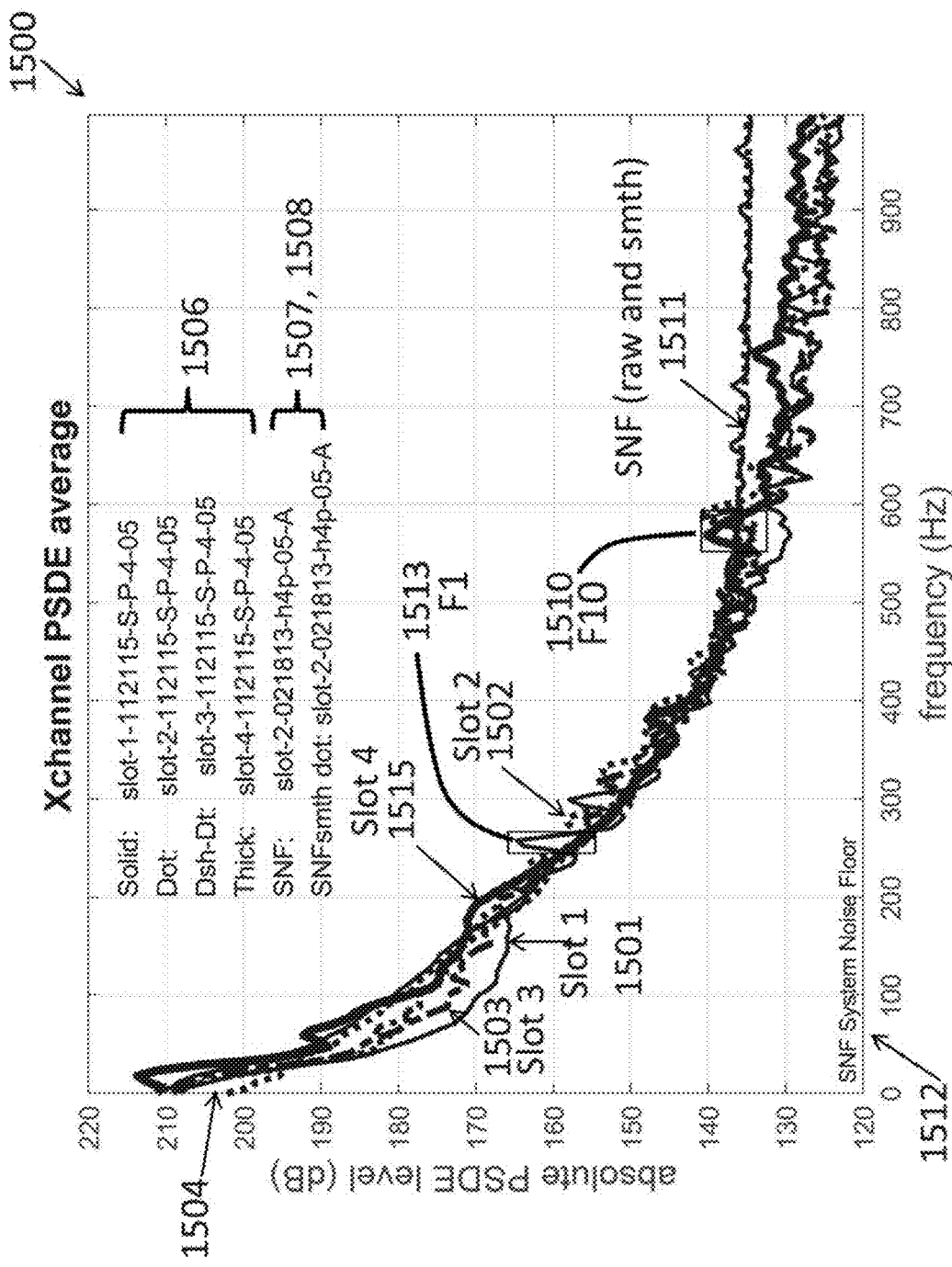
Figure 15A. Case 112115 Power spectrum density (PSD) absolute level: Cc = 0.85, B = 125

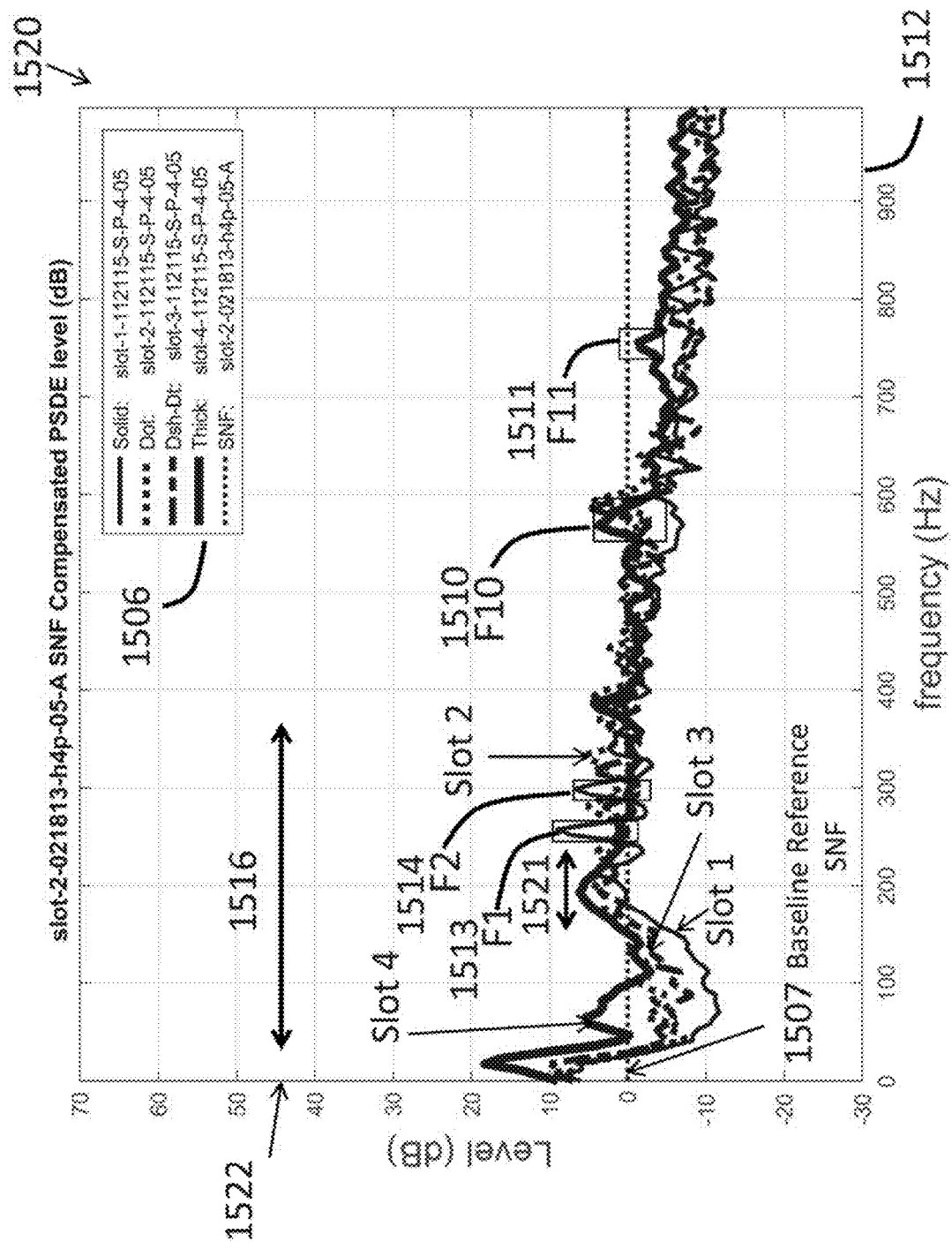
Figure 15B. Case 112115 Normalized Diastolic PSD(E)s: Confirm

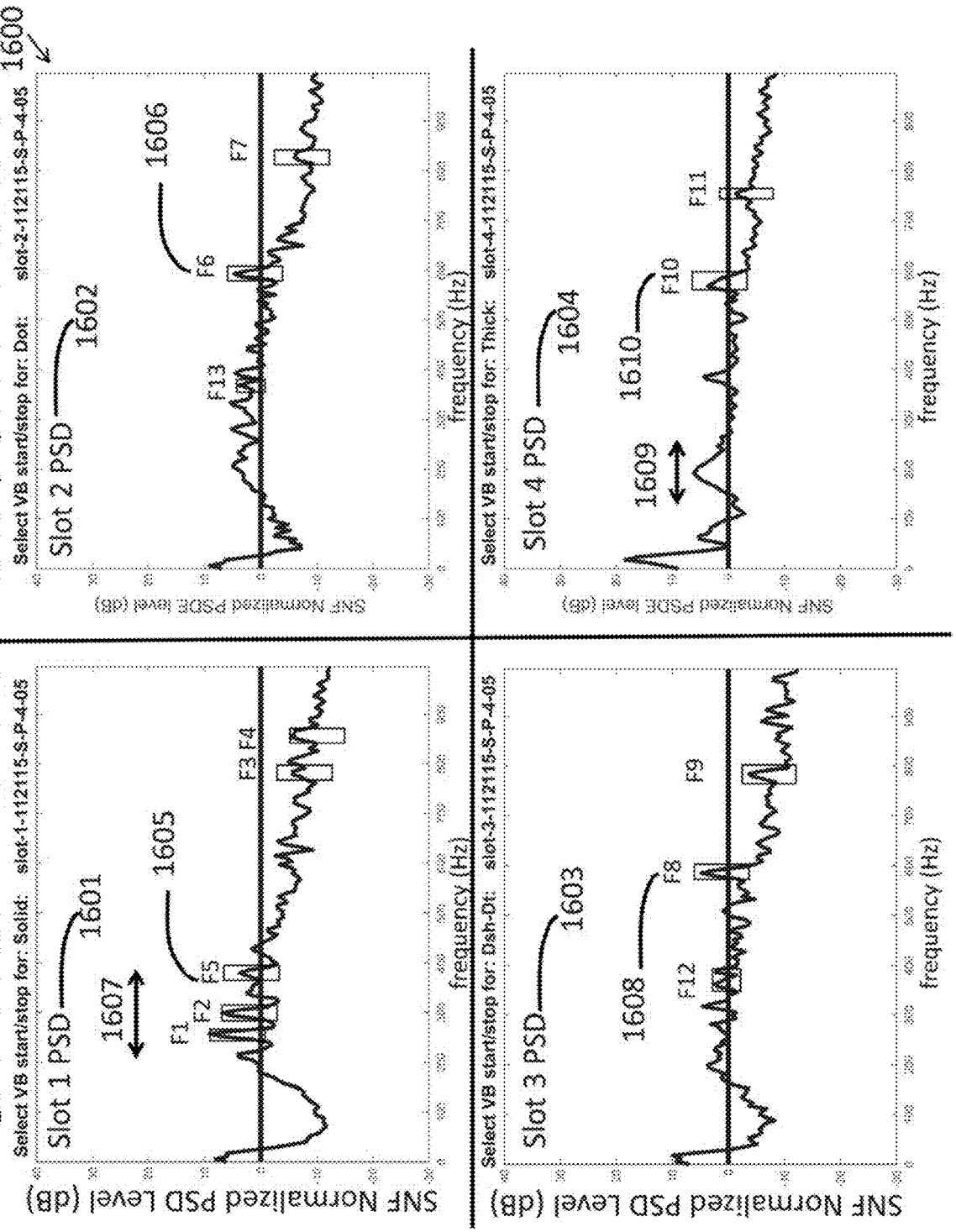

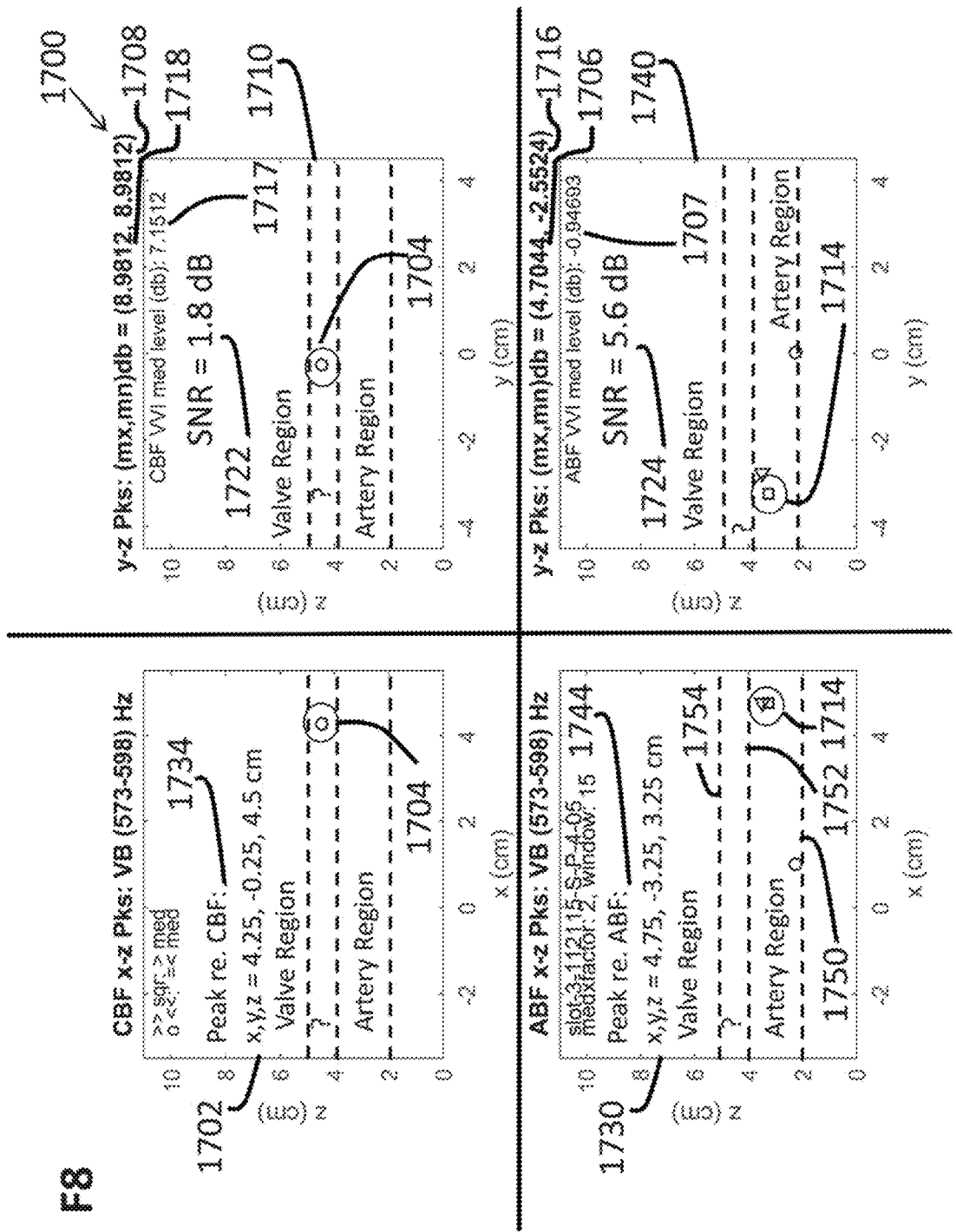
Figure 17 Case 112115 Diastolic Interval (DI) PAL localization

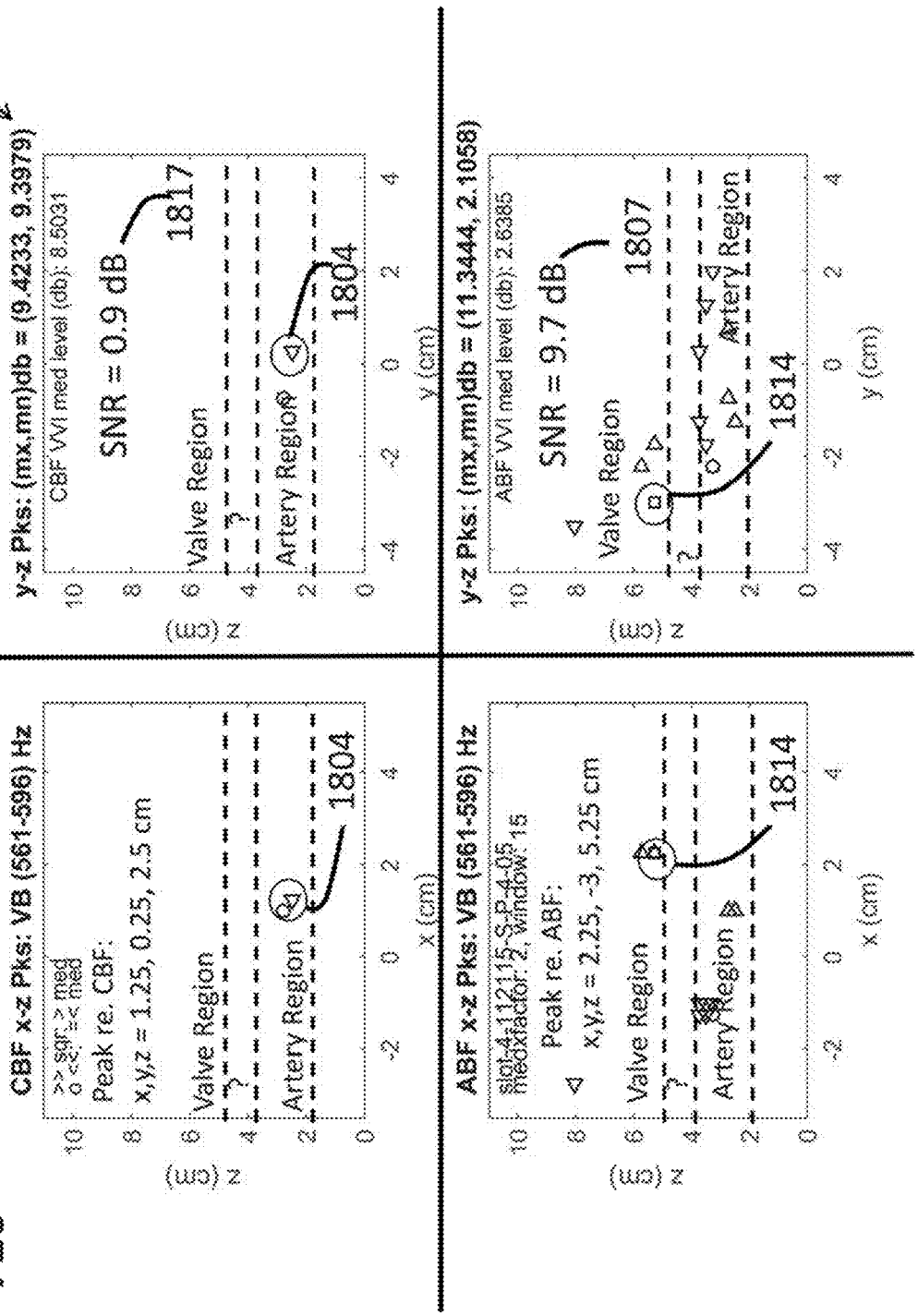
Figure 18 Case 112115 diastolic interval PAL localization results

Figure 19A  Table II. Summary of Case 112115 Diastolic Interval PAL Results (Confirm) 1900A

| Case | Slot | Feature | Band (Hz) | Beamform | SNR (dB) | x,y,z (cm) |
|---|---|---|---|---|---|---|
| 112115_05D | 1 | F1 | 249-267 | CBF | 0.3 | 4.25, 0.25, 3.25 |
| 112115_05D | 1 | | | ABF | 1.4 | 2.5, -1.25, 2.25 |
| 112115_05D | 1 | F2 | 283-311 | CBF | 0.5 | 4, 0.5, 3.75 |
| 112115_05D | 1 | | | ABF | 1.1 | 2.5, -1.25, 2.75 |
| 112115_05D | 1 | F3 | 770-793 | CBF | 3.1 | 1.75, -1.75, 4 |
| 112115_05D | 1 | | | ABF | 1.8 | 1.75, 3.25, 3 |
| 112115_05D | 1 | F4 | 848-873 | CBF | 2.7 | 4, -1.25, 5.25 |
| 112115_05D | 1 | | | ABF | 1.5 | 4, -2.5, 5.5 |
| 112115_05D | 1 | F5 | 371-389 | CBF | 3.2 | 4.25, -1.75, 4 |
| 112115_05D | 2 | | | ABF | 15.5 | 4.25, -1.75, 4 |
| 112115_05D | 2 | F6 | 582-607 | CBF | 0.1 | 1, -0.5, 2.25 |
| 112115_05D | 2 | | | ABF | 10.6 | 2.25, 0.75, 5.25 |
| 112115_05D | 2 | F7 | 818-846 | CBF | 2.3 | 1.75, -2.25, 3.75 |
| 112115_05D | 2 | | | ABF | 3.2 | 2.5, 3.75, 9.25 |

1901 1903

Figure 19B    Table II. Summary of Case 112115 Diastolic Interval PAL Results (Confirm) ~1900B

| Case | Slot | Feature | Band (Hz) | Beamform | SNR (dB) | x,y,z (cm) |
|---|---|---|---|---|---|---|
| 112115_05D | 3 | F8 | 573-598 | CBF | 1.8 | 4.25, -0.25, 4.5 |
| 112115_05D | | | | ABF | 5.6 | 4.75, -3.25, 3.25 |
| 112115_05D | 3 | F9 | 770-795 | CBF | 1.9 | 1.75, 2.0, 4.5 |
| 112115_05D | | | | ABF | 4.5 | 2.0, -2.5, 10.75 |
| 112115_05D | 4 | F10 | 561-596 | CBF | 0.9 | 1.25, 0.25, 2.5 |
| 112115_05D | | | | ABF | 9.7 | 2.25, -3.5, 5.25 |
| 112115_05D | 4 | F11 | 742-768 | CBF | 2.1 | 2.5, 0.75, 2.25 |
| 112115_05D | | | | ABF | 1.9 | 2.75, 0.5, 2.25 |
| 112115_05D | 3 | F12 | 355-403 | CBF | 6.6 | 2.5, -3, 8, 7.75 |
| 112115_05S | | | | ABF | 16.5 | 2.5, -3.5, 7.75 |
| 112115_05S | 2 | F13 | 357-375 | CBF | 2.1 | 2, 2, 4 |
| | | | | ABF | 16.2 | 2, 2, 4 |

1911, 1913

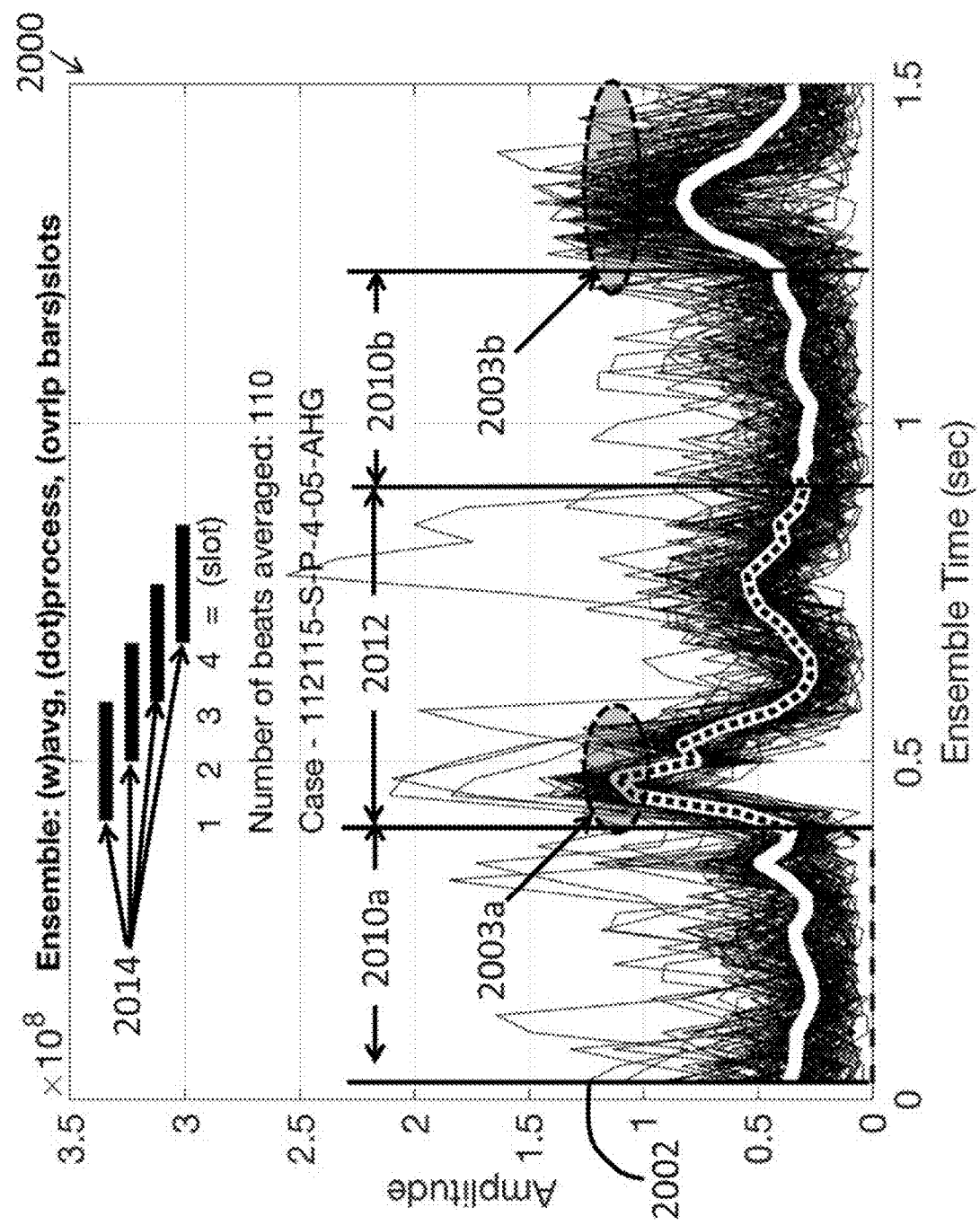

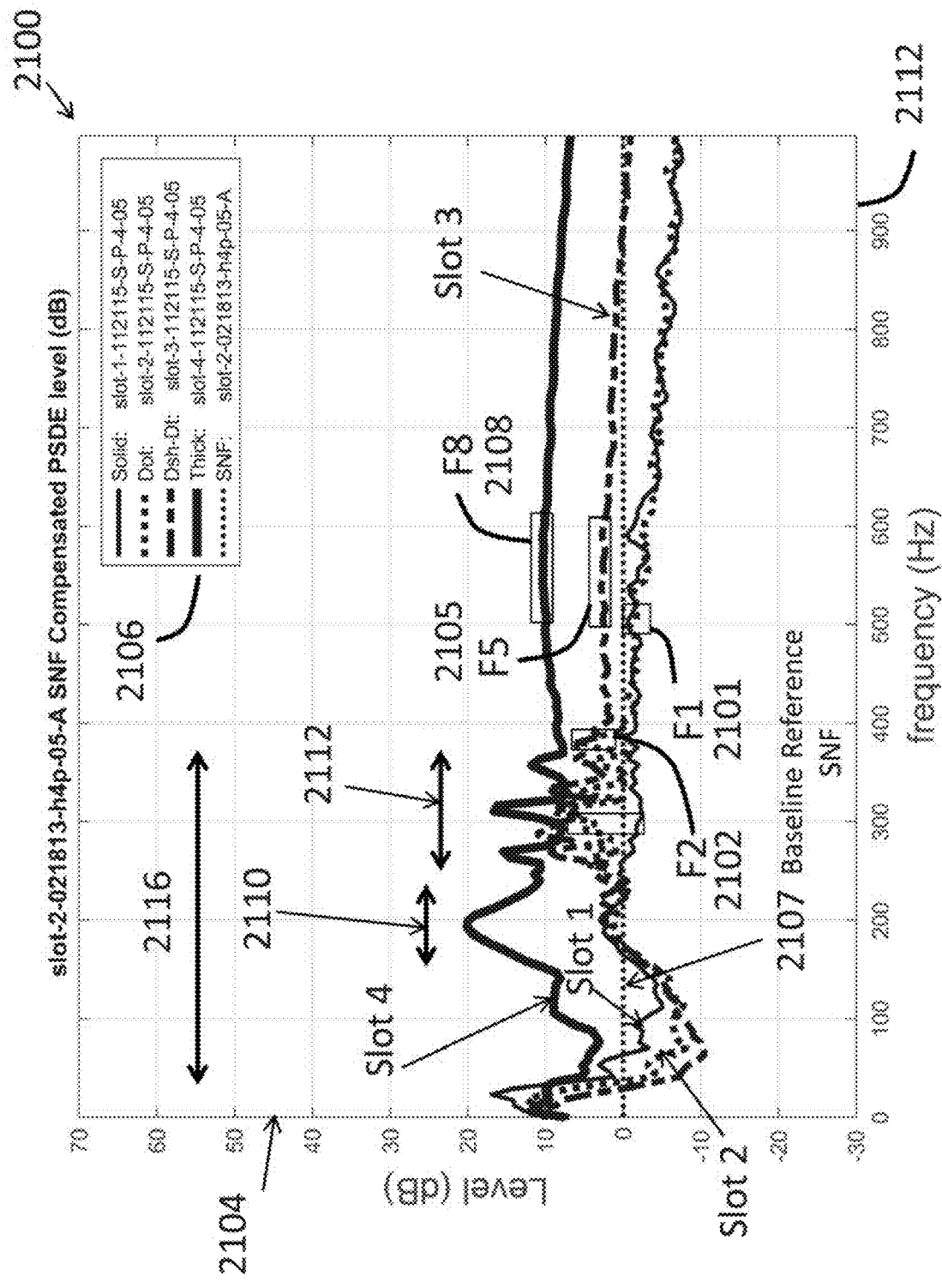
Figure 21 Case 112115-05S-Systolic Interval—Confirm Rerun Sys: Cc = 0.85, B = 123

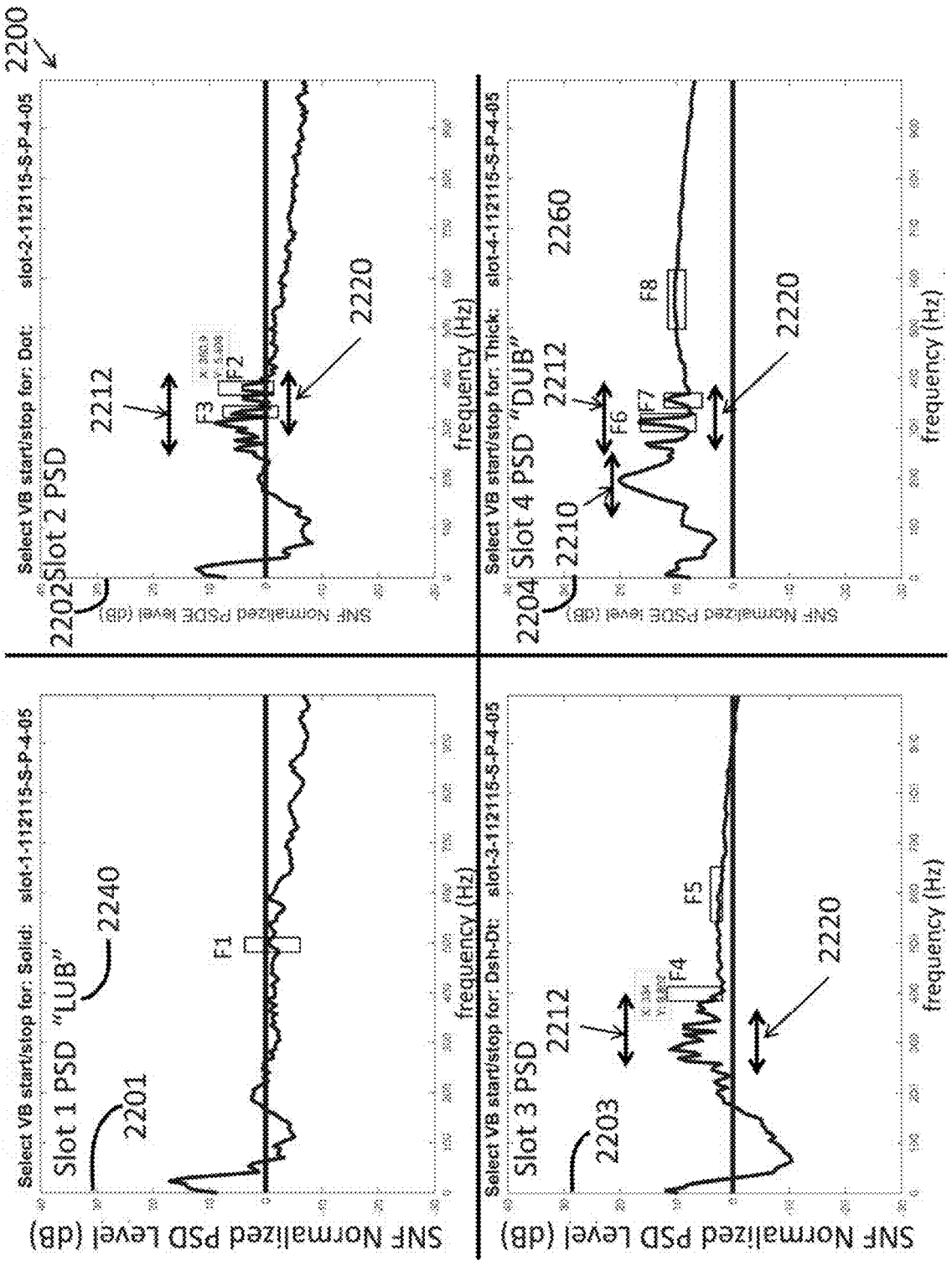

Figure 23A PAL processing results summary for Case 112115 systolic interval

| Case | Slot | Feature | Band (Hz) | Beamform | SNR (dB) | x,y,z (cm) |
|---|---|---|---|---|---|---|
| 112115_05S | 1 | F1 | 488-515 | CBF | 0.9 | 4.25, -0.25, 3.75 |
| | | | | ABF | 3.7 | 2, -1.5, 3 |
| 112115_05S | 2 | F2 | 373-391 | CBF | 4.6 | 4.25, -1.25, 4.5 |
| | | | | ABF | 13.9 | 4.25, -1, 4.5 |
| 112115_05S | 2 | F3 | 322-339 | CBF | 0.9 | 1.25, 0.25, 2.5 |
| | | | | ABF | 9.7 | 2.25, -3.5, 5.25 |
| 112115_05S | 3 | F4 | 322-343 | CBF | 4.9 | -3.5, -4.5, 2 |
| | | | | ABF | 20.1 | 4.25, -0.75, 4.25 |
| 112115_05S | 3 | F5 | 501-600 | CBF | 3.7 | 2, 3.75, 2.25 |
| | | | | ABF | 16.5 | 2, 1.5, 4.25 |
| 112115_05S | 4 | F6 | 348-368 | CBF | 1.6 | 1.75, 1.25, 3.5 |
| | | | | ABF | 3.5 | 1.75, 1.25, 3.5 |

Table II. Summary of Case 112115 Systolic Interval PAL Results (Confirm)

Figure 23B PAL processing results summary for Case 112115 systolic interval

2300B

| Case | Slot | Feature | Band (Hz) | Beamform | SNR (dB) | x,y,z (cm) |
|---|---|---|---|---|---|---|
| 112115_05(S) | 4 | F7 | 348-368 | CBF | 1.6 | 1.75, 1.25, 3.5 |
|  |  |  |  | ABF | 3.5 | 1.75, 1.25, 3.5 |
| 112115_05S | 4 | F8 | 499-600 | CBF | 4.2 | 1.75,1.25,3.25 |
|  |  |  |  | ABF | 12.3 | 1.75,1.5,3.25 |

2108

Table III. Summary of Case 112115 Systolic Interval PAL Results (Confirm)

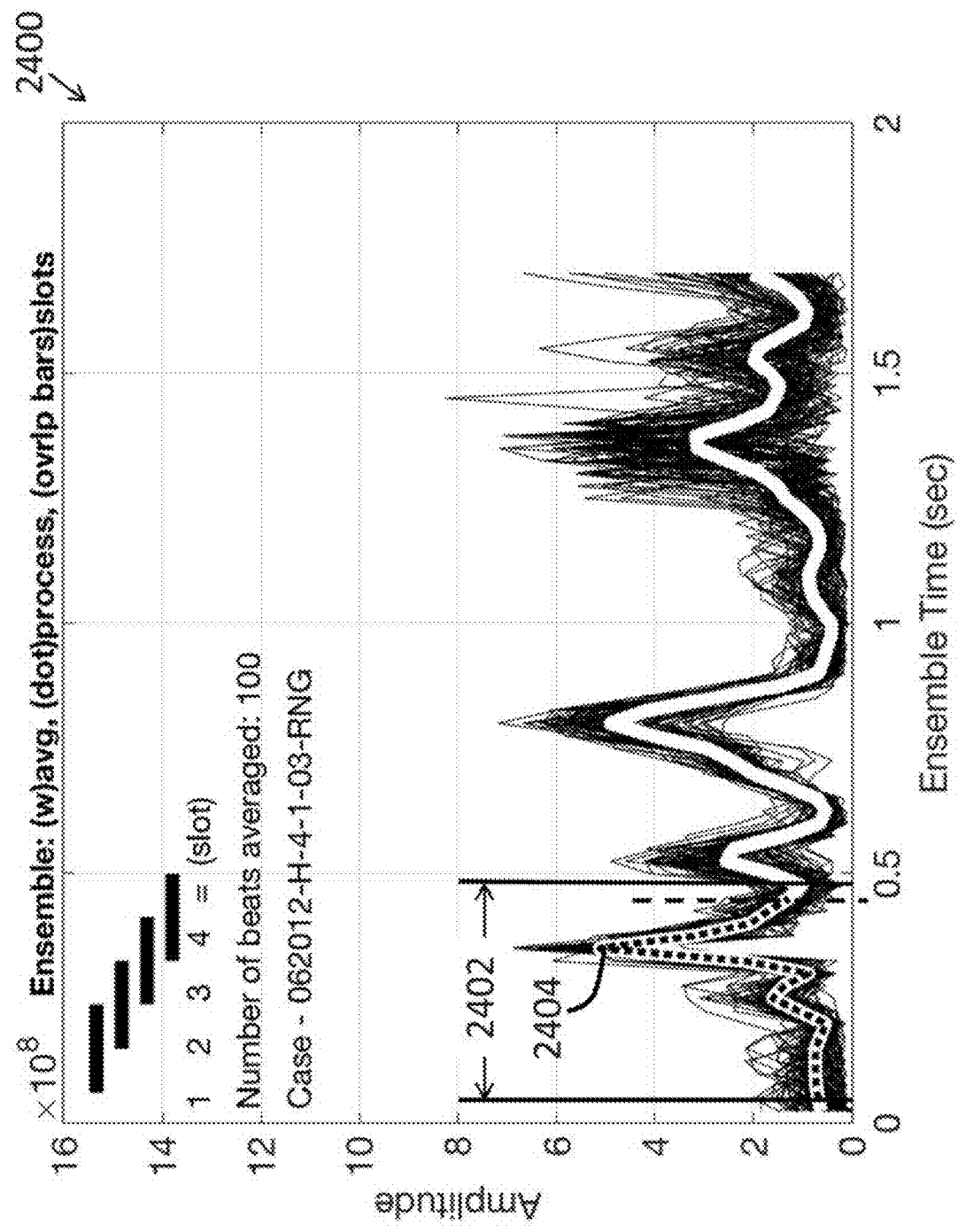
Figure 24 Amplitude ensemble for case 062012-H-4-1-03

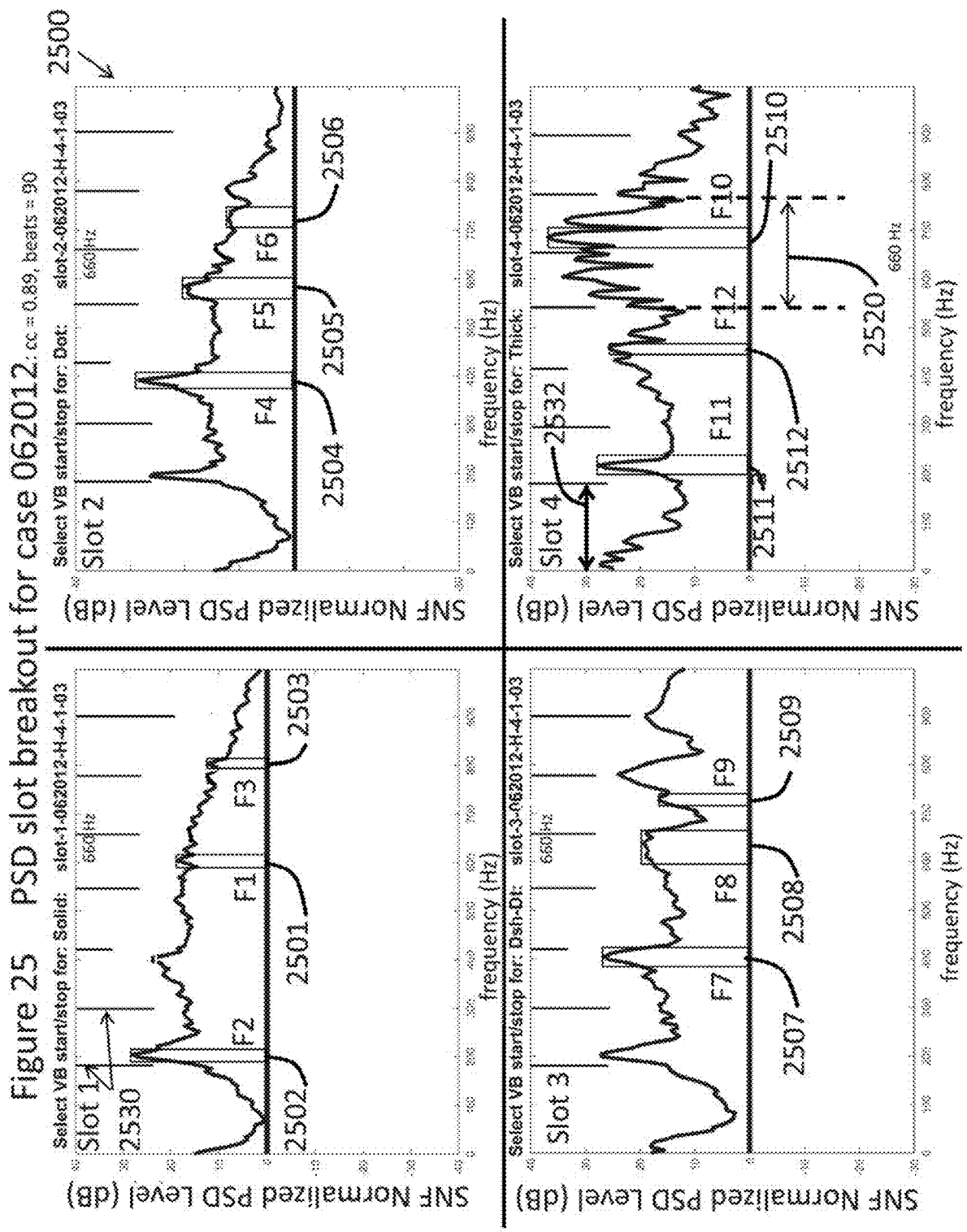
Figure 25   PSD slot breakout for case 062012

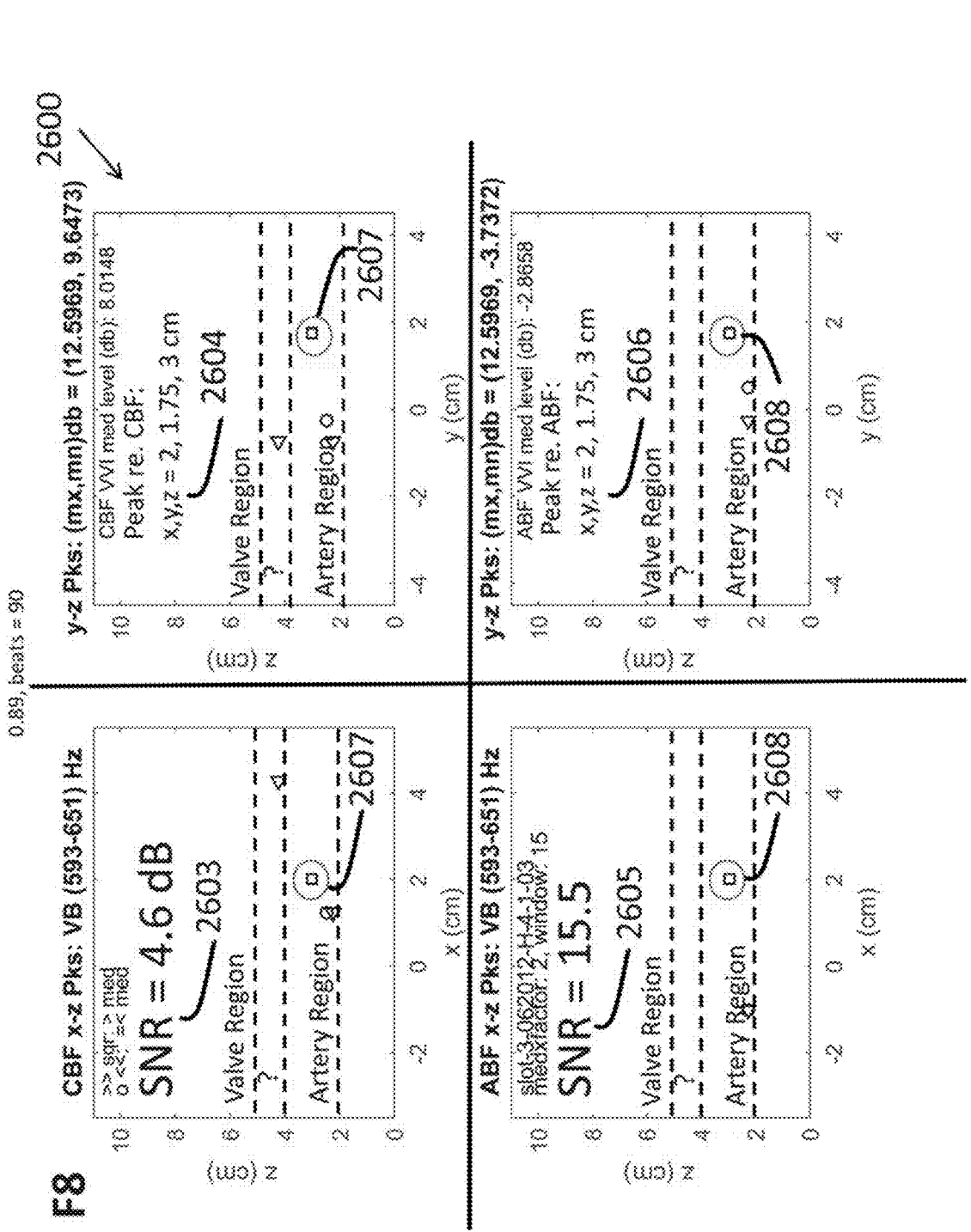
Figure 26 PAL peak intensity summary for feature F8 Case 062012

Figure 27A. Table IV summary of Case 062012 PAL analysis: cc = 0.89, beats = 90

2700A

| Case | Slot | Feature | Band (Hz) | Beamform | SNR (dB) | x,y,z (cm) |
|---|---|---|---|---|---|---|
| 062012_03D | 1 | F1 | 593-616 | CBF | 3.8 | 2, 2, 3 |
| | | | | ABF | 3.7 | 2, 1.25, 3.5 |
| 062012_03D | 1 | F2 | 194-215 | CBF | N/A | -3.5, -4.5, 2 |
| | | | | ABF | 12.8 | 2.25, 3.75, 6 |
| 062012_03D | 1 | F3 | 802-808 | CBF | 5 | 4, -1, 5.5 |
| | | | | ABF | 15.1 | 4, -1, 5.5 |
| 062012_03D | 2 | F4 | 380-407 | CBF | 3 | 4.25, 0.25, 3.75 |
| | | | | ABF | 17.2 | 4.25, 2.5, 4 |
| 062012_03D | 2 | F5 | 510-533 | CBF | 4.4 | 2, 1.5, 3 |
| | | | | ABF | 15.3 | 2, 1.5, 3 |
| 062012_03D | 2 | F6 | 706-738 | CBF | 4.5 | 2, 1.5, 3.5 |
| | | | | ABF | 12.3 | 2, -3.25, 2.5 |

Figure 27B  Table IV summary of Case 062012 PAL analysis: cc = 0.89, beats = 90

2700B

| Case | Slot | Feature | Band (Hz) | Beamform | SNR (dB) | x,y,z (cm) |
|---|---|---|---|---|---|---|
| 062012_03D | 3 | F7 | 384-419 | CBF | 3.4 | 4.25, 0.5, 3.5 |
| | | | | ABF | 10.7 | 4.5, -0.5, 3.5 |
| 062012_03D | 3 | F8 | 593-651 | CBF | 4.6 | 2, 1.75, 3 |
| | | | | ABF | 15.5 | 2, 1.75, 3 |
| 062012_03D | 3 | F9 | 715-747 | CBF | 4.3 | 3.75, 1.5, 3.25 |
| | | | | ABF | 10.1 | 3.75, 1.5, 3.25 |
| 062012_03D | 4 | F10 | 671-699 | CBF | 5.9 | 2.5, -1.75, 5.25 |
| | | | | ABF | 25 | 2.5, -1.75, 5.25 |
| 062012_03D | 4 | F11 | 201-226 | CBF | 0.5 | 4.25, 0.5, 2.25 |
| | | | | ABF | 12.4 | 2.75, 4.25, 4.25 |
| 062012_03D | 4 | F12 | 444-472 | CBF | 2.0 | 4.25, 0.75, 3 |
| | | | | ABF | 9.1 | 4, 0, 3.5 |

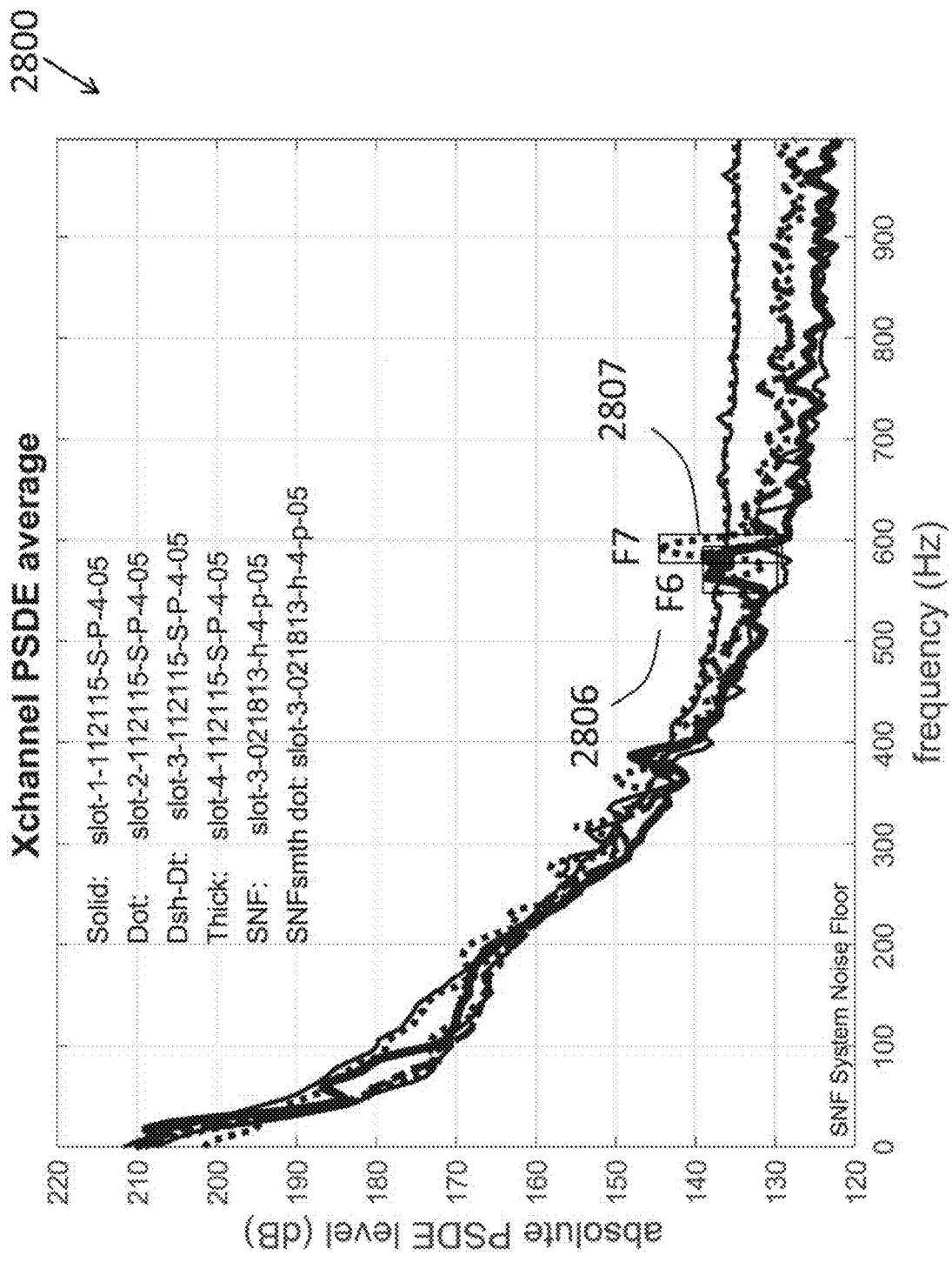
Figure 28 Case 112115 diastolic interval PSDs

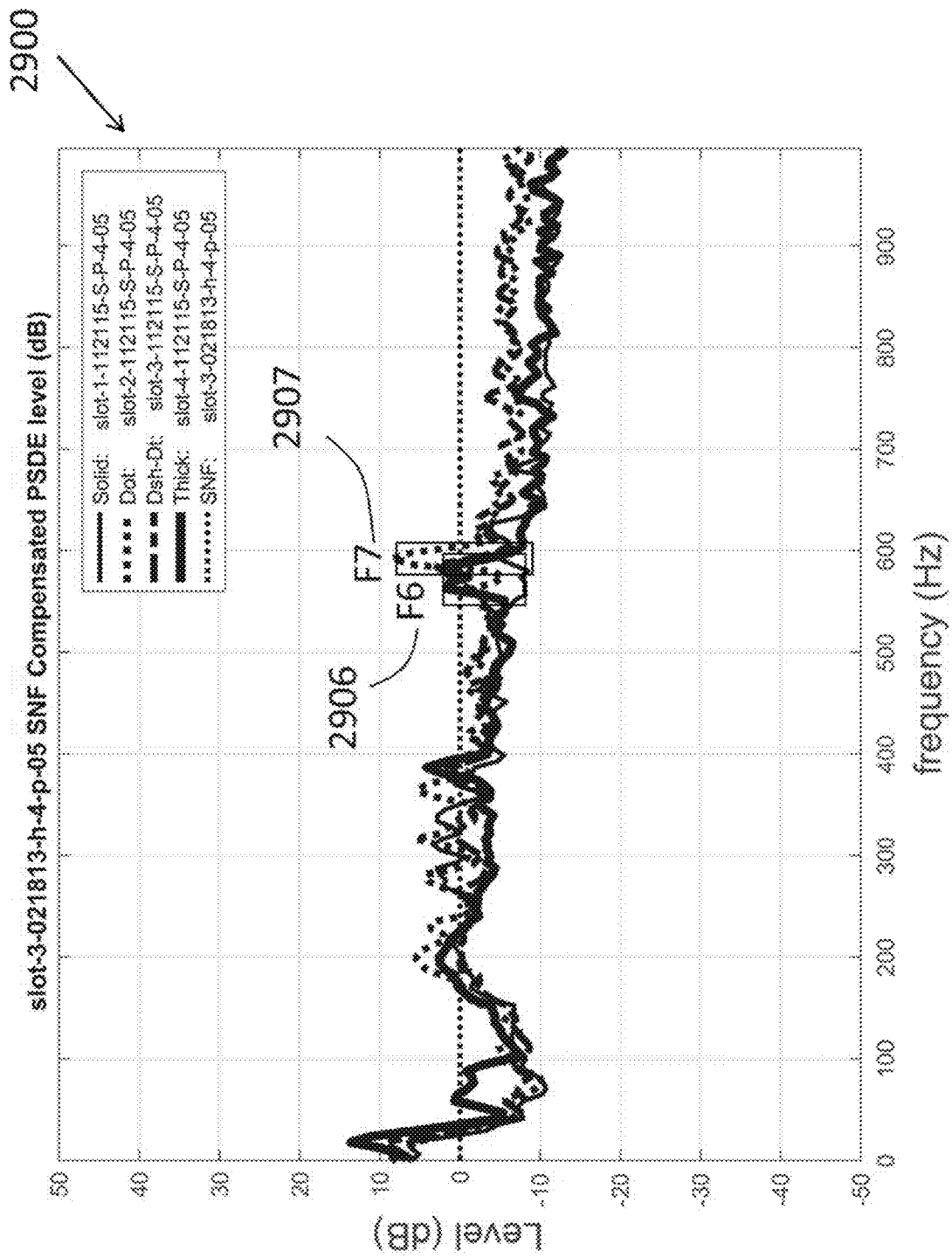
Figure 29 Case 112115 diastolic interval (DI) PSDs

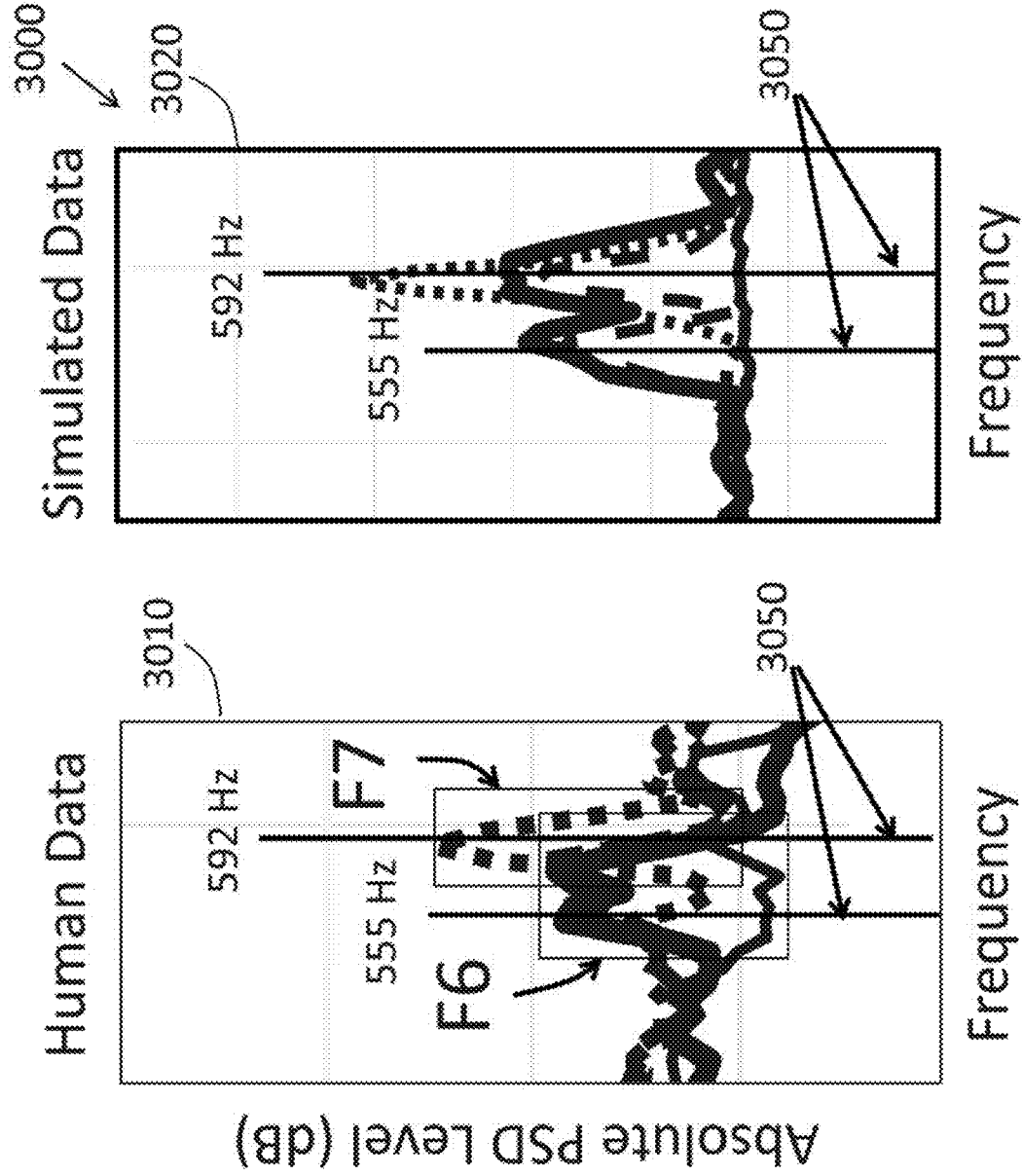
Figure 30 Human and simulated power spectral density (PSD) estimates

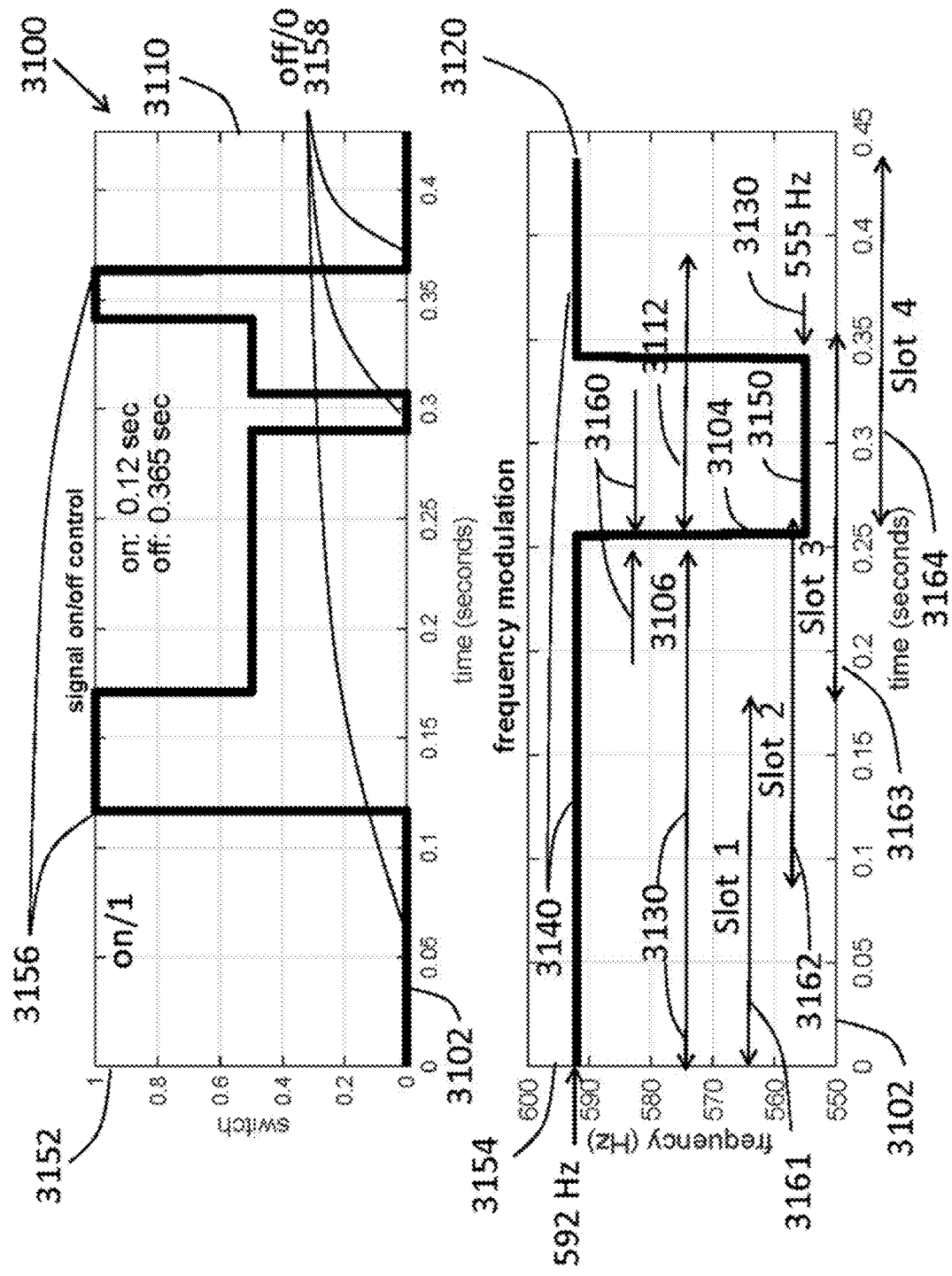
Figure 31 Timing diagram for simulated time-variable blood flow model

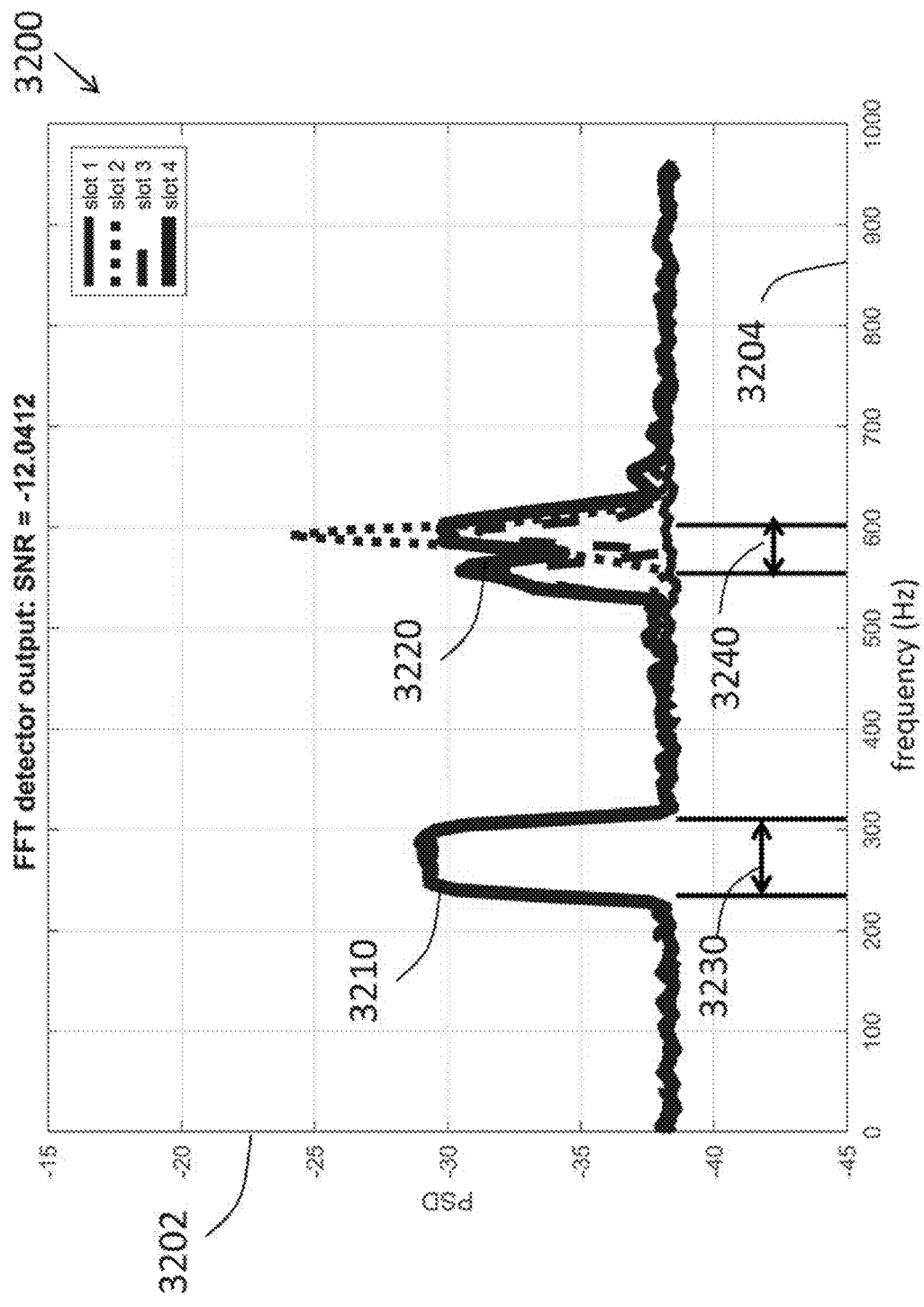
Figure 32 Continuous and discrete spectrum vibration models

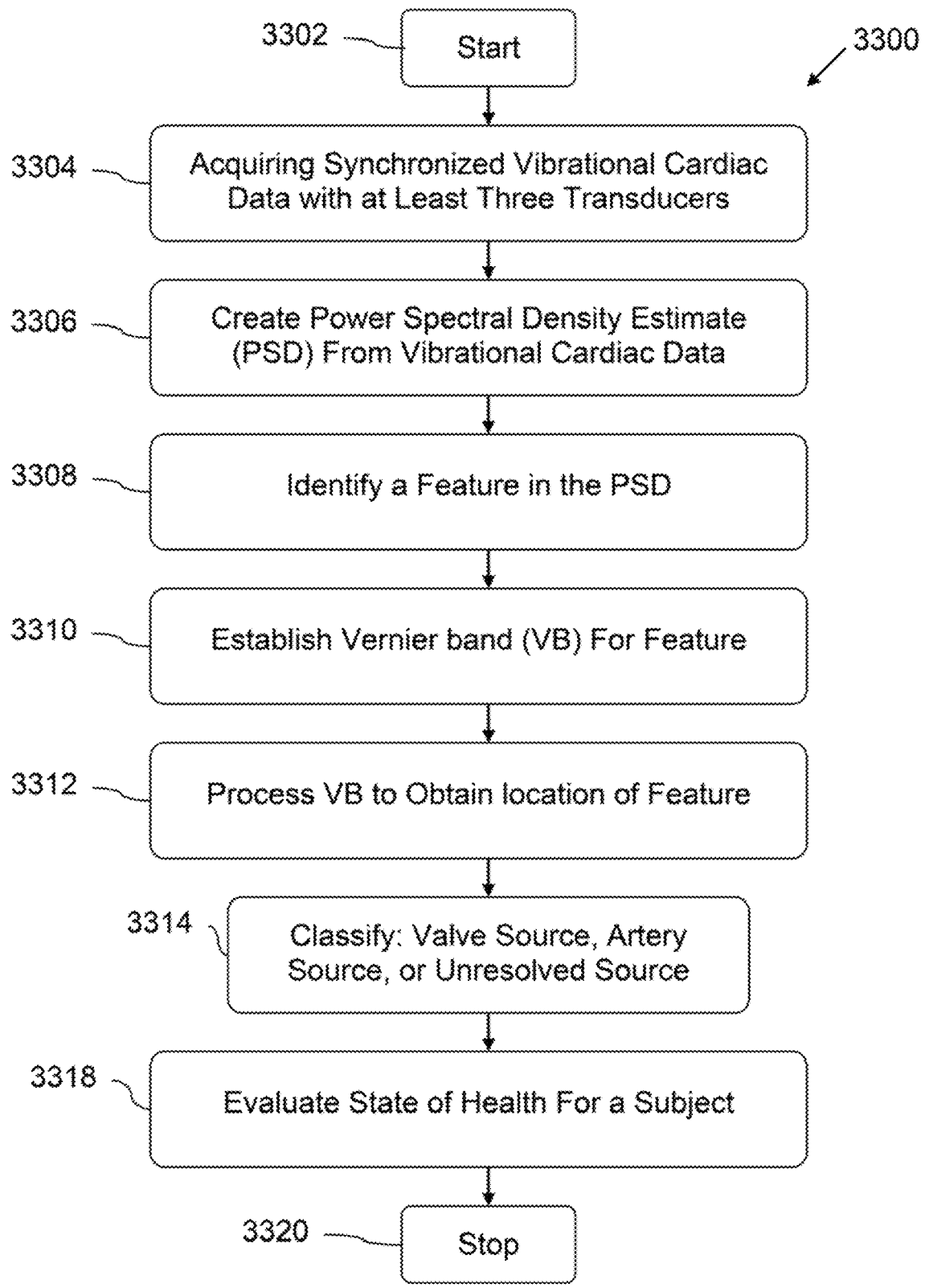
Figure 33    PAL process functional flow chart

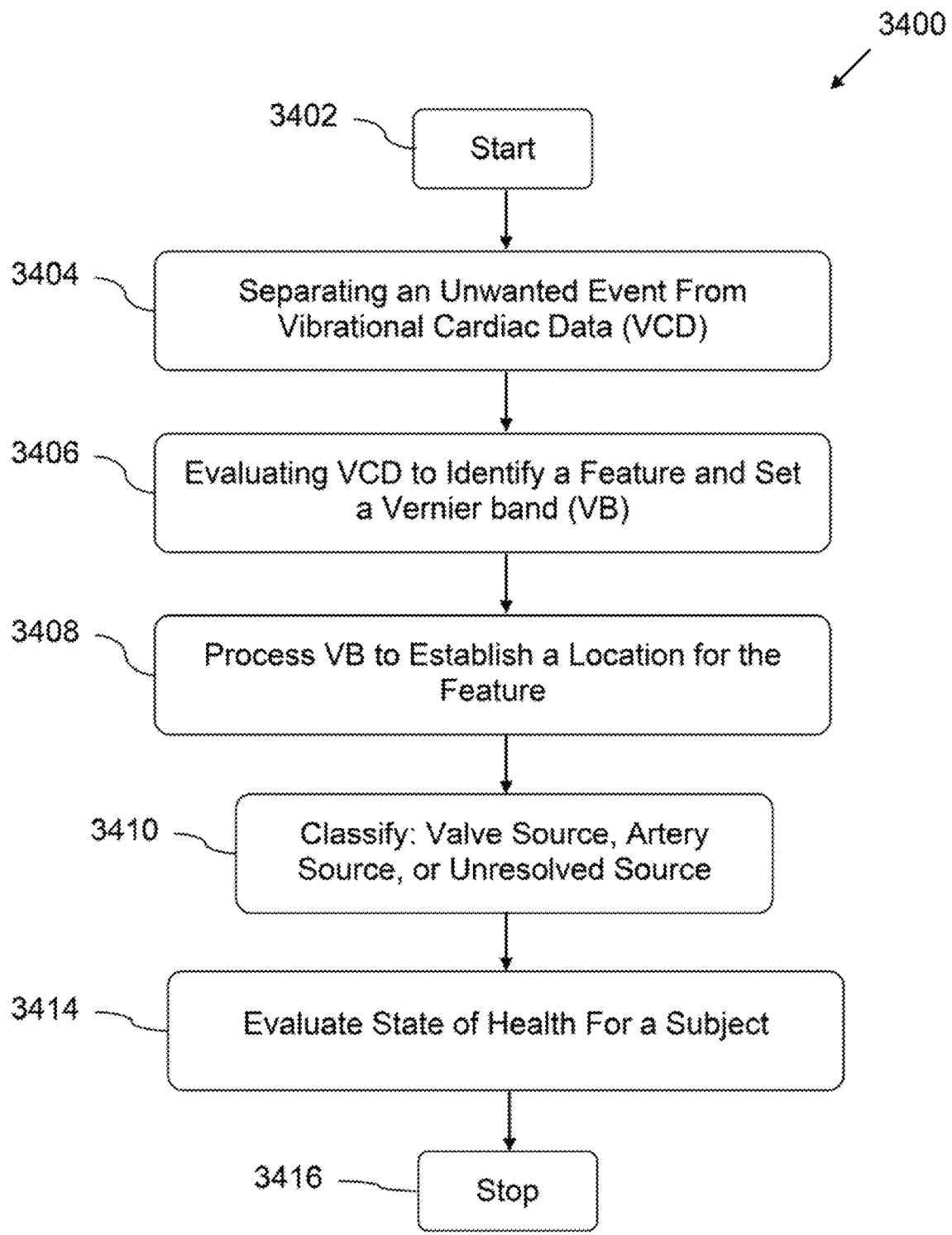
Figure 34    PAL process functional flow chart

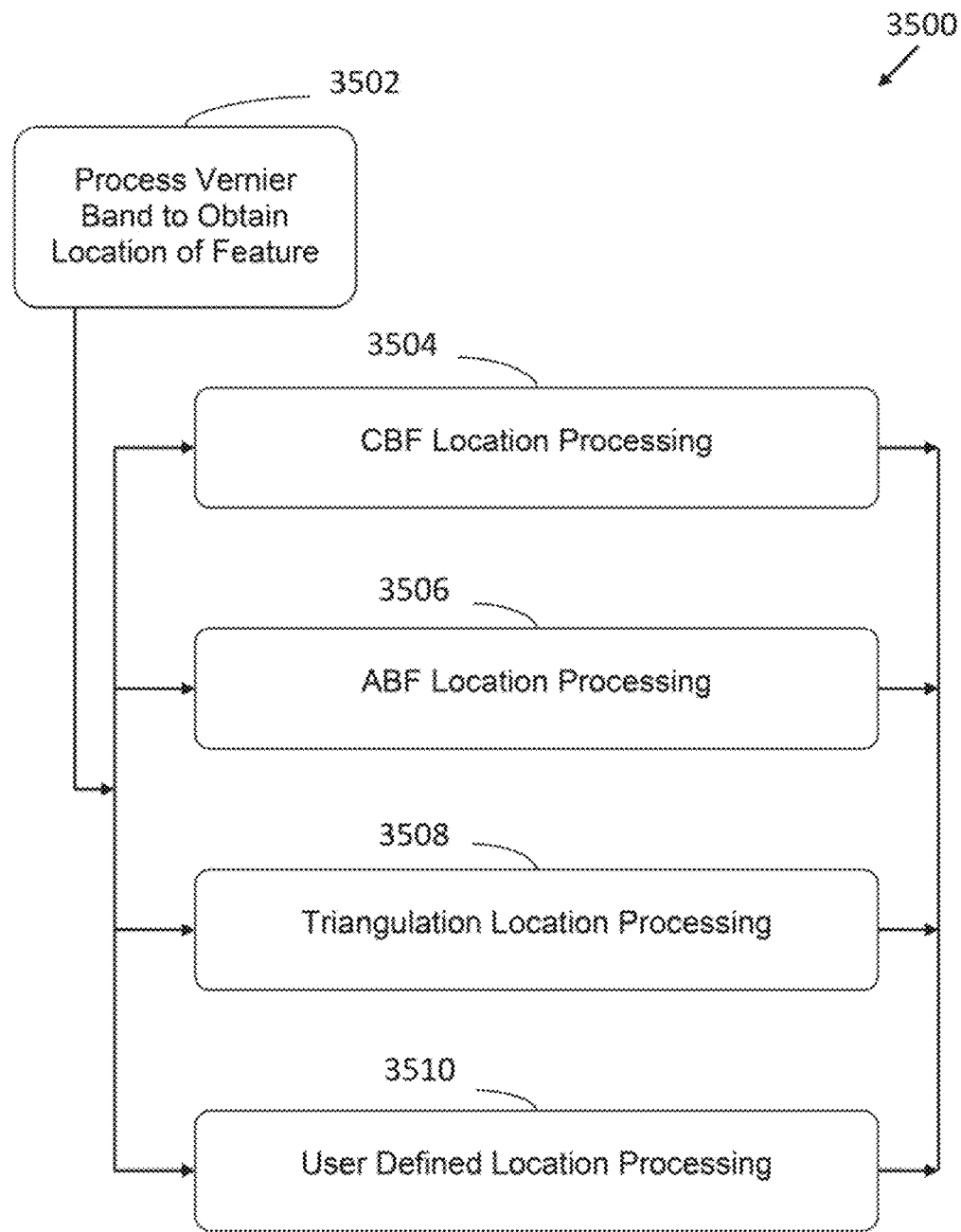
Figure 35    PAL process functional flow chart

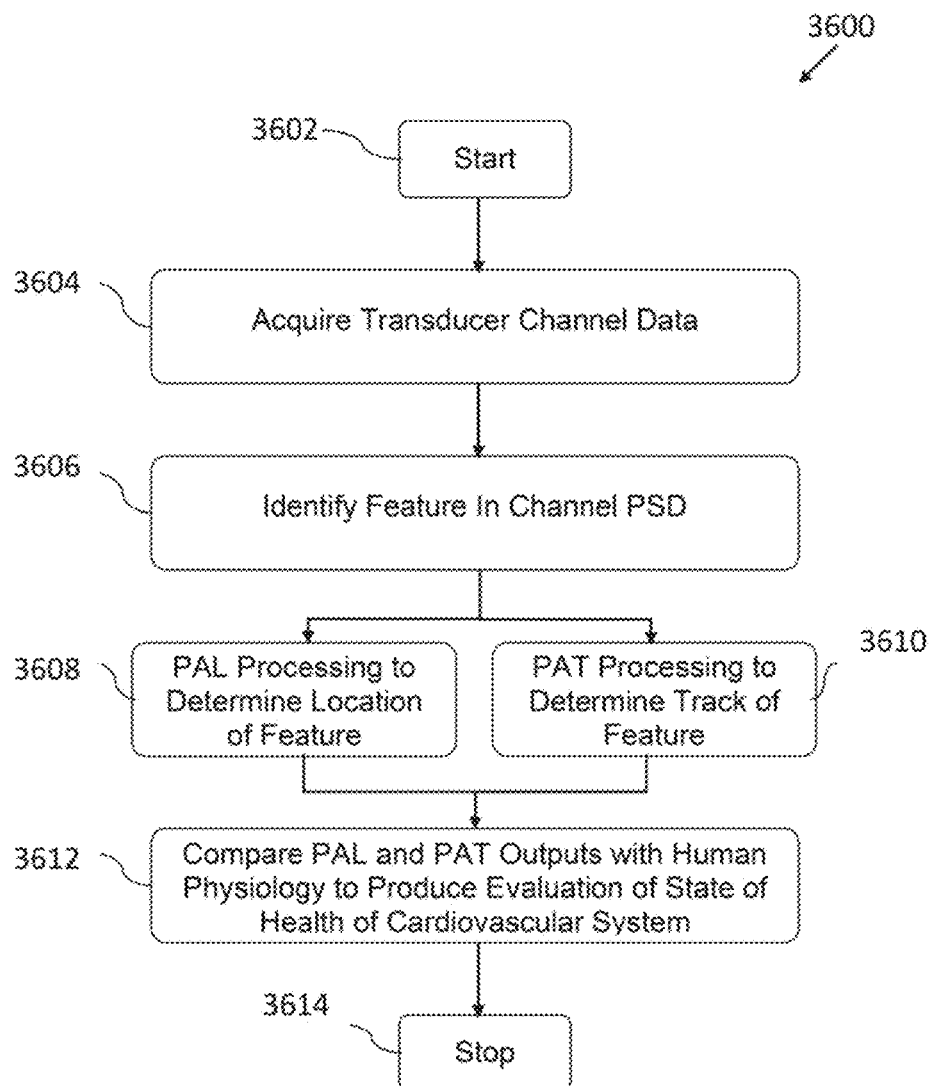
Figure 36 High level functional diagram for location and classification of detected vibration sources

SYSTEMS, APPARATUSES, AND METHODS FOR LOCATING BLOOD FLOW TURBULENCE IN THE CARDIOVASCULAR SYSTEM

RELATED APPLICATIONS

This patent application is a Divisional of U.S. Non-Provisional patent application Ser. No. 17/467,118 filed on Sep. 3, 2021, titled: "SYSTEMS, APPARATUSES, AND METHODS FOR LOCATING BLOOD FLOW TURBULENCE IN THE CARDIOVASCULAR SYSTEM, which is a Divisional of and claims priority from U.S. patent application Ser. No. 16/055,086 filed on Aug. 4, 2018, titled: "SYSTEMS, APPARATUSES, AND METHODS FOR LOCATING BLOOD FLOW TURBULENCE IN THE CARDIOVASCULAR SYSTEM, now U.S. Pat. No. 11,134,858." U.S. Non-Provisional patent application Ser. No. 17/467,118 is hereby incorporated by reference. U.S. Non-Provisional patent application Ser. No. 16/055,086 is hereby incorporated by reference.

BACKGROUND OF THE INVENTION

1. Field of the Invention

The invention relates generally to detecting and processing vibrational cardiac data, and more specifically to systems, apparatuses, and methods used for the detection, location, and classification (DLC) of blood flow turbulence induced sources of vibrational cardiac data related to coronary artery disease.

2. Art Background

Coronary artery disease is a primary precursor of heart attacks, which is a leading cause of death in the United States. Coronary artery disease is characterized by a deposition of plaque within the wall of a coronary artery, frequently resulting in a condition referred to as an occlusion, in which case blood flow may be restricted and the oxygen supply to the heart muscle may be decreased. Such a deposition of inwardly intrusive plaque is also referred to as a stenosis. Coronary artery disease can result in a heart attack and subsequent physical injury and possible death. This can present a problem.

Heart valve incompetence is characterized by abnormal blood flow through any of the four valves of the heart. Valve calcification, stenosis and valve leakage are variants of heart valve degeneration that can induce specific blood flow turbulence and vibration in the valve leaflets and contiguous valve tissue. This can present a problem.

It is known that blood flow can become increasingly turbulent as the blood passes through either an occluded artery or an incompetent valve. Turbulent blood flow provides a source of vibrational excitation within the body. The vibrational excitation causes elastic energy waves to propagate through the body and provides a motion field that can be measured at the surface of the body. Normal body functions such as breathing and the normal opening and closing of the heart's valves provide high levels of background noise relative to the magnitude of the vibrational energy resulting from blood flow induced vibration points. Such high levels of background noise can present a problem.

Currently, Coronary Artery Disease (CAD) is diagnosed post-symptomatically with some combination of a stress perfusion test and angiographic imaging. The stress test can be insufficiently accurate for either a positive or a negative diagnosis of CAD. The angiogram is costly, invasive, and places the patient at risk of injury due to complications that can arise during a required catheterization procedure. Moreover, both stress and angiographic procedures involve patient exposure to radiation. All of this can present problems.

It is known that heart valve leaflets can become calcified over time. Such calcification stiffens the valve and impairs the efficiency of flow through the valve and contributes to ancillary dysfunction of a person's cardiovascular system and can present problems to a person's state of cardiovascular health. All of this presents problems.

BRIEF DESCRIPTION OF THE DRAWINGS

The invention may best be understood by referring to the following description and accompanying drawings that are used to illustrate embodiments of the invention. The invention is illustrated by way of example in the embodiments and is not limited in the figures of the accompanying drawings, in which like references indicate similar elements.

FIG. 1A illustrates the context and apparatus, according to embodiments of the invention.

FIG. 2 illustrates the amplitude of vibrational cardiac energy as a function of time for two consecutive heart cycles, according to one embodiment of the invention.

FIG. 3 illustrates the methodology of Post (Spectrum) Analysis Localization (PAL) according to embodiments of the invention.

FIG. 4 illustrates generally the relative locations of the major coronary arteries and heart valves in a human.

FIG. 5 illustrates a conformal array of chest vibration sensors and a coordinate system for imaging vibration source localization, according to embodiments of the invention.

FIG. 6 is a photograph of an apparatus used to measure wave speed dispersion in a porcine tissue human surrogate using inverse beamforming, according to embodiments of the invention.

FIG. 7 presents both experimental inverse beamforming-derived and theoretical wave speed dispersion curves, according to embodiments of the invention.

FIG. 8 presents, for one embodiment, the ensemble of one-hundred, over-plotted, i.e. stacked, synchronized heart cycle waveform amplitude traces that define diastolic interval overlapping time slots corresponding to a Case 021813 "baseline" for normal cardiovascular health.

FIG. 9 illustrates a process for estimating the power spectral density (PSD) for a sequence of overlapping time intervals for an ensemble of heart cycles, according to embodiments of the invention.

FIG. 10 presents the "normal" baseline Case 021813 four-slot PSD estimates, according to embodiments of the invention.

FIG. 11 presents the "normal" baseline Case 021813 four-slot PSDs that have been normalized to the PSD of the second slot PSD, with spectral features identified, according to embodiments of the invention.

FIG. 12A illustrates the four PSD overlay plots of FIG. 11 in separate subplots.

FIG. 12B illustrates Case 021813 post (spectrum) analysis localization (PAL) peak intensity summary results for a vernier (frequency) band, VB, feature F1 using the fish tank orthogonal view format, according to embodiments of the invention.

FIG. 13 illustrates a summary table of PAL analysis results for the normal baseline Case 021813, according to embodiments of the invention.

FIG. 14 presents, for one embodiment, the ensemble of over-plotted, i.e. stacked, synchronized heart cycle waveform amplitude traces that define diastolic interval overlapping time slots corresponding to Case 112115 with a prior diagnosis condition of calcification of the mitral valve.

FIG. 15A presents the four-slot PSD estimates for Case 112115 with spectral features identified, according to embodiments of the invention.

FIG. 15B presents the four-slot PSD estimates for Case 112115 (FIG. 14) that have been normalized by the baseline PSD from slot 3 Case 021813.

FIG. 16 illustrates the four PSD overlay plots of FIG. 15B in separate subplots.

FIG. 17 illustrates Case 112115 PAL peak intensity summary results for a vernier (frequency) band, VB, feature F8 using the fish tank orthogonal view format, according to embodiments of the invention.

FIG. 18 illustrates Case 112115 PAL peak intensity summary for a vernier (frequency) band, VB, feature F10 using the fish tank orthogonal view format, according to embodiments of the invention.

FIGS. 19A-19B present a tabulation of PAL processing results for thirteen (13) vernier frequency band (VB) features from Case 112115 diastolic interval.

FIG. 20 presents, for one embodiment, the ensemble of over-plotted, i.e. stacked, synchronized heart cycle waveform amplitude traces that define systolic interval overlapping time slots corresponding to Case 112115.

FIG. 21 presents the four-slot PSD estimates for Case 112115, with spectral features identified, that have been normalized by the normal baseline PSD from slot 2 Case 021813.

FIG. 22 illustrates the four PSD overlay plots of FIG. 21 in separate subplots.

FIGS. 23A-23B present a tabulation of PAL processing results for eight (8) vernier frequency band (VB) features from Case 112115 systolic interval.

FIG. 24 presents, for one embodiment, the ensemble of over-plotted, i.e. stacked, synchronized heart cycle waveform amplitude traces that define the diastolic interval (DI) overlapping time slots corresponding to Case 062012.

FIG. 25 illustrates normalized PSD results in separate subplots with twelve (12) spectral features identified for the four (4) slots defined in FIG. 24 Case 062012.

FIG. 26 illustrates Case 062012 diastolic interval post (spectrum) analysis localization (PAL) peak intensity summary results for a vernier (frequency) band, VB, feature F8 using the fish tank orthogonal view format, according to embodiments of the invention.

FIGS. 27A-27B present a tabulation of PAL processing results for six (6), F1 to F6, vernier frequency band (VB) features from the Case 062012 diastolic interval as defined in FIG. 24.

FIG. 28 presents an overlay of six (6) unnormalized diastolic interval power spectral density (PSD) estimates with four derived from Case 112115 (with spectral features identified) and two derived from the Case 021813 normal baseline (unsmoothed (SNF) and smoothed (SNFsmth)), according to embodiments of the invention.

FIG. 29 presents the four-slot PSD estimates for Case 11215 in FIG. 28 that have been normalized by the normal baseline from Case 021813 slot 3.

FIG. 30 compares a sequence of both human data and simulated PSD slot data with the purpose of interpreting the effect of time variation in the morphology of a turbulent blood flow passage on sequential slot PSDs, according to embodiments of the invention.

FIG. 31 illustrates the amplitude and frequency change timing diagrams for a simulated time-variable blood flow model, according to embodiments of the invention.

FIG. 32 illustrates a side-by-side comparison of the PSD estimate features resulting from the simulation of a continuous spectrum and a time variable discrete vibration event.

FIG. 33 illustrates methods for implementing the detection, localization and classification (DLC) of a turbulent blood flow induced vibration source according to embodiments of the invention.

FIG. 34 illustrates another method for implementing the DLC of a turbulent blood flow induced vibration source according to embodiments of the invention.

FIG. 35 illustrates alternative embodiments of the methodology for locating the source of a vibration induced by turbulent blood flow in the human cardiovascular system, according to embodiments of the invention.

FIG. 36 gives a high level functional diagram for PAL location and PAT classification of detected vibration sources.

DETAILED DESCRIPTION

Figure 1B:
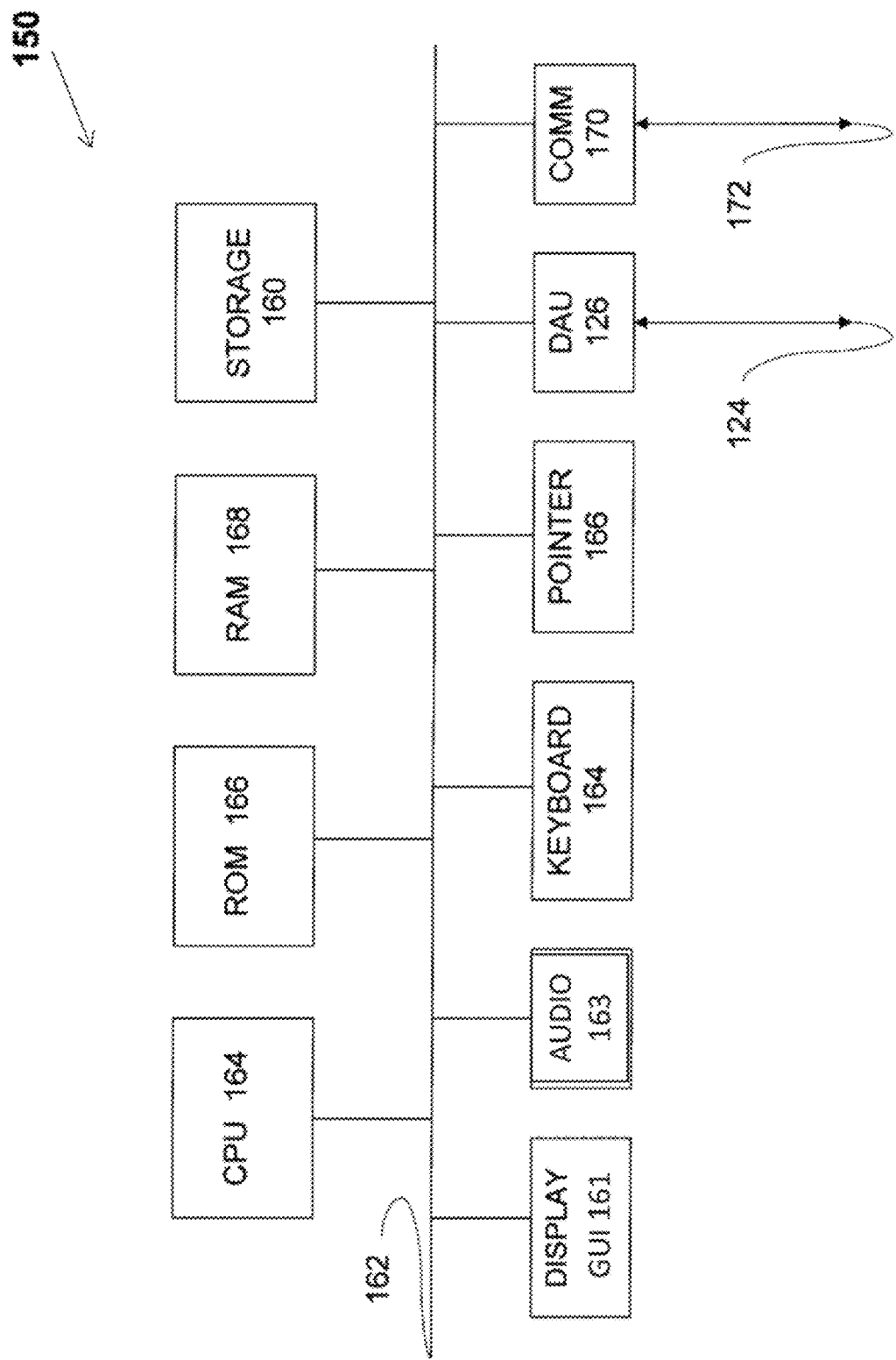
FIG. 1B illustrates a block diagram of a computer system (data acquisition system) in which embodiments of the invention may be used.

In the following detailed description of embodiments of the invention, reference is made to the accompanying drawings in which like references indicate similar elements, and in which is shown by way of illustrative examples, specific embodiments in which the invention may be practiced. These embodiments are described in sufficient detail to enable those of skill in the art to practice the invention. In other instances, well-known circuits, structures, and techniques have not been shown in detail in order not to obscure the understanding of this description, The following detailed description is, therefore, not to be taken in a limiting sense, and the scope of the invention is defined only by the appended claims.

The apparatus and methodology are described for detecting, locating and classifying vibrational cardiac data in a human. In one or more embodiments, the vibrational cardiac data arises from turbulent blood flow in a coronary artery. In another embodiment the vibrational cardiac data arises from blood flow through a heart valve. In yet another embodiment, vibrational data is simulated and measured using a human phantom with an occlusion.

FIG. 1A illustrates the use of a chest vibration sensing apparatus generally at 100, according to one embodiment of the invention. With reference to FIG. 1A, a section of a human thorax containing two ribs at 114 adjoined to the sternum at 128 and separated by an intercostal space at 115 are graphically represented. Under the ribs both a coronary artery segment at 102 having a flow of blood at 104 and a mitral valve with blood flow at 148 with flow induced valve leaflet vibration at 146 and 150 are represented. The directional flow of arterial blood 104 can interact with a coronary artery lesion 108 and cause an excitation 110 of the artery wall by known physical means, which include transition to turbulent flow 106 and the corresponding application of forces normal to the inner wall of the coronary artery. Such excitation of the coronary artery wall results in vibrational energy 110 propagating to the surface of the human chest through the intercostal space at 115. Likewise, valve leaflet calcification at 150 can result in leaflet stiffness that, in turn, amplifies turbulence-induced vibration.

In this description of embodiments, the term "sensor" is synonymous with the terms "channel" or "sensor channel," whereby a separate measurement for each channel is contemplated. Additionally, the term "sensor" is synonymous with the terms "transducer" or "sensing transducer." Thus, a first sensor's output (a first channel) and a second sensor's output (a second channel) are each available for analysis and each represents a separate measurement of a field quantity of interest, such as the vibration field in a human's body. As will be noted by those of skill in the art, in some instances, it might be advantageous for measurement sensitivity to mathematically combine together, in series or parallel, several sensors into a single channel. Such combinations can be made within the scope of the descriptions provided herein. However, to simplify the discussion, "sensor" will be understood to be synonymous with the terms "sensor channel," "channel," "transducer," or "sensing transducer."

In FIG. 1A, a conformal array of sensors at 116 measures the vibration of the surface over the intercostal space 115 and acquires vibrational cardiac data thereby. The array of sensors 116 is made up of a general number of N (≥2) sensors (sensing transducers or transducers). In one embodiment, the number N equals 14 and the spacing between adjacent transducers is one-quarter inch (0.25"). Those of skill in the art of discrete sensor array design will recognize that the array of N sensors at 116 can be configured with a different number of sensors, a different sensor width, and/or sensor spacing. The example given herein is provided merely for illustration of a specific design and does not limit embodiments of the invention.

The representational view of the human in FIG. 1A presents a non-homogeneous media through which the vibrational energy 110 propagates and contains various structures such as ribs 114 as well as lungs, organs, interfaces, muscles, fat, and skin tissue. The vibrational energy propagates through the non-homogeneous media with a composite, average vibration wave propagation speed and is measured on the skin surface by the array of N sensors 116. In one embodiment, it can be desirable to place the array of sensors 116 over a person's heart and above an intercostal space between adjacent ribs to facilitate sensing of the vibrational energy with minimal anatomically related inhomogeneity.

In one embodiment, each sensor of the array of sensors 116 is made from a strip of polyvinylidene fluoride (PVDF) film. In one example, each strip of PVDF film measures 0.75 inches long, between attachments to a chassis 122, and 0.1875 inches wide. Each strip of PVDF film is stretched into a flat plane and is anchored at each end by the chassis 122. At the midpoint of each strip of PVDF film, a rigid pad is placed to provide an area of contact between the skin surface and the strip of PVDF film. An example of one such sensor from the array of sensors 116 is illustrated by a strip of PVDF film 130, having a first end 132 and a second end 134 (which are attached to the chassis 122) and a pad 136 that makes contact with the skin surface. In one embodiment, the diameter of the pads is 0.1875 inches and the thickness of the pads is 0.0625 inches.

The sensitivity of the PVDF film along its major axis is 22176 V/unit strain for a PVDF film thickness of 0.028 millimeters. The PVDF film generates a voltage in response to strain imparted from the vibrating motion 138 of the skin surface. In one embodiment, the chassis 122 is made out of metal such as aluminum, in other embodiments the chassis 122 is made out of plastic or another material sufficient to provide the necessary anchor points for the strips of PVDF film.

Each sensing transducer is in electrical contact with at least one preamplifier 120 using connection 118. It is advantageous to place a preamplifier proximate to its sensing transducer in order to minimize the addition of excessive electronic noise. Additional amplification stages can be used and in one embodiment the outputs from the preamplifiers 120 are passed to a bank of amplifiers. In one embodiment, the outputs of the sensing transducers (array 116) are carried in a cable bundle 124 and are processed in a data acquisition system 126 that can contain a graphical user interface (GUI).

Those of skill in the art will appreciate that adjustments to the array geometry can be made, i.e., sensor dimensions and sensor spacing. Vibrational energy 110 includes shear wave energy propagation with shear wavelengths on the order of several tens of millimeters, e.g. approximately 40 millimeters at 200 cycles per second and approximately 20 millimeters at 500 cycles per second.

FIG. 1A contains a representation of the mitral valve that is significant as a source of vibration 146 induced by blood flow through the valve leaflet orifice. The proximity of the mitral valve 146 to the coronary artery 102 and the simultaneous flow of blood through the artery and the valve requires a careful process of combined localization and spectrum classification in the analysis as described herein.

FIG. 1B illustrates, generally at 150, a block diagram of a computer system (data acquisition system) in which embodiments of the invention may be used. The block diagram is a high-level conceptual representation and may be implemented in a variety of ways and by various architectures. With reference to FIG. 1B, a data bus system 162 interconnects a Central Processing Unit (CPU) 164, Read Only Memory (ROM) 166, Random Access Memory (RAM) 168, storage 160, a GUI display 161, audio 163, keyboard 164, pointer 166, data acquisition unit (DAU) 126, and communications 170. The bus system at 162 may be for example, one or more of such buses as a system bus, Peripheral Component Interconnect (PCI), Advanced Graphics Port (AGP), Small Computer System Interface (SCSI), Institute of Electrical and Electronics Engineers (IEEE) standard number 1394 (Fire Wire), Universal Serial Bus (USB), or a dedicated bus designed for a custom application, etc. The CPU 164 may be a single, multiple, or even a distributed computing resource. Storage 160 may be Compact Disc (CD), Digital Versatile Disk (DVD), hard disks (HD), optical disks, tape, flash, memory sticks, video recorders, etc. The computer system 150 can be used to receive vibrational cardiac data via 124 from the array 116 of vibration sensors (FIG. 1A). Note that depending upon the actual implementation of a computer system, the computer system may include some, all, more, or a rearrangement of components in the block diagram.

Thus, in various embodiments, vibrational cardiac data is received at 124 for processing by the computer system 150. Such data can be transmitted via communications interface 170 for further processing and diagnosis in a remote location, as illustrated in FIG. 1B at 172. Connection with a network, such as an intranet or the Internet is obtained via 172, as is recognized by those of skill in the art, which enables the data processing device 150 to communicate with other data processing devices in remote locations.

For example, embodiments of the invention can be implemented on a computer system 150 configured as a desktop computer or work station, on for example a WINDOWS® compatible computer running operating systems such as WINDOWS XP Home or WINDOWS XP Professional, WINDOWS 10, Linux, etc. as well as computers from APPLE COMPUTER, Inc. running operating systems such as OS X, etc. Alternatively, or in conjunction with such an implementation, embodiments of the invention can be configured with devices such as parallel computing devices, speakers, earphones, video monitors, etc. configured for use with a Bluetooth communication channel.

FIG. 2 illustrates, generally at 200, a graphical representation of the amplitude of vibrational cardiac data as a function of time for two heart cycles, according to one embodiment of the invention. With reference to FIG. 2, a representative output from one of the vibration sensors, from array 116 (FIG. 1A) is illustrated, where a magnitude of the sensor's output is plotted on a vertical axis 204 as a function of time 202. A first heart cycle 206 contains a first peak 208 corresponding to the closure of the mitral (M) and tricuspid (T) valves and referred to as the "S1" sound. This first peak is described informally as a "lub" sound when heard through a stethoscope. The first heart cycle 206 contains a second peak at 210, referred to as the "S2" sound, which corresponds to the closure of the two semi-lunar, aortic (A) and pulmonic (P) valves at the beginning of the diastolic period 212. This second peak is described in the literature as a "dub" sound when heard through a stethoscope. The diastolic period 212 follows the second peak 210 and continues to the next S1. In some cases, the S1 and S2 sounds split into resolvable sounds corresponding to the closure of each valve in the composite valve closure event.

The heart continues to beat, and a second heart cycle 226 is produced thereby with the same major features found in the first heart cycle; a first S1 peak at 228, followed by a second S2 peak at 230, and a diastolic interval (DI) 232. Successive heart cycles (not shown) will continue to occur as the heart continues to beat. During the diastolic intervals, 212, 232, etc., blood flow is at a maximum in the coronary arteries and unwanted coronary events, such as the first peaks 208, 228 and the second peaks 210, 230 are separated in time and their masking effect on the diastolic interval vibration signal data is at a minimum.

In one embodiment, it is desirable to process vibrational cardiac data accumulated over a plurality of forty (40) to one hundred and twenty (120) or more heart cycles in order to provide a sufficiently long averaging time record for an array of 14 channels. In practice, with human test subjects, it has been observed that the human test subjects can comfortably breath-hold for approximately twenty (20) heart cycles. In this scenario, a human test subject will alternate between breath-bold and normal breathing. for breath recovery, while the heart waveforms are digitally acquired. In one embodiment, a nominal duration of the entire heart waveform is from one hundred and twenty (120) to one hundred and eighty (180) seconds and is made up of six (6) twenty (20) to thirty (30) second segments. In another embodiment, the number of acquired heart cycles is approximately equal to four (4) to ten (10) times the number of sensor channels in array N. Such a number of heart cycles are needed to adequately resolve the numerically higher eigenvalues of an inter-sensor cross-spectral density matrix (CSDM) which is a frequency domain correlation matrix as described below in sections of the following discussion on localization using beamforming techniques. A shorter duration of heart data acquisition (fewer heart cycles) can be collected if the CSDM eigenvalue range is limited accordingly. Those of skill in the art will appreciate that the entire heart waveform can vary in length and that the examples provided herein are given for illustration only and do not limit embodiments of the invention. Further discussion of the CSDM is provided below.

The number of heart cycles over which a human test subject can comfortably breath-hold will vary between human test subjects and will depend on many factors such as age, physical condition, medical condition, etc. When vibrational cardiac data is collected during breath-hold, the effects of breathing on the measured vibrational cardiac data are minimized. The number of segments can be adjusted to accommodate the particular test conditions as determined by the length of time that the human test subject can breath-hold and the number of sensor channels in the array N. In one embodiment, a human starts and stops the acquisition of the vibrational cardiac data to coincide with acquisition during breath-hold periods. In another embodiment, a human is not required to breath-hold and the data is parsed either manually or automatically to separate the desired intervals from the periods with excessive unwanted background noise.

FIG. 3 illustrates, generally at 300, a method referred to as post (spectrum) analysis localization (PAL) for processing vibrational cardiac data, according to embodiments of the invention. The PAL method is applied to vibrational cardiac data that is acquired with an array of N sensing transducers (N≥2), which are mounted on the surface of a human's body as described above in conjunction with the previous figures. With reference to FIG. 3, a method starts at a block 302.

For the purpose of extracting the same particular interval from the respective heart cycles in an ensemble, at a block 304 a single high-quality channel is selected from the array of N sensing transducers. A high-quality channel has a high signal-to-noise ratio (SNR), wherein the signal-to-noise ratio is expressed as the ratio between the height of a first peak of a heart cycle and the background level during the diastolic interval and the height of a second peak of the heart cycle and background level of the vibrational cardiac data. A technician can perform the selection of a high-quality channel or it can be automated in a selection algorithm that would be performed by a data processing system such as the computer system (data acquisition system) described above in conjunction with FIG. 1b. FIG. 3 requires that heart cycles be synchronized and parsed such that averaging over the entire ensemble of cycles during corresponding portions of the cycle is achieved. This is a form of heart cycle time "strobing" such that the same subinterval of a sequence of acquired heart cycles are aligned and then concatenated to produce a long, statistically stationary time sequence that is effectively acquired from the same time window in the heart cycle. In various embodiments the synchronization is accomplished without the use of an electrocardiogram (ECG) as a time reference.

Optionally, at a block 306, the power spectral density (PSD) for the acquired ensemble of heart cycles is estimated by averaging over heart cycle number and sensor number. At 308, the ensemble averaged PSD is searched for features of the PSD that are possible indicators of vibrational energy. These features would include high PSD levels relative to a normal healthy PSD baseline over either wide portions of the spectrum (low Q value) and/or a narrow, frequency band limited resonant segment (high Q value) of the spectrum. The frequency bands containing features are referred to as vernier bands (VBs) at 308.

At 310, a process is implemented that uses the sensor-to-sensor measured correlation as a function of frequency, referred to as coherence, to estimate the location of vibration sources in each of the VBs. This allows the classification at 312 and 314 of sources by both frequency spectrum analysis and spatial location (localization). At 316 the Post (spectrum) Analysis Localization (PAL) procedure is concluded.

With reference to FIG. 3, a procedure is functionally defined that contains the processing routines of DLC: Detection (D) by spectrum analysis, Localization (L) by spatial search routines, and Classification (C) by feature characteristics. To illustrate the nature of the DLC process, FIG. 4 generally at 400 shows a representational cross-section of the heart looking from the top generally at the level of the heart valves. The morphology and location of cardiovascular components (e.g., heart valves, arteries, etc.) in FIG. 4 has been created from archival human anatomy topography data which is known a priori. The anterior (front) surface of the heart is generally to the bottom right and the chest surface over the heart is indicated at 452. Three depth levels along the z-axis are indicated: 2 cm at 440, 4.0 cm at 460 and 5 cm at 480. These depths generally define regions wherein important vibration sources may be located as follows: (0.0 to 2.0) cm void of sources, (2.0 to 4,0) cm left coronary artery (LCA) and left circumflex artery (LCX), (4.0 to 5.0 cm) overlap (?) and (greater than 5.0 cm) valves with flow during the diastolic interval (M and T). The loci of coronary arteries are illustrated with dashed lines because they are not necessarily entirely in the same plane as the cross-section depicting the valves. The size and distance metrics in FIG. 4 are typical of an adult male and the relative locations of valves are generally correct for discussion purposes. The anterior left coronary artery (LCA) at 420, left circumflex (LCX) at 422 and at 424 the right coronary (RCA) arteries are illustrated. In addition, the four heart valves are illustrated as follows: aortic at 402, the pulmonic at 404, the mitral at 406 and at 408 the tricospid valve. The xyz-coordinate system is illustrated with origin at 456.

In FIG. 4, while the pulmonic (P) valve 404 is in the same z-axis depth range from the x-axis as the LCA and LCX, unless there is P valve regurgitation during the diastolic interval (DI), there should be minimal P valve vibration. Similarly, for the aortic (A) valve. However, during the DI there is ventricular refilling with substantial flow through the mitral (M) valve. If the M valve is defective, then turbulence beyond the normal "healthy" valve flow sound is likely. Accordingly, a "healthy" baseline reference is important and in the present analysis human data Case 021813 is adopted as a standard noise floor reference (SNF) for illustration, with no limitation implied thereby. Moreover, a priori knowledge regarding the spectral signature and range indicators for the M valve DI vibration is important. This a priori knowledge is used in one or more embodiments to allow classification by distinguishing coronary artery turbulence induced vibration from defective M valve vibration. Note that because heart valves and arteries can be in the same depth range from the sensor array, as described above, an "overlap ambiguous region" necessarily exists. This overlap region must be considered when analyzing localization results. A nominal overlap region is indicated with the "?" symbol on FIGS. 12B, FIG. 17, FIG. 18, and FIG. 26 below. This nominal overlap region corresponds with the area bounded by the 4.0 cm and 5.0 cm depth indicators in FIG. 4. It is understood that the overlap region varies between humans and the overlap regions presented herein are provided merely for illustration and do not limit embodiments of the invention. It is important to utilize echocardiographic imaging to establish the unique heart surface orientations for each human subject analysis because use of such images can be of assistance with the interpretation of vibrational cardiac data and the use can improve an estimation of a state of health of a human.

Corresponding to a block 304 (FIG. 3), the vibrational cardiac data that is extracted during the identical synchronized time interval for all N sensor channels, can be further partitioned into subintervals or slots as described above. Referring back to FIG. 2, the diastolic window 212 is divided into four 4 slots 214 and the next diastolic window 232 is partitioned into four (4) slots 234. Adjacent time slots with the slots 214 or 234 can overlap in time. The slots have fixed starting times within the diastolic interval and are typically separated by less than one tenth of an average heart cycle (for example, 0.1 seconds for a 60 beat per minute heart cycle). In one embodiment, the length of the slot interval, in number of time samples, is taken to be the number of points in a discrete Fast Fourier Transform (FFT) operation that is performed independently within each slot. This procedure effectively strobes the same time slot number (e.g. 1.2, 3, 4, etc.) from each heart cycle for FFT spectrum analysis. In various embodiments, the temporal length of an FFT window slot is in the range of 0.15+0.1 seconds. Thus, for each sensor channel, a complex Fourier spectrum of the vibrational cardiac data is computed from the time series data acquired in the corresponding time interval. Alternatively, with enough processing power, in a suitably configured data processing system, the entire heart cycle is processed, thereby making the time interval equal to the duration of the heart cycle. Note that in this description of embodiments, certain techniques are described that transform a signal from the time domain to the frequency domain, such as a discrete Fast Fourier Transform (FFT). Such techniques are given by way of example and do not limit embodiments of the invention. Other functionally equivalent processes to the FFT can be used to create the complex Fourier spectrum of the vibrational cardiac data.

Heart Valves

In some situations, as illustrated in FIG. 1A at 150, cardiovascular disease progresses with a deterioration of valve function that can result from, for example, calcification of one or more heart valves. During calcification of a heart valve, the elasticity of parts of the heart valve changes. The changes are often marked by an increase in stiffness due to the calcification process. Changes in the valve surface also result from the deposition of calcium within parts of the heart valve. For example, once flexible, smooth and straight valve surfaces can take on a more rigid curvature(s) not present before calcification. These changes in the structure of the heart valve, e.g., new curvatures in the surface(s) of the valve leaflets, changes in stiffness of the valve structures can contribute to creating turbulent blood flow where the flow was previously either laminar or substantially laminar. Similar to the condition of blood flow turbulence caused by a lesion formed on the interior of the artery wall, a condition of blood flow turbulence can exist that is caused by the calcification and reduced cross-section of a heart valve. In such cases, the calcification of the heart valve gives rise to increased curvature of the surface(s) of the valve and supporting structures that were not formerly present. The curvature, flow restriction and high valve flow velocity produce turbulence in the blood flow. The turbulence in the blood flow presents a fluctuating pressure field to the heart structure wherein a source of vibrational energy excites the heart and propagates therefrom. This vibration field propagates throughout the human's body and can be sensed non-invasively on the surface of the human, such as on the chest proximal to the heart.

Heart valves are located within the chambers of the heart. In particular, as discussed in conjunction with FIG. 4, and the mitral and tricuspid valves are located somewhat deeper than coronary arteries that are in and on the heart chamber walls. Thus, valves and coronary arteries are separated in space residing at different distances from the surface of the chest. During the diastolic interval (DI), the separation of coronary arteries and valves in space can allow sources of blood flow turbulence to be distinguished by localizing a source with coordinates, e.g., $x_1$, $y_1$, $z_1$, from another source localization with coordinates, e.g., $x_2$, $y_2$, $z_2$, which when separated in space are thus distinguishable one from the other as flow induced vibration. Thus, it is desirable to be able to locate, within the volume of the body, a source of blood flow turbulence in order to separate a valve origin from an artery origin thereby furthering the evaluation of a human's cardiovascular system. For example, during the DI, blood flow in the coronary arteries occurs at the maximum velocity and, therefore, if turbulence occurs, then vibration can be induced. Concurrently, there is high velocity atrio-ventricular blood flow through both the mitral and tricuspid valves during the rapid refilling of the ventricular chambers during the rapid refilling, diastolic phase of the heart cycle. The depth of the left anterior descending (LAD) coronary artery would be less than the depth of the mitral valve. However, the upper left main artery (LMA) could have a depth that would coincide with a depth of the mitral valve. In this case the spectral signature and possibly the vertical z-axis location would be critical for classification. Such information is used to provide a diagnosis as to whether pathology exists within a human's cardiovascular system. The determination as to whether either a heart valve is incompetent or an artery is suffering from an occlusion is obtained through various embodiments of the invention, Localization Overview The N sensor array, described in FIG. 5 at 500, is used to measure and process vibrational cardiac energy, which is measured at a body skin surface defined in the coordinate system with origin in FIG. 1A at 142 and FIG. 5 at 522. The coordinate system defines the positive x-axis at 513, positive y-axis at 511 and positive z-axis at 515. In one embodiment, such measurement and processing of the vibrational cardiac energy is used to determine whether a plaque deposit(s) (coronary artery lesion(s)) 508 exists in the human due to coronary artery disease (CAD). In other embodiments, such processing can be used to DLC vibrational energy generated within the human in general and not necessarily caused by coronary artery disease. For example, airflow through congested passageways may induce contiguous tissue vibration. Turbulent blood flow over the leaflets of a heart valve may induce tissue vibration.

Noninvasive determination of the location of a source of turbulent blood flow induced vibration within a person's chest requires the use of three or more displaced sensors (sensors separated spatially) mounted on the surface of the person's chest. These sensors are typically mounted on a surface of the person's chest as described in conjunction with the figures noted above. In addition, a description of mounting an array of vibrational cardiac sensors is also provided in conjunction with FIG. 5. Note that as described in conjunction with the figures above, the sensors can be of the non-contact variety e.g., laser. For illustration, and without any limitation implied thereby, the following description of embodiments uses contact sensors as a non-limiting example.

FIG. 5 illustrates, generally at 500, a conformal array of N vibration sensors such as at 516 mounted on a surface of a person, according to embodiments of the invention. With reference to FIG. 5, a Cartesian coordinate system with origin at 522 is indicated by the x-axis at 513, y-axis at 511, and z-axis at 515 pointing into the thorax at a point over the heart. In other embodiments, different coordinate systems can be used. The example provided herein using a Cartesian coordinate system is given merely for illustration and does not limit embodiments of the invention to a Cartesian coordinate system. Clearly, either a radial or spherical coordinate system could have advantages. In FIG. 5, the x-axis (horizontally oriented with respect to a standing person) of the array is positioned over an intercostal space at 515, i.e., a space between adjacent ribs is indicated. The y-axis 511 is approximately parallel to the sternum (vertically oriented with respect to the standing person). The z-axis at 515 is positive into the chest and nominally perpendicular to the anterior (nearer the front) heart surface.

In various embodiments, the sensor array in FIG. 5 at 522 and 516 is a conformal array that can be constructed of three (N=3) or more sensors. As the array conforms to the person's chest during application thereto the array follows a curve in space as defined by the surface of the chest. Thus, each element of the array has three coordinates in a 3-dimensional space associated therewith. A general n-th sensor indicated as A, at 520 has coordinates $x_n$, $y_n$, and $z_n$ along the three mutually orthogonal axis 513 ($x$), 511 ($y$), and 515 ($z$).

A coronary artery is represented at 502 and a flow of blood therein is indicated at 504. A source of vibrational wave energy in the coronary artery 502 is indicated at 506, 508 and 510. Similarly, the source of vibrational wave energy 548 could be from blood flow turbulence induced by a defective mitral valve, such as a valve that has experienced calcification as described above. Thus, the source of vibrational wave energy 546 is used to generically represent an instance of pathology within the person's cardiovascular system that causes vibrational wave energy. Following the methods and systems described below techniques are described as a methodology intended to identify whether the source of vibrational wave energy is arising from a heart valve or from a coronary artery.

In operation, the three or more sensors are connected to a vibrational cardiac data acquisition system (for example, FIG. 1A at 126) and are used to acquire vibrational cardiac signal data, which are stored and processed to obtain the vibrational frequency "signature" and location(s) of the source(s) of the blood flow turbulence within the person's body. Data received by the sensors is processed to estimate the relative time delay differences of the vibrational wavefront that is propagating from the source (within the person's chest) to and across the multiple sensors within the array. Localization of the source of the vibrational cardiac data measured by the array can be accomplished by processing the vibrational cardiac data using several methods.

One method for processing the vibrational cardiac data is referred to as triangularization. In triangularization, the sensor array is divided into two parts; a first part referred to hereinafter as a "first half" (although the first part or first half need not be exactly one-half of the whole array) and a second part referred to herein as a "second half." The second part referred to hereinafter at times as the "second half" need not be exactly one-half of the whole. Each "half" is used to estimate the wavefront angles of arrival relative to the geometric centerlines of the two halves and the source location is estimated by cross-fixing the arrival angles. The triangle defined by the known baseline distance between the center of the first half array and the center of the second half array and the two source arrival angles are sufficient to define the source location at the intersection of the two remaining sides of the triangle. This method is referred to as triangularization and is used in various embodiments to obtain the location in space of a source of radiating vibrational energy. Note that in various embodiments, an array can be divided into two "halves" using the same number of elements or a different number of elements in each "half." In other embodiments, the array is divided into more than two parts wherein more than two angles are formed which permits more than one triangle to be used for the purpose of cross fixing during the triangulation process. Multiple locations obtained thereby can be averaged together to obtain the source location. In various embodiments, as few as three elements (sensors) can be used to obtain a location of a source of vibrational cardiac data. Embodiments of the invention are thereby flexible utilizing three or more sensors and are not limited to a particular number of sensors.

In various embodiments, useful location information is obtained from two sensors (N=2) that are used as an array of sensors. Such location information can produce only a bearing (angle) defined between a source and a line formed between the two sensors. A bearing can also be referred to as a direction relative to the array. Those of skill in the art will appreciate that a bearing from a distant source to a line array is the set of directions that form a cone having a conical angle. Thus, when two sensors are used to provide location information it will be understood that a bearing is implied thereby.

A more general method for processing the vibrational cardiac data is referred to as beamforming. Beamforming can be performed in various ways such as far field beamforming (non-focused in radial distance), focused beamforming (where the wavefront is assumed to have a source at a center of curvature). Compared to partitioning the sensor array as in triangularization, using all the sensors simultaneously to estimate the curvature of the source-generated wavefront yields superior results. Focused beamforming has both more detection sensitivity and the ability to accommodate multiple vibration sources. In this method, the array of sensors at 516, An: n=1, 2, . . . , N at 520, is scanned, usually with digital time delay techniques, through the entire range of both arrival angles and radial distance from an origin at 522 within the focusing range of the sensor array's spatial aperture. When the angle of arrival and radial distance that correspond most closely to the true source location is "interrogated" by the scanning process, the summation of all the sensor outputs of the focused beamformer registers a maximum value that is proportional to the strength of the radiating source energy at the focus point. As used in this description of embodiments, before the beamforming summation function, conventional focused beamforming, "CBF," sets either the time delays or corresponding phase shifts required when the array of sensors is focused at a particular point in space. The CSDM is either computed for synchronized time increments spanning the entire heart cycle, based on averaging all heart cycles in the entire heart waveform or it can optionally be computed for specific time slot numbers in the heart cycle. In either case, the CSDM is computed by placing the complex Fourier spectrum (FFT outputs), obtained by processing the transducer channel outputs, into a four-dimensional matrix indexed as x (n, b, k, m):

$$x(b, k, m) = \begin{bmatrix} x(1, b, k, m) \\ x(2, b, k, m) \\ . \\ . \\ . \\ x(N, b, k, m) \end{bmatrix}$$

where n is the vibration transducer number, k is the Fourier transform discrete frequency bin number, b is the heart beat count in the acquired ensemble of heart cycles, and m is the slot number. In cases where a heart cycle waveform contains multiple segments, the heart beat count b will span a concatenation multiple heart cycle segments, where each segment corresponds to a breath holding period and slot-by-slot parsing intervals as described above.

With N as the number of vibration transducer channels, the CSDM is then an N-by-N complex Hermitian R (k, m) matrix. R (k, m) is calculated as a time average over the heart beat ensemble count index b, separately for each frequency bin k, and slot number m, with ij-th element:

$$R_{ij}(k, m) = (1/B) \sum_{b=1}^{B} x(i, b, k, m) x(j, b, k, m)^*,$$

where the symbol "*" indicates complex conjugation, B is the number of heart beat cycles in the ensemble which can span multiple segments of acquired vibrational transducer data in some embodiments. The value of B will depend on the number of separate transducer channels processed for a given measurement. Generally, a lower bound for the value of B is approximately four (4) times the number of transducers, N. A preferred value for B is eight (8) to ten (10) times N. Those of skill in the art will recognize that the goal in selecting the value for B is to reduce the statistical variance in the estimation of the smaller eigenvalues of the estimated CSDM matrix, therefore the value of B can be set at various numbers that are illustrative and not limiting.

The terms "gross (-channel) spectral density matrix (CSDM)" in various forms and "cross-spectral density matrix (CSDM)" are used synonymously herein. Moreover, there are temporal fictional versions of the CSDM referred to as the sensor array cross-correlation matrix. In various embodiments, the CBF processing is performed within a "portion" of a portion of a heart cycle and within one or more vernier bands (VBs) of frequency in each slot where the VB is established by identifying a feature in the power spectral density (PSD) estimate of one or more channels of the array. Placement of a VB marker around a feature is described further below in conjunction with the figures that follow. In other embodiments, conventional beamformer (CBF) processing is performed on a bandwidth that is larger than a bandwidth of a feature. A non-limiting example of such a larger bandwidth, given merely for illustration with no limitation implied thereby, is the bandwidth of 150 Hz to 1 kHz. The frequency range below 150 Hz exhibits wavelengths that are too large for accurate localization and, likewise, in the frequency range above 1000 Hz, the dispersive elastic medium wave speed has variability that may limit the use of a universal wave speed for all patients.

Within the category of beamforming is adaptive beamforming (ABF), and within the category of adaptive beamforming is adaptive focused beamforming. Also, within the category of ABF is ABF using principal components of the CSDM to either simplify the computational burden and/or to exploit any of a large number of enhanced spatial resolution algorithms. Before the beamforming summation function, ABF selects the same focusing time delays as the CBF process but also digitally filters the individual sensor signals before the summation of all the sensors is performed. The criterion for designing the ABF filters is to reduce the effect of source interference when wavefronts from vibrating sources at locations other than the focal point are present simultaneously with the assumed focal point source. Note that the use of beamforming and spectrum estimation techniques subsequent to spectrum analysis and the identification of frequency bands, referred to as vernier bands (VBs), for frequency selective application of localization methodology is taught herein. In particular, sensor channel and ensemble averaged PSD estimates increase signal-to-noise ratio, thereby enhancing the detection of CAD and valve incompetence. Use of the PSD for detection of CAD and valve incompetence and accurate classification of the vibration source requires both post (spectrum) analysis of the PSD signature and localization (PAL) of the estimated vibration source.

The algorithms used herein to perform ABF processing without vernier band pre-selection are discussed in U.S. Pat. No. 5,727,561 (Owsley) (see equations (12), (13), (14), and (15)) where conventional image "e" corresponds with image volumes presented herein that are labeled as "CBF" and minimum variance image "m" corresponds with image volumes presented herein that are labeled as "ABF". U.S. Pat. No. 5,727,561 is hereby incorporated by reference. The algorithms from U.S. Pat. No. 5,727,561 are applied to a cross-spectral density matrix (CSDM) formed as described above and accompanying description of forming a CSDM from a plurality of sensor channels by averaging an ensemble of heart cycles, etc. In various embodiments, the ABF processing is performed within a synchronized portion of a plurality of heart cycles over a vernier band (VB) of frequency where the VB is established by identifying in a post spectrum analysis step the features in the power spectral density (PSD) estimate of one or more channels of the array. Placement of a vernier band (VB) on a feature is described further below in conjunction with the figures that follow. In other embodiments, ABF processing is performed on a bandwidth that is larger than a bandwidth of a feature. A non-limiting example of such a larger bandwidth, given merely for illustration with no limitation implied thereby, is the bandwidth of 150 Hz to 1 kHz. Another example of VB selection is in a portion of the PSD spectrum wherein the spectrum level is higher than a baseline for "normal."

Another process for beamforming is Principal Component (PC) adaptive beam forming, a subset of ABF. PC ABF is a method for reducing the computational load of the ABF implementation by using a minimally complex, principal component representation of the matrix of inter-sensor correlation values (CSDM) that is central to the ABF implementation. In some cases, enhanced PC ABF also can be exploited to achieve higher spatial resolution.

Application of a localization algorithm e.g., triangularization, CBF, ABF, etc. to a propagating wavefront with a spatial array of sensors requires a mathematical model of the propagation medium. In particular, an average speed of propagation of the elastic wave energy in the inhomogeneous medium is required and a form for the variation of the speed of propagation of the wave energy within the medium is required. The mathematical model does not have to be exact for useful information regarding the approximate location of a source of the propagating energy to be obtained. Moderate mismatch in the model of the medium can produce commensurate moderate degradation of the source location accuracy and still allow a critical assessment of general source location and spatial distribution. For example, this nominal source location capability can help to resolve uncertainty between the vibration of either an anterior coronary artery or a heart chamber wall provided a well-defined set of a priori rules based on established heart morphology is consistently applied. This resolution can be accomplished because beamforming can present estimates of both depth into the chest and angular location of the vibration source. In some cases, it may be desirable to distinguish between vibrations emanating from within an artery in the epicardial wall (the inner serous layer of the pericardium, lying directly upon the heart) from those originating internal to the heart at a heart valve location, such as a location for a mitral and/or tricuspid valve during the diastolic interval (DI). Moreover, the use of an ancillary measurement, such as for example, anterior echocardiographic image data, acquired at the same location as the vibration sensor array and merged or fused with the beamforming scan results, can be complementary during this procedure by providing location information by physical means that are independent from the vibration sensor array. Such use of ancillary measurements are described more fully below in conjunction with FIG. 33.

In the case of vibrational cardiac data caused by turbulent blood flow pressure fluctuations on an artery wall, as discussed herein, the speed of propagation of the vibration wave energy is in the range 3 to 8 meters/second which is the order of the shear wave speed in human tissue within the 100 to 500 Hz frequency band. For the beamforming calculations performed in support of this description of embodiments an assumption can be made that the medium (the human's heart and chest) is homogenous in terms of an average wave propagation speed. In other embodiments, this assumption need not be made. For example, in other embodiments, the anisotropy of the medium can be taken into account in some approaches using in situ measurements with, for example, ultrasound probing to map the thorax subsurface. The degree of mathematical modeling applied to the medium does not limit embodiments of the invention and the accuracy of the inhomogeneous wave speed mapping throughout an imaging volume should always be sought to the maximum extent. The examples presented herein using an assumption of a homogenous medium are provided merely for illustration. Other mathematical representations of the medium such as anisotropic wave speed mapping are contemplated within the disclosed embodiments of the invention.

The speed of propagation of elastic wave energy propagating from an occlusion in an artery was obtained from experiments conducted on a human tissue simulation using a porcine tissue surrogate and a simulated partially occluded artery as the source of simulated blood flow turbulence induced vibration. FIG. 6 illustrates, generally at 600, an elastic wave measurement apparatus, according to embodiments of the invention. With respect to FIG. 6 at 600, the elastic wave measurement apparatus consists of a blood flow simulation phantom that uses a glycol-water solution with blood-like viscosity and a porcine tissue specimen phantom with a nominal thickness of 3.75 cm. A latex tube artery simulator at 608 with a 6 mm inner diameter was fitted with a radially symmetric occluder having a seventy-five percent restriction by cross-sectional area. The latex tube at 608 was placed under the porcine tissue specimen at 602, shown wrapped in elastic stretch wrap, and an array of piezo-elastic sensors 604 with an 8 cm total aperture was placed on top of the porcine slab 602. The elastic wave measurement apparatus included placing the porcine tissue specimen 602 on top of a silicone gel base 606. The apparatus, so constructed, is meant to simulate elastic wave propagation in a human body. The elastic wave is generated using a machined occlusion, occluder, placed in the latex tube coronary artery simulator 608. Increased flow velocity through the occluder produces downstream, i.e. distal, turbulence that, in turn, induces tube wall vibration.

In the present case, the occlusion in the latex tube 608 is placed at a known location relative to the transducer array 604. The problem is now one of selecting an average wave propagation velocity for use by the beamforming algorithm that permits the beamforming algorithm to produce as a localization output, coordinates that match the known location of the turbulence in the latex tube 608. The process proceeds using a CBF focused beamformer operating over a 12 Hz wide vernier band (VB). This VB was moved incrementally from 150 Hz to 450 Hz in nominal steps of 25 Hz. At each frequency operating point, the wave-speed parameter in the CBF algorithm was adjusted until the beamformer focused on the known location coordinates with a tissue depth of the source at 3.75 cm. The wave speed that gave the correct, i.e. true location for this "inverse beamforming" search process was entered into the empirical dispersion curve table (data 706 in FIG. 7). In this manner, a dispersion curve 706 valid below 500 Hz for human applications of both CBF and ABF imaging is obtained. FIG. 7 compares the wave speed determined experimentally using inverse beamforming with the analytical result given by J. Verberg, (see J. Verberg, "Transmission of vibrations of the heart to the chest wall," in Advanced Cardiovascular Physiology, vol. 5 pt. III. Basel, Switzerland: Karger 1983, pp. 84-103). The Verberg dispersion curve can be utilized for PAL imaging between 500 and 1000 Hz FIG. 7 illustrates, generally at 700, elastic wave speed data acquired from the apparatus of FIG. 6. With respect to FIG. 7, the wave speeds determined experimentally using inverse beamforming are plotted at 706 with wave speed on the vertical axis at 704 as a function of frequency on the horizontal axis 702. Also plotted at 708 are theoretical results for wave propagation speeds determined according to the analytical result given by Verberg.

Accordingly, localizing a source(s) of vibrational cardiac energy is performed in various embodiments using any one or more of the techniques which are available for localizing a source(s) of field energy resulting in vibrational cardiac data collected noninvasively from a surface of a human using either three or more sensors or three or more groups of sensors within a vernier band of frequency. In the following description of embodiments, results are presented and discussed for the CBF and the ABF processes of localization. No limitation is applied thereby, and embodiments of the invention can be practiced using any method of localization including user defined methods of localization, etc. using vernier bands, VBs, of frequency identified in an examination of the PSD estimate.

In view of the foregoing discussion, the application of CBF and ABF focused beamforming to the anterior and lateral arteries of the heart is graphically illustrated in FIG. 5. In various embodiments, an example of post (-spectrum) analysis localization (PAL) proceeds using the wave speed data from FIG. 7 together with the CBF and ABF algorithms to scan a volume of a person's chest (an imaging volume) in a search for vibration intensity maxima, i.e. peaks, that indicate locations for occluded arteries or a heart valve suffering from impaired function. Conversely, the absence of an intensity threshold peak value(s) will indicate a healthy state of the cardiovascular system.

Volumetric Peak Search

An imaging volume, so obtained from beamforming an array of sensors focused within the human, is information dense often containing a plurality of information on different intensity levels which requires a display technique in order to convey a simplified summary view of what has been measured. The imaging volume is three-dimensional in nature as is evident from the fact that a coordinate system having three dimensions has been set forth in Figure S. Different techniques can be used to explore the imaging volume. In this embodiment, the display technique presented herein utilizes a peak-picking algorithm for searching the three-dimensional array of vibration intensity pixels produced by the scanned beamforming process.

Various implementations of a peak search algorithm can be employed to search for vibration intensity maxima within the imaging volume of the human. In various embodiments, vibration intensity maxima can be selected based on an algorithm(s) for defining a maximum at a point based on a comparison with values local to the point as described below. In other embodiments, vibrational intensity maxima are selected based on values that are relative to a reference according to a criterion. One such example is to select values as maxima that are above an offset from a noise floor reference. Another example is to select values as maxima that are within a range relative to a maximum value. While the examples that follow utilize an algorithm for selecting local maxima, no limitation is implied thereby, and such examples are given only for illustration. Referring back to FIG. 5, in one example, such intensity maxima are searched for using a 0.5×0.5×0.5 cm cubical element of the beamforming imaging volume as illustrated in the Cartesian coordinate system at 512. This pixel cube contains twenty-seven (3×9=27) intensity image pixels spaced uniformly at 0.25 cm. Other imaging pixel elements can be implemented instead of a pixel cube; this example using 27 image pixels defined in Cartesian coordinates is used for illustration and does not limit embodiments of the invention. For example, a spherical coordinate system can be used wherein the imaging cube would be transformed to an imaging shell element with layers of the shell at constant radii from the origin. The 27-pixel cube is digitally scanned through the desired imaging volume. A beamforming focus point pixel is located at the corner of each of the eight 0.25×0.25×0.25 cm sub-cubes contained in the 3-by-3-by 3 (node) scanned pixel cube.

In this embodiment, the CBF-ABF imaging volume is defined within the three-dimensional xyz coordinate system, where the x-axis ranges from −4.0 cm to 5.0 cm. The x-axis is placed over an intercostal space (horizontal direction), the y-axis ranging from −4.5 cm to 4.5 cm is nominally parallel to the sternum (vertical orientation) and the z-axis ranges from 2 cm to 11.0 cm in depth. The positive z-axis is into the chest (nominally perpendicular to the anterior heart surface). The result of scanning the image volume and processing the vibrational cardiac data through the CBF and ABF algorithms is a volumetric vibration intensity image volume measurement (referred to subsequently as VVI data). When the sensor array is located on the chest of the human subject, the VVI data contains the "artery region" on both the anterior left lateral surfaces of the heart and the "valve region" on either deep (large z value), or to the right (positive x value) and/or the top (positive y value) of the heart. The imaged volume is resolved to 0.25 cm as the pixel cube is scanned throughout the imaging volume. In other embodiments, or with other arrays of sensors, different spatial resolutions are obtained. The 0.25 cm pixel resolution is described here merely for illustration and does not limit embodiments of the invention. The sensor array can also be placed on the upper region of a human's back or on a side with the objective of PAL processing the posterior heart and lateral heart respectively.

In one or more embodiments, the frequency range over which the VVI data is computed is established from the features extracted from the power spectral density (PSD) estimate of the channel vibrational cardiac data. Features e.g. spectral peaks, plateaus, swaths, etc., are described more fully in U.S. Pat. No. 9,591,972 to Owsley et. al. titled "System and Method for Evaluating a State of Health of a Coronary Artery." U.S. Pat. No. 9,591,972 is hereby incorporated by reference. Features are extracted by using feature parameters such as estimated center frequency (CF), bandwidth (BW), signal to noise ratio (SNR) parameters of the feature, etc. In some embodiments, system logic is designed to select a Vernier Band (VB) "of interest" from the PSD signatures that contain spectral peaks or other features that would be typical indicators of turbulent blood flow induced vibration in either an occluded artery or an incompetent valve. Either elevated spectrum level relative to the local background over frequency band limited portions of the spectrum or elevated spectrum level over large portions of the spectrum relative to the normal baseline would prompt the assignment of a vernier band (VB) for localization. As the pixel cube is scanned through the imaging volume, the estimated vibration energy intensity at the center of the 3×3×3 pixel cube is compared with the twenty-six pixel intensities surrounding it and is declared to be a pixel intensity "local" maximum if this intensity value is greater than any of its surrounding twenty-six pixel intensity values. The xyz location and intensity of all the local intensity "peaks" is recorded for display using perpendicular viewing angles of the entire imaging volume observed from directions normal to the xz and yz planes. This "peak-picking" display can be envisioned as a "fish tank" with the local peak values submerged in a transparent tank with rectangular sides that can be viewed simultaneously from the front and side. Note that a "local maximum" can be defined by other algorithms and such definition of a local maximum is not limited to the examples provided herein.

In the VVI image data presented below, the results of processing a VVI image volume as described directly above records all of the local peaks detected inside the volume for a VB. In the embodiment disclosed herein, in order to display these peak localizations, the numerical intensity values are first rank ordered and the median of this ordered list is obtained. The location of the maximum, i.e. global peak, intensity value in the list is plotted with a square, "D." The locations of peaks with intensity values greater than the median but less than the maximum the locations are plotted with a ">." The location of the minimum intensity value in the rank ordered list is plotted with a circle, "o." The locations of the local peak intensity values greater than the minimum but less than the median are plotted with a "<." Thus, by comparing the locations of the symbols 0, <, >, and O against a priori knowledge of relative depths of cardiovascular structures of interest, i.e., artery and valve a state of health of a human's cardiovascular system can be estimated as a function of blood flow turbulence induced vibration. For aid in understanding this description of embodiments, a z-axis on the xz and yz-viewing planes presented below is labeled with "artery region" and "valve region" to facilitate the description. In practice, the results of analyzing the imaging volume are compared using a cardiac data processing system to determine whether local maxima are within an expected depth of a cardiovascular component of interest, such as an artery or heart valve chamber wall.

For classification of a power spectral density (PSD) VB feature, the selection of a vernier frequency band (VB) for source localization from the PSD estimate of an average channel can be performed either by an analyst using a graphical user interface (GUI) or by utilizing a logic block implemented via a cardiac data processing system. An automated process can be embodied for extracting parameters of a feature such as the estimated center frequency (CF), bandwidth (BW), signal to (background) noise ratio, SNR, parameters of the feature. In the GUI and automated approaches, the estimated spectrum level (SL) and the SNR of the feature is used to weight the quality but not necessarily the criticality of the feature. As used in this description of embodiments, a SNR associated with energy detected at a particular location is used as a location quality metric. In various embodiments, for the purpose of illustration and with no limitation implied thereby, a typical value of minimum SNR that would be used to classify a VB feature as clinically significant could be in the range of 3 to 6 decibels (dB). This minimum SNR significance threshold is not to be considered as restrictive and can be based on the goal to maximize diagnosis sensitivity and specificity. To illustrate this point, a human test example involving a PSD feature with only a moderate SL but a critical localization outcome is presented in some of the following figures. In PAL processing, the criticality of a feature in a PSD estimate for occlusive coronary artery and valve incompetence screening is primarily determined by the combination of VB feature parameters and spatial source location. In some instances of evaluating a person's state of cardiovascular health, it is the vibrational source localization process alone that may distinguish a true source of coronary artery turbulence (an occluded artery) from a valve flow turbulence source. In some embodiments, the minimum SNR is less than 3 dB, in yet other embodiments it is more than 6 dB. Accordingly, when reference is made to a 6-decibel (dB) clinical significance threshold in this description of embodiments, no limitation is implied thereby and reference to a value associated with such a threshold in these instances is made merely for illustration. In light of the foregoing, a metric of clinical significance (MCS) is calculated using a strength of a vibrational energy estimate of a feature associated with a given location and a clinical significance threshold. The strength of the vibrational energy estimate is based on a magnitude of the vibrational energy estimate relative to a background noise estimate (thus the strength can be expressed as a signal-to-noise ratio (SNR)). The calculated MCS or SNR is then compared to the clinical significance threshold to establish a significance of the MCS to a diagnosis related to cardiovascular disease. The MCS establishes the specificity and sensitivity of the method relative to cardiovascular disease, Beginning with FIG. 8 generally at 800, the post (spectrum) analysis localization (PAL) process is illustrated with human data. In one embodiment, PAL begins with the selection of a processing time interval within an ensemble of heart cycle recorded data as indicated by the designation of four overlapping time slots at 814 within the interval at 806. The process continues with the identification of a feature of interest in the ensemble PSD and proceeds to localization of a source of vibrational cardiac energy using a scanning focused beamforming operation limited to the VB bandwidth of the feature. The PAL process concludes with an assessment of the estimated PSD parameters and vibration source localization to formulate a clinical classification of the patient's condition and to further inform the clinician's diagnosis.

Human Data

Normal Baseline: Case 021813

In one or more embodiments, the PAL methodology presented herein is first applied to the analysis of two measurements from the same individual for which vibrational cardiac data was acquired on Feb. 18, 2013 (Case 021813) and then again on Nov. 21, 2015 (Case 112115). At the time of the data acquisition for Case 021813, the subject had no risk factors for heart disease unrelated to family history and benefited from a rigorous exercise program. As illustrated below, PAL processing of Case 021813 confirms the absence of significant energy from blood flow turbulence. Thirty-three months later, in Case 112115, the subject had been diagnosed by independent echocardiographic testing with moderate calcification of the mitral valve. At the time of the calcified mitral valve diagnosis there was no attempt to diagnose arterial disease with angiography. The PAL processing described below for Case 112115 localized features that are likely to have been caused by blood flow turbulence resulting from either a defective heart valve and/or from a partially occluded coronary artery(s). Other aspects relating to the cardiovascular health of the subject are described in conjunction with the figures that follow.

FIG. 8 illustrates, generally at 800, an ensemble of Case 021813 heart cycles, amplitude time series plots of vibrational cardiac data acquired from a human whose coronary arteries are in a healthy condition, according to embodiments of the invention and as described above. With reference to FIG. 8, one-hundred (100) synchronized heart cycles from the ensemble of vibrational data that are over plotted in a "stack." In FIG. 8, the horizontal axis 816 represents time and the vertical axis 802 represents the amplitude of the vibrational cardiac data signal. The ensemble of heart cycles was collected as described in conjunction with the figures above during breath-bold periods by the subject. The vibrational cardiac data processing system cross-correlates the heart cycles with a high-quality master single heart cycle replica (selected from the ensemble) to parse and time align the ensemble of heart cycles as described above. In the case of FIG. 8, the ensemble was time aligned, i.e. synchronized to the time point corresponding to the peak of the S1 valve closure interval. The S1 valve heart sound interval is indicated at 804. Other points in the ensemble of FIG. 8 can be used as the point for time alignment such as for example the peak of the S2 interval at 824. Heart cycles are pruned as required to eliminate unwanted sources of noise arising from various sources such as digestive system and respiratory noise. The diastolic interval (DI) or "diastole" as labeled in FIG. 8 is generally identified at 810a and 810b. At least a portion of the diastolic interval at 810a is identified for further PAL processing. Such portions are indicated at 814 as Slot 1, 2, 3, and 4. In this embodiment, the portions indicated as slots are shown to overlap by 50-percent in time. In other embodiments, such portions (slots) either do not overlap in time or overlap to a greater or lesser extent than 50-percent. In some embodiments, only one slot is used. In yet other embodiments, a portion of the diastolic interval (slot) is selected such that there is no S1 and S2 valve closure energy within the time interval set by the window at 812a. In yet other embodiments, a portion of the diastolic interval is selected such that some valve closure energy (such as 814 slot 4) is captured within a time interval set by the window and the interval may, in fact, be inclusive of the entire heart cycle. Slot 4 in 814 is an example of a portion of the diastolic window 810 that includes vibrational energy transmitted from the beginning of the next valve closure peak S1 at 803a. The increase in time spread between the two S1 intervals at 803a to 803b is a result of natural variability in heart rate over the two minutes of breath holding required to acquire 100 heart cycles. The acquisition interval defined by 814 is adjacent to the S1 synchronization point and, therefore, exhibits minimal time variability.

FIG. 9 illustrates, generally at 900, the sequence of operations for the "input-process-output" (IPO) to obtain the slot-by-slot ensemble averaged power spectral density (PSD) estimates. For each of B heart cycles represented in frequency and time at 902 in the ensemble, the time sampled data is acquired for each slot sequentially at 910 and a time-to-frequency Fast Fourier Transform FFT operation is performed separately for each slot. The FFT window and the slot length are identical in this embodiment. At 912, eight adjacent FFT bins (m, m+1, . . . , m+7) are illustrated on the vertical axis at 906. On the horizontal axis at 908 is the ensemble time with the synchronized traces of a transient vibration with a time varying instantaneous frequency versus time trajectory for B heart cycles at 902. A slight variation in the frequency-time trajectory between individual heart cycles is represented to allow for the natural variability in heart rate and vibration waveform observed in vivo. In each time slot the FFT output is power detected by averaging the FFT output amplitude in each time slot over the entire ensemble to produce the power spectral density (PSD) estimates for each time slot at 960. One embodiment of the digital signal processing of the ensemble is presented as a discrete (Fast) Fourier Transform (FFT) implemented within four (4) overlapping intervals referred to as time slots at 910. Any appropriate frequency-time decomposition method that preserves sensor-to-sensor time delay information for transient signals can be used. The discrete Fourier transform frequency resolution cells from bin m to bin (m+7) are represented at 912. An example of an indexing scheme to reference a particular time slot and FFT frequency bin is shown at 914 at time slot 3 and frequency bin m+6 as (3, m+6). The example at 0914 shows a two-dimensional index pointing to time slot three (3) and FFT frequency bin (m+6). Accordingly, this address indexing scheme refers first to a time interval slot (s=1, 2, 3, 4) and, second, to a discrete FFT frequency bin location (f=1, 2, . . . , m, m+1, m+2, . . . , $N_{FFT}$), for the fore-mentioned specified time slot. The integer, NET, is the number of time samples in the FFT duration interval, which in this embodiment, is also the number of time samples in the slot interval. For each index pair, (s, f), an estimate of the cross-spectral density matrix (CSDM) for the array of vibration sensors is obtained by averaging over the ensemble of B recorded, parsed and synchronized heart cycles. The CSDM estimate captures the average phase differences. i.e. relative time differences, between all sensor pairs in the array and this information, in turn, is used by the localization and/or beamforming processes to estimate the location of a vibration source.

On the right side of FIG. 9 at 960 is an illustrative graphic of the Power Spectral Density (PSD) estimate that would be derived from heart cycle ensemble averaging the Fourier transform individually within each of the four time slots. The spectrum level, in the four PSD estimates, is a measure of the cumulative ensemble averaged signal energy in each FFT frequency bin for the duration of the specified time slot. The progression of the signal energy through the slots with slot number is an indicator of the combined dwell time of the translating frequency in a particular PSD frequency (bin)-slot (interval) resolution cell. Also, the ij-th element in the CSDM is an ensemble averaged "snapshot" of the spectral coherence amplitude and phase difference between all pairs of sensor channels (i=1, 2, . . . , N; j=1, 2, . . . . N) that is the basis for spatial scanning of the imaged, localization volume.

FIG. 10 at 1000 presents an overlay of time averaged vibrational frequency power spectral density (PSD) ensemble averaged estimates corresponding to the Case 021813 ensemble data from FIG. 8. These overlap PSD correspond to FIG. 9 at 960 according to embodiments of the invention and the procedure of FIG. 9. With reference to FIG. 10, the power spectrum density estimates (PSD) have been plotted in the figure with frequency indicated along the horizontal axis at 1002 and estimated PSD absolute spectrum level in dB of the vibrational cardiac data signal along a vertical axis at 1004. A plotting key 1006 indicates the line type used for plotting the slot 1, slot 2, slot 3, and slot 4 PSD estimates. Plotting keys 1007 and 1008 indicate the line type used for a reference, i.e. "baseline" PSD that is designated as a "normal." The normal PSD selected is the Case 021813 Slot 2 PSD and is presented as the "standard noise floor (SNF)" without smoothing or the "standard noise floor (SNFsmth)" with spectral smoothing. In various embodiments, smoothing is accomplished with a sliding window that applies a smoothing function to the values that fall within the window. For example, a sliding window can perform an "average" of a number of values under the window and then replace a central value within the window with the "average" value of the window. In other embodiments, a sliding window as described above can be used in conjunction with a "median" value, thereby replacing a central value of the window with the "median" value of the window. Average value and median value smoothing are given by way of illustration and do not limit embodiments of the invention. At 1027 the low frequency (≤150 Hz) spectral energy from the M and P valve closures is encircled.

Generally, at 1000, FIG. 10 presents the Case 021813 power spectral density (PSD) estimates for the ensemble of the averaged sensor array channels in absolute spectrum level at 1004. For comparison purposes, normalization of the absolute spectrum level PSD by a desired reference PSD is of considerable utility. A PSD normalization can be performed several different ways in different embodiments. As an example of several ways, with no limitations implied thereby, a PSD normalization can be performed to either: (a) compare human data to a system noise input, or (b) compare a human PSD data set to a second human data set where the second human data set is acquired from an individual for example, with no indication of cardiovascular disease. In yet other embodiments, a PSD normalization can be based on multiple parameters such as by combining for example, (a) and (b) described above. As used in this description of embodiments, an example of a PSD measurement used in a type (a) normalization above could be performed with a file named "sensor system self-noise floor (SNF)" for example. As used in this description of embodiments, an example of a PSD measurement used in a type (b) normalization above is presented in the example illustrated with FIG. 10 through FIG. 12B herein. Case 021813 is classified as a normal standard adult male with respect to cardiovascular health. At 1100 in FIG. 11, the Case 021813 PSD set of FIG. 10 is represented but normalized first by the Case 021813 slot 2 PSD indicated at 1007, 1008 and 1106. The same PAL methods described using the normalized data can be applied as for the data that is not normalized. No information for PAL is destroyed by normalization. On the contrary, valuable comparative procedures accrue from normalization with respect to a SNF threshold.

Within FIG. 11, the normalized PSDs of the four diastolic time slots denoted in FIG. 8 are over-plotted. Over-plotting of the normalized slot PSDs facilitates a direct visual comparison of spectrum level and spectrum character by the analyst-reader between slots and relative to the baseline SNF. The comparison is helpful to understand a PAL PSD "feature" in a spectrum and to acquire the parameters of the feature for clinical classification. Four features (F1, F2, F3 and F4) in the normal baseline spectra of FIG. 11 are identified. The frequency windows of the features define vernier (frequency) bands (VBs) for PAL analysis and are indicated within rectangular boxes, such as F1 at 1110 (slot 1 indicated by thin solid line type), F2 at 1112 (slot 2 indicated by dotted line type), F3 at 1113 (slot 3 indicated by dash-dot line type) and F4 at 1114 (slot 4 indicated by thick solid line type). The width of a box indicates a bandwidth (BW) in frequency for the PAL Vernier Band (VB) analysis.

An alternate SNF measurement can be obtained with the cardiac vibration sensor array placed in an acoustically and electromagnetically quiet anechoic chamber calibration facility with no vibrational input to the sensors. The calibration facility reduces the ambient background noise field to a minimum and exposes the minimum residual noise (floor) of the vibration-sensing array of sensors. It is important to note that, when a human normal baseline PSD is used, the ambient SNF spectrum levels should be 10 dB or more beneath the actual human data PSD spectrum levels, This difference in amplitude relative to the system electronic noise floor ensures that the cardiac vibrational data acquisition system has measured vibrational energy originating in the human subject and is not picking up energy from either the instrumentation or ambient environment. This type of one-time system calibration noise floor PSD measurement is conducted to validate the sensitivity of a specific vibration sensor array but has no particular subsequent clinical utility as does a standard reference human noise floor SNF.

FIG. 12A contains the same four slot PSD plots as FIG. 11 except that these plots are contained in separate subplot PSD "breakouts" to facilitate readability when a large number of features are presented. The relative spectrum levels are shown on the vertical axes, at for example 1201 (Slot 1 plot) and frequency is plotted on the horizontal axes, at for example 1202 (Slot 1 plot). The normalized baseline spectrum level is shown at 1203 at a 0-dB level, this 0 dB level results from normalizing the Slot 2 data by itself, i.e., self-normalized. Note that the reference numerals 1201, 1202, and 1203 apply to each of the subplots in FIG. 12A, for Slot 1, Slot 2, Slot 3, and Slot 4. The normalized slot data plotted in FIG. 11 and in each of the sub-plots of FIG. 12A has been normalized by the PSD measurement shown in 1008 of FIG. 10, i.e., "SNFsmth dot: slot-2-021813-h-4-p-05." In various embodiments, other normalizations could have been created and presented, the normalization presented in FIG. 11 and FIG. 12A is presented for illustration only with no limitation thereby. A plotting legend in FIG. 11 indicates that VB feature F1 at 1110 occurs during time slot 1 which is the first designated time window after the S2 heart valve closure kinetic energy in the diastolic interval. Likewise, the FIG. 11 legend indicates that features F2, F3 and F4 occur in slots 2, 3 and 4 respectively. FIG. 12A also identifies the four features F1, F2, F3 and F4 at 1210, 1212, 1213 and 1214 respectively. In this embodiment, there are four such time slots used to partition diastole (810 FIG. 8) into equal length time segments that overlap by fiftypercent. These four time slots nominally span the early, early-mid, late-mid and late diastolic-early systolic interval. Note that it is possible to contain a late diastolic slot to contain the leading edge of the S1 heart valve energy peak (see FIG. 8 slot 4 at 814) and, therefore, can exhibit a higher low frequency spectrum level relative to slots 1, 2, 3 and 4. In the case of FIG. 8 the slot 4 PSD levels in FIGS. 10, 11 (thick line type) and 12A are up to 15 decibels higher in amplitude than the PSD amplitudes of slots 1, 2, and 3. This difference in vibrational energy illustrates the resolving power of various embodiments of the vibrational cardiac data processing system as compared with a clinician using a stethoscope. The stethoscope is dominated by the high-level valve closure snap and flow energy, e.g., S1 at 806. Therefore, a stethoscope auscultation cannot detect the low level, frequency band limited vibrational energy emitted from sources of blood flow turbulence within the subject's chest. The stethoscope being a single channel device does not provide any way to localize a source of vibrational cardiac energy beyond simple proximity of location to the chest surface auscultation point. Thus, the stethoscope is limited on two points: first, it does not allow the clinician to discriminate unwanted cardiac events either temporally or spectrally and, second, it does not provide simple and accurate localization of a source of energy. Note that, according to embodiments of the invention described herein, multiple features can be identified in a single slot. Any example presented herein with one feature per slot is provided merely for illustration and does not limit embodiments of the invention.

The peak locations in the Volumetric Vibration Intensity (VVI) image that correspond to VB feature F1 in FIG. 12A are presented in FIG. 12B. The peak picking technique and orthogonal x-z and y-z view fish tank display have been previously described. In FIG. 12B, VVI PAL locations of peaks from CBF (upper at 1260) and ABF (lower at 1262) focused scanning are shown. Application of the peak-picking algorithm described above, results in x-z and y-z viewing planes into the virtual transparent glass "fish tank" volume containing the peak locations. Within FIG. 12B and in each of the x-z and y-z viewing planes, the minimum intensity local peak value is indicated at 1252 with a circle symbol, "o." It is recalled that the highest intensity local peak is indicated by the encircled square "J" at 1254. The depth (cm) into the thorax is given by the z-axis at 12.30 and is partitioned into three regions corresponding to increasing depth. The first region, the anterior (front) epicardium coronary "artery region," beginning at 1253 has a depth z into the chest and ranges from z=2 to 4 centimeters. An intermediate "overlap region" beginning at 4 cm at 1255 is indicated by the "?" symbol and ranges from approximately 4 to 5 centimeters in depth. The deep thorax region beginning at 5 cm at 1257 is referred to as the valve region. As seen in FIG. 4, this "overlap region" depth range is where the pulmonic (P) valve, the mitral (M) valve and the Left Main Artery (LMA) could be contained. However, a normal P valve would not contain flow during the diastolic interval, DI, and the M valve surface curvatures are substantially smaller than those for a coronary artery. A third and deepest region is the nominal heart valve region titled "valve region" beginning at 1257. The valve region has a depth z into the chest and ranges from 5 to 11 centimeters in this example. It should be noted that the average depth from the chest surface to the mid-anterior surface of a male adult heart is 3.5 cm. Consequently, a peak depth less than 2.0 cm are considered physiologically unlikely and are likely a result of either a refractive or reflective shear wave convergence phenomenon. The VVI images of FIG. 12B present all of the local peaks detected inside of the imaging volume for Feature F1 Case 021813 normal baseline. As previously explained, to display these peak localizations, the numerical intensity values are first rank ordered and the median of this ordered list is obtained. If there are more than two (2) or more local VVI peaks, the location of the maximum value in the list is plotted with a square, "D," and those intensity values greater than the median but less than the maximum the locations are plotted with a ">." The location of the minimum intensity value in the rank ordered list is plotted with a circle, "o," and the locations of the intensity values greater than the minimum but less than the median are plotted with a "<." If only a single peak is obtained, then a relative decibel level is unobtainable and the "singular" case indicator (mx, mn)=(-inf, −60) for the peak value minimum to maximum range results. The signal-to-noise ratio (SNR) is given by the difference in dB between the maximum peak value intensity given at 1246 and the median value of the average intensity in the VVI image given at 1240. For the ABF localization process SNR=15.9939-9.9904=16,0-10.0=6 dB at 1270.

Feature 1 (Case 021813) Artery Region Below Detection Threshold FIG. 12B presents at 1272 the PAL localization estimate corresponding to the F1 feature from FIG. 11 at 1110 and FIG. 12A at 1210. This estimate from the ABF scan process at 1272 is given as (x, y, z)=(2.25, −3.75, 10.75) cm and corresponds to an SNR=6.0 dB. Note that as described above, this strength of the vibrational energy estimate, expressed as a SNR, is equivalent to the aforementioned metric of clinical significance (MCS). Thus, SNR of the vibrational energy estimate and MCS are used synonymously in this description of embodiments. The results of PAL processing for all four features in Case 021813 are summarized generally at 1300 in Table I and, in particular, the F1 PAL results are given at 1302. To summarize the PAL methodology, the vibrational cardiac data corresponding to FIG. 8 are processed as described above, i.e., first processing each channel average to obtain channel averaged PSD. This PSD can be obtained from either standard Fourier analysis methods or from the cross-spectral density matrix (CSDM) eigenvalue spectra as presented in U.S. Pat. No. 9,591,972, by Owsley et al. The channel Fourier transforms are processed further to obtain the CSDM for the array and then the CSDM is spatially scanned, i.e. processed across the vernier band (VB) of frequency that corresponds to the band of frequencies defined by the F1 feature to obtain the VVI image volume for the selected VB. The VVI image volume is processed with the peak-picking algorithm described above to present a tractable amount of data for presentation within this description of embodiments. With reference to FIG. 12B generally at 1250, a transparent x-z plane view into the CBF VVI image of energy local peaks is at 1260 (left). The x-z viewing plane presents a view into a "fish tank" transparent volume of peaks. This peak data presentation format shows the locations of the local intensity peaks obtained by beamforming the volume using the CBF algorithm from a view perpendicular to the x-z plane. The fish-tank format also shows a view from perpendicular to the y-z plane at 1261 that is orthogonal to the x-z viewing plane shown at 1260. The same VVI image of CBF beamformer output intensity peak locations is presented at 1260 with the same maximum intensity peak at 1254 at a depth z=5.25 cm. Together, these perpendicular viewing planes illustrate the distribution of intensity local maxima/peaks within the VVI image of the human subject.

The two lower FIGS. 1262 and 1263 in FIG. 12B are the perpendicular directional views of the ABF processed intensity peak locations. At the top of the ABF x-z and y-z viewing planes are the Feature F1 Vernier Band (VB) at 703-800 Hz, the run identifier (slot-1-021813-h-4-p-05), the maximum-minimum peak levels (mx, min) at (1246, 1247) and the median level VVI at 1240 (ABF VVI med level) parameters. Indicated at the top of the CBF y-z viewing plane at 1217 is the median VVI level decibel value of 11.9882=12.0 dB at 1217. This decibel value is the median (med) value for the vibration intensity levels in the CBF VVI image pixel cube. At 1262, in the same location in the lower ABF VVI peak value images, the median pixel value 9.9904=10.0 dB at 1240 is given for ABF focused beamforming processing. The maximum intensity pixel value location at 1256. (square symbol at 1256 of 16.0 dB) that is encircled and the minimum at 1258 (circle symbol at 1258 is 9.8202=9.8 dB) are identified. Clustered energy peak values indicated as o, < and > at 1224 through the artery depth and valve regions between the depths of 3 to 6 centimeters are detected. The F1 feature appears in the valve region at z=5.25 cm (CBF) and 10.75 cm (ABF). Because of a higher positional resolution the ABF process was able to locate the peak at z=10.75 cm whereas the CBF was not. Both CBF and ABF localized peak clusters at 1224 and 1234. The maximum peak spectrum levels are either below or at a 6 dB SNR threshold for clinical significance. The SNR for the maximum peak is calculated by subtracting the median VVI pixel intensity (med) in dB at 1217 and 1240 from the peak intensity in dB denoted by the peak value (maximum, minimum) dB=(mx, min) values at 1261 and 1263 for CBF and ABF respectively. Specifically, the ABF maximum Signal-to-Noise Ratio (mx-med)=(16.0-10.0)=6 dB. Table I in FIG. 13 at 1300 summarizes the PAL CBF and ABF analysis results for all four features identified in Case 021813 using the methods described above.

In FIG. 12B, the maximum ABF peak intensity shown at 1256 is at a depth of 10.75 cm and has an SNR of 6 dB. A clinical significance threshold of 6 dB for a coronary artery occlusion is met in this case but the localization at z=10.75 cm would indicate either a mitral (M) or a pulmonic (P) valve source. From Table I, it is observed that Feature F4 presents the next highest SNR is 2.3 dB at 1304 and this is below a 6 dB clinical significance threshold. These factors combine to indicate that there is a low probability that these peaks obtained from either the F1 feature or any of the other Case 021813 features are n indication of cardiovascular disease. However, it is also observed at 1224 and 1234 there is a cluster of intensity peaks consistent with coronary artery localization albeit with sub-threshold intensity levels. Such localizations could justifiably be qualified for a follow-up watch list for this individual.

A vibration sensing array that is conformal to the chest over an intercostal space has its largest aperture extent in the x-axis dimension as shown in FIG. 5 at 500. This orientation results in a maximum spatial resolution along the x-axis. In addition, this orientation has restricted aperture in the z and y directions, which corresponds to much less spatial resolving power in the z and y dimensions. This is why the peaks tend to be most clustered in a narrower range of distribution in x (see 1224 versus 1234) than in y.

With respect to FIG. 10 through FIG. 13, that pertain to a presumed healthy, fifty-two year-old male Case 021813, the analyses of features F1, F2, F3 and F4 for both CBF and ABF processing, yield PAL peak detection metrics that are either at or below the median-plus-6 dB detection threshold for clinical significance. However, these low-level detection results for coronary artery disease may indicate non-pathological turbulence sources such as arterial flow boundary layer, bifurcation, tortuosity and early stage coronary artery disease (CAD). For a 6 dB clinical significance threshold, none of the VB features for Case 021813 exhibit significant Spectrum Level (SL) in an artery depth region and, therefore, would not likely be of clinical importance for this CAD asymptomatic subject at the time of data acquisition.

Going forward in the clinical development of PAL it will be important to establish an optimal value for the clinical significance SNR threshold that is based on correlative experience with best practice diagnosis. Threshold optimization entails a process of conducting a large, statistically significant trial for which best practice provides independent "true" diagnoses that are compared to the outputs of the PAL processing described herein. With the truth, provided by independent diagnosis, the receiver-operating curve (ROC) consisting of sensitivity (correct detection probability) versus specificity (false détection probability) as a function of the threshold can be formulated and an optimal threshold operating point selected. Feature F1 presents with ABF SNR=6.0 dB at a depth of 10.75 cm which places the vibration source in the valve region. This is the so-called "strongest" result because other ABF response peaks occur that are consistent with the CBF lower maximum SNR detection at z=5.25 cm. The foregoing discussion of FIG. 8 and FIGS. 10 through FIG. 13 provides an analysis of vibrational cardiac data from which a state of health is assessed for the subject. The absence of a significant indication of arterial blood flow turbulence supports the fact that the Case 021813 subject is asymptomatic for coronary cardiovascular disease based on the PAL VVI image analyzed. In fact, with respect to all known medical history as of the acquisition date for Case 021813, there are no indicators of pathology and it is on this basis that Case 021813 has been selected going forward as a normal baseline for use as a standard noise floor (SNF) reference.

Producing an assessment of the state of health of a human subject includes the analysis of the human's vibrational cardiac data as described herein. To this end, it can also be helpful to compare a different subject's data or multiple data sets from the same subject where each data set is collected at a different time having allowed for possible disease progression. In such comparisons, the term standard noise floor (SNF) can be used to compare a test result from another human test wherein the analyst compares the present test results to a previous PSD and PAL analysis result, such as in, for example, either a follow-up examination or a test for "normality" relative to a known healthy individual from a similar cohort.

Case 112115: diagnosed M-valve calcification

FIG. 14 generally at 1400 presents the ensemble amplitude data acquired for Case 112115, which is the same format as for Case 021813 in FIG. 8. It is noted that systolic interval (S1) for Case 021813 (0.5 sec) is nominally the same as Case 112115 with nominally the same heart cycle length (0.9 sec).

FIG. 14 through FIG. 17 present a post-spectrum analysis localization (PAL) analysis for Case 112115 that involves the same human subject as the SNF Case 021813. The data for Case 112115 was acquired thirty-three months after the data for Case 021813 discussed in conjunction with FIG. 8 through FIG. 13. During this thirty-three month period, the subject became symptomatic of cardiac function difficulties and underwent echocardiographic analysis. Echocardiography established that moderate mitral (M) valve calcification had progressed during the intervening thirty-three months. With reference to FIG. 14, an ensemble of one-hundred and ten (110) heart cycles is illustrated with time represented on the horizontal axis at 1416 and amplitude represented on the vertical axis at 1402. The ensemble of heart cycles plotted in FIG. 14 is subjected to the identical VB CBF and ABF PAL processing as the ensemble from FIG. 8 described above. Namely, the ensemble of heart cycles was collected as described in conjunction with the figures above during periods of breath-hold by the subject. The vibrational cardiac data processing system cross-correlates the heart cycles with a master replica (selected from the ensemble) in order to time align the ensemble of heart cycles as described above. In the case of FIG. 14, the ensemble was time aligned to the time point corresponding to the peak of the S1 interval. The S1 interval is indicated at 1403. Other points in the ensemble of FIG. 14 can be used as the point for time alignment such as for example either the peak of the S2 interval 1407 or a combination of S1 and S2. However, to be consistent with the processing applied to the data collected earlier (021813) an S1-S2 master replica complex peak was used for time alignment.

As with the Case 021813 analysis above, Case 112115 heart cycle waveforms are pruned as desired to eliminate unwanted sources of noise arising from various sources such as digestive system noise and breathing noise. Two diastolic intervals are identified in FIG. 14 at 1410*a* and 1410*b*. The segment of the first diastolic interval (DI) is selected as indicated at 1408 as the start of the overlapping PAL analysis time intervals: Slot 1, 2, 3, and 4. For the comparison presented herein with a thirty-three month period separating the two measurements, the data sets (Case 021813) and (Case 112115) were processed the with the same methodology with respect to time alignment of the ensemble and slot designation. The features identified between the two data sets are different as discussed below.

With reference to FIG. 15A, generally at 1500, the power spectrum density estimates (PSDs) for the four time slots are defined with respect to time slot at 1506. The absolute spectrum level (dB) is given at 1504. The slot 1, 2, 3 and 4 PSD estimates are presented at 1501, 1502, 1503 and 1515 respectively. The Case 021813 SNF normal baseline PSD of FIG. 10 is compared at 1507/1508 to the follow-up Case 112115 PSD from the same individual in FIG. 15A after a diagnosis of M valve calcification. Most notable is the Case 021813 smooth and nearly monotonic decrease in PSD spectrum level in FIG. 10 relative to the decreasing but more featured character of Case 112115 PSD in FIG. 15A. The variability of the FIG. 15A PSD is indicative of the presence of low-level, resonant-like vibration induced by blood flow turbulence. The frequency band limited features below, referred to as "whistles," such as Feature F1 at 1513 and F10 at 1510, result from valve flow and artery flow vibration respectively. In the following, discussions that describe the different mechanisms for induced valve and artery vibration source localization and classification are presented. In FIG. 15B, the same four slot PSDs as FIG. 15A are presented but with normalization by the Case 021813 slot 2 baseline "normal" PSD. Features F1 and F10 are repeated but features F2 and F11 are defined following the normalizations performed in FIG. 15B. The normalized PSD of FIG. 15B is rich in features that are important to classify. To avoid the confusion that results from the graphical presentation of ten or more features on multiple over-plotted PSDs, FIG. 16 presents the four-slot PSD in FIG. 15B with a slot-by-slot breakout into subplots. In the following, with slot PSD breakout a total of thirteen (13) features are identified in FIG. 16 and processed with the PAL methodology.

As stated above, the PSD corresponding to the four DI time slots at 1414 are normalized by the Case 021813 slot 2 baseline "normal" SNF PSD. The four slot PSDs are superimposed and are identified by the legend at 1506. In FIG. 15A, frequency is indicated along the horizontal axis at 1512 and absolute spectrum level of the vibrational cardiac data signal along a vertical axis at 1504. In FIG. 15B, the spectrum level relative to the normal baseline is plotted in dB at 1522. The plotting legend 1506 indicates the line type used for slot 1, slot 2, slot 3, slot 4 and the baseline normal SNF case PSD at the 0 dB level at 1507.

Normalization of the estimated PSD can be used as follows: (a) to compare an ambient noise-free PSD spectrum level measurement of the system noise floor (SNF [1]) for sensor calibration and (b) to compare a specific human PSD measurement to an archival reference human baseline as a standard noise floor (SNF [2]). Note that the distinction in the use of the acronym SNF is by context, however, the use for calibration is secondary to the primary diagnostic use of normalization for comparison to a standard human reference. In this embodiment, Case 112115 in FIGS. 15A and 15B, which is a thirty-three month follow-up, is referenced to the earlier Case 021813 at the 0 dB level for the same human subject at a time when the human subject was considered to be clinically free of any known cardiovascular condition.

In FIG. 16 generally at 1600, the four slot Case 112115 PSD results presented in FIG. 15B are shown in breakout form in separate subplots at 1601 for slot 1, 1602 for slot 2, at 1603 for slot 3 and at 1604 for slot 4. In Case 112115, thirteen (13) features have been identified for PAL processing. However, in FIG. 15B, only four features could be easily identified within the over-plotted PSDs of the four diastolic time slots denoted, namely F1 at 1513, F2 at 1514, F10 at 1510 and F11 at 1511. Over-plotting of the slot PSDs facilitates a visual comparison of spectrum level and spectrum feature character by the analyst. The visual comparison is helpful to conceptualize a "feature" in the spectrum and the feature's "parameters." To avoid over complication, only four of the eleven features in the diastolic case 112115 are indicated in the overlapping PSD format of FIG. 15B: F1, F2, F10 and F11. Alternatively, as noted above, in FIG. 16, the four individual slot PSDs are presented in separate breakout subplots at 1601 (slot 1), 1602 (slot 2), 1603 (slot 3) and 1604 (slot 4). In FIG. 16, an example of the PAL analysis, the feature F8 from slot 3 at 1608 and feature F10 from slot 4 at 1610 are selected. The transparent fish tank localization display resulting from a PAL analysis for F8 is given in FIG. 17 and for F10 is given in FIG. 18. The PAL analyses for all thirteen (13) features in FIG. 16 have been performed and the parameters for all features are summarized in Table II in FIGS. 19A-B generally at 1900. The PAL summaries for F8 and F10 are at 1911 and 1913 respectively.

FIG. 17 at 1700 shows the perpendicular (orthogonal) views, x-z and y-z, of the peak volumetric vibration intensity (VVI) scan for both CBF, at 1702 and 1710, and ABF, at 1730 and 1740. The maximum intensity point for CBF is identified at 1704 with localization coordinates at 1734 and for ABF at 1714 with localization coordinates at 1744. The maximum and minimum VVI intensity levels for CBF are given at 1718 and 1708 respectively with the maximum value of 8.9812 dB=9.0 dB. Similarly, for ABF the maximum and minimum intensity levels are given at 1706 and 1716 respectively with the maximum intensity given by 4.7044 dB=4.7 dB and the minimum of −2.6 dB. The CBF median VVI level is given by 7.1512 dB=7.2 dB at 1717 and for ABF the median level is −0.94693=−0.9 dB at 1707. Accordingly, the Signal-to-Noise-Ratio for the CBF VVI maximum is obtained as SNR=9.0-7.2=1.8 dB at 1722 and for ABF as SNR=4.7−(−0.9)=5.6 dB at 1724. The ABF SNR=5.6 is slightly below a 6 dB clinical significance threshold but is none-the-less meaningful in the absence of a large trial-based clinical experience with the critical threshold parameter derived from an empirical ROC.

The nominal artery (2 to 4 cm), overlap region (?, 4 to 5 cm), and valve regions (5 to 11 cm) for the depth parameter z for ABF are defined at 1750, 1752 and 1754 respectively. The source ABF localization for F8 is most consistent with an artery at (x, y, z)=(4.75, −3.25, 3.25) cm indicated at 1714. This location is on the right side of the heart and 3.25 cm below the fourth intercostal space. It should be reemphasized that the accuracy and stability of the y-axis location is limited by the lack of vertical (y dimension) aperture for an array placed along a single intercostal space. For example, if the dominant propagation path from the source were to reflect off a rib surface the algebraic sign of the y location would change.

FIG. 18 presents the fish-tank peak location graphic for the second clinically significant feature F10 that is in the frequency band above 561 to 596 Hz in slot 4. The identical calculation procedure for specific parameters will not be repeated with respect to FIG. 17 and feature F8 above because all PAL analysis parameters are included in the tables presented in FIGS. 19A-B. Worthy of note is that, between slot 3 and 4, the CBF and ABF VVI peak maxima migrate in position from 1704 and 1714 respectively to 1804 and 1814. The VB frequency bands are different but overlapping and the heart shape would have changed between slot 3 and 4.

As an example of a Case 021813 follow-up by Case 112115, consider feature F1 in case 021813 in frequency band (703-800) Hz (FIG. 12B) with a follow-up in F9 in frequency band (770-795) Hz. Using ABF scan results, F1 was ABF localized at (x, y, z)=(2.25, −3.75, 10.75) cm (FIG. 12B at 1272) and F9 at (x, y, z)=(2.0, −2.5, 10.75) cm (FIG. 19B). For F1 SNR=6 dB and for F9 SNR=4.5 dB. Allowing for some instability in the y position estimate, −3.75 cm versus-2.5 cm (feature F1 from 021813 versus feature F9 from 112115), would strongly indicate repeatability and the potential for valve turbulence detection at least thirty months before a clinical diagnosis.

With respect to the PAL analysis summary in FIGS. 19A-B, there are five features, F5, F6, F10, F12 and F13 that exceed a 6 dB ABF SNR for clinical significance. A lower significance threshold at 3 dB would admit eight of thirteen features. Three of the eight localizations are in the artery zone (2 to 4 cm) and five of the eight localizations are in the valve zone (5 to 11 cm). As stated above, correlative clinical diagnosis experience with comparison to the angiographic "gold standard" as truth is required to establish optimum diagnostic predictive accuracy for a given clinical significance threshold. Features F5 and F6 in Table II at 1900 are worthy of note. In FIG. 16, Features F5 and F6 are selected to provide a further demonstration of PAL processing of vibration sensor array data. Feature F5 is located in slot 1 at 1605. Feature F6 is located in slot 2 at 1606. The width of a VB box indicates a bandwidth in frequency for PAL Vernier Band (VB) localization processing. Referring to the PAL processing Feature Summary in FIG. 19A Table HI, at 1901 it is noted that F5 has an ABF SNR=15.5 dB and at 1903 F6 has an ABF SNR=10.6 dB. Therefore, both F5 and F6 would exceed an SNR threshold for clinical significance at 6 dB. F5 is localized by ABF PAL at F5: (x, y, z)=(4.25, −1.75, 4) em and F6: (x, y, z)=(2.25, 0.75, 5.25) cm. In FIG. 16, at 1605 F5 is located in slot 1 and at 1606 F6 is in slot 2. Slot 2 is delayed by 0.085 sec (85 msec) relative to slot 1. The F5 ABF localization depth at z=4.0 cm places the vibration source at the artery-"overlap region" border and the F6 localization at z=5.25 cm. which places the source estimate in the valve region. Referring to FIG. 4, both of these depth locations are consistent with either a right coronary artery (RCA) or a mitral valve location. The VB center frequency for F5 is CF=380 Hz and for F6 CF=594 Hz. A lower CF=380 Hz would be more indicative of a normal valve vibration than an artery vibration. In contrast, a CF=594 Hz at a higher frequency would be more compatible with the smaller dimensions of an occluded artery vibration source but could also originate at a stiffened valve leaflet as a result of stenosis. The location corresponding to F5, (x=4.25 cm and y=−1.75 cm), is a location near the sternum below the location of the vibration sensing array placed over intercostal space four. A cluster of vibration energy peaks in slot 1 at 1607 is observed between 200 and 400 Hz. These peaks are likely valve vibration modes that are excited by the transient blood flow through a calcified M valve in the early DI rapid refilling phase. The variable valve blood flow velocity and changing shape of the valve in the early DI would cause the effect of a transient instantaneous discrete frequency.

FIG. 17 generally at 1700 gives the PAL fish tank display for local peak intensities (Case 112115 diastole) for the threshold clinically significant feature F8 in slot 3. The maximum intensity peak for CBF scanning is at 1704 and for ABF scanning at 1714. The CBF SNR is 1.8 dB at 1722 and the ABF SNR is 5.6 dB at 1724. The ABF localization is in the artery zone and the frequency CF=585 Hz is an indicator of artery turbulence.

In FIG. 19B, four diastolic features for Case 112115 either approach or exceed a 6 dB ABF SNR threshold: F8 at 5.7 dB (x=4.25, z=3.25 cm), F10 at 9.7 dB (x=2.25, z=5.25 cm), F12 at 16.5 dB (x=2.5, z=7.75 cm) and F13 at 16.2 dB (x=2, z=4 cm). Based on SNR, all six of the diastolic PAL localizations are clinically significant. Based on depth, F10 and perhaps F12 could be attributable to either a mitral (M) or tricuspid valve vibration source. Because the CF exceeds 400 Hz, F8 is most likely an artery source and F13, which is below 400 Hz, is uncertain. The potential importance of fusing echocardiographic anterior images and patient prior history with PAL results should not be underemphasized in the interpretation of a PAL localization. Ultrasonic imaging of the chest at the same intercostal space as the passive vibration imaging could provide a critical fusion of complementary position estimates and valve competency that would reduce spatial uncertainty. As used in this description of embodiments, the term "fusion" implies using one or more prior measurements that produce location information, such as, but not limited to, an ultrasound echo location measurement data (echocardiogram) during the interpretation of a PAL result or results. Other semi-noninvasive imaging measurements such as either a calcium scan or perfusion test can be fused with the PAL localization to increase diagnostic accuracy.

Systolic Interval PAL (Case 112115): Valve Flow Noise

The spectral signature of vibrations induced in a heart valve as a result of blood flow through the valve is further examined by considering the systolic interval (S1) of Case 112115_05S as identified in the ensemble amplitude plot of FIG. 20 of 2012 and generally shown at 2000. In a healthy heart, the dominant blood flow in systole is through the aortic (A) and pulmonic (P) valves as shown in FIG. 4 at 402 and 404. The P valve is nominally in the same depth range as the left coronary artery (LCA) at 420. However, the P valve should have an x-coordinate in the range 2<x<5 cm.

Spatially calibrated echocardiography can be used to non-invasively define this morphology at low cost. The power spectral density (PSD) estimates for the four time slots specified in FIG. 20 and normalized by the Case 021813 normal baseline are presented in FIG. 21 shown generally at 2100. The four normalized PSD plots in FIG. 21 are over-plotted with the plotting line type defined at 2106. Eight features are identified for this case, however, only four features (F1 at 2101, F2 at 2102, F5 at 2105 and F8 at 2108) are presented in FIG. 21. Instead, the PSD breakouts for each individual time slot are shown in the corresponding subplots in FIG. 22 and all eight features are identified. In FIG. 21 at 2110 and the corresponding FIG. 22 at 2210, a low-frequency swath in slot 4 is identified and a time variable frequency event is identified at 2112 in FIGS. 21 and 2212 in FIG. 22. The swath at 2110 and 2210 is limited to slot 4 but the transient frequency modulation event at 2112 and 2212 can be seen clearly in FIG. 22 to continue across slots 2, 3 and 4 with energy remaining below 400 Hz. Because A and P valve flow is dominant in the S1, this further supports the contention that the region of the PSD signature at 2116 is a result of induced valve vibration and not coronary artery vibration. The PAL parameter estimation summary for Case 112115_05S systolic analysis is given in Table III in FIG. 2300A and continued in FIG. 2300B.

Comparing the four slot PSDs in FIGS. 21 and 22 it is seen that, as time progresses from slot 1 to 4, the broad background level of the spectrum increases nearly 15 dB as a function of flow velocity and valve action. Also significant is the complete absence of frequency band-limited, whistle-like features above 400 Hz. Such features are indicative of higher frequency resonance that would originate in an artery with a much smaller flow cross-section than a valve. The range of depths for all ABF feature localizations is 3≤z≤5.25 cm (FIGS. 23A-23B). With the coordinate system origin (x=0) located approximately 4 cm to the left of the left edge of the sternum, the horizontal localizations occur in the aperture 1.75<x<4.25 cm. The vibration source is most likely to be the pulmonic valve that is in vibration during systole with the trajectory x: 2.25 cm (slot 2)=>>4.25 cm (slot 3)=>1.75 cm (slot 4). Most important from this direct PAL analysis of systolic pulmonic flow induced vibration is that the spectrum shape above 380 Hz is smooth but elevated in level. These observations are consistent with the following statements: (a) there is no detectable coronary artery blood flow during the S1, (b) the P and A valves produce band limited PSD features below 400 Hz and (c) there is evidence of increasing broad frequency band energy during the S1 that is boundary layer flow velocity dependent. An observation based on the phonetic spectrum of the sounds "LUB" and "DUB" is that the slot 1 "LUB" sound in 2201 at 2240 does not coincide with the increase in broadband spectrum level in slot 4 with the "DUB" sound in 2204 at 2260.

By extension from the P valve during systole to the M valve during diastole from FIG. 15B at 1516, in diastole, the whistle-like features F10 and F11 of limited bandwidth above 350-400 Hz derive from either a calcified mitral valve or a coronary occlusion. A valve echocardiograph can and should provide confirmation of calcification. This extension is justified because the pulmonic valve annulus size is smaller (1.8 to 2.3) cm than the mitral valve annulus size (3.0 to 3.5) cm, therefore the flow velocity through the mitral valve must be less than the pulmonic flow velocity because system flow volume is constant. The Strouhal number(S) relationship between flow velocity (U), annulus hydraulic diameter (D) and shedding vortex frequency (f) given by:

$$f = SU/D$$

would suggest that the upper frequency of M valve flow induced vibrations should have an upper bound at or below the frequency characteristic of flow induced P valve vibration with all conditions considered normal. With this perspective on the frequency signature for valve flow induced vibration, an examination of Table II at FIGS. 19A-B (diastolic interval PAL results) implies that the features F3, F4, F6 (ABF SNR=10.6 dB at 1903), F7, F8 (ABF SNR=5.6 dB), F9, F10 (ABF SNR=9.7 dB at 1913) and F11 are indicators of either coronary occlusion or a calcified mitral valve. The observation in FIG. 16 that the possible calcified M valve indicators in the slot 1 features F1, F2 and F5 diminish and disappear in the progression to slot 4 would indicate that the related valve vibration is an early diastole phenomenon. Fusing these indicators from a PAL analysis with valve echocardiography further defines the diagnostic methodology with respect to either valve stenosis or coronary artery vibration.

Diastolic PAL: Stent in the Upper Left Anterior Descending (LAD)

Generally, at 2400 FIG. 24 presents the synchronized ensemble amplitude time waveforms for Case 062012 acquired from a sixty-eight year old male previously diagnosed and treated for a nearly total occlusion of the LAD. The blockage was immediately downstream from the LMA-LCX branch point and intervention consisted of the placement of a stent. The percutaneous coronary intervention (PCI) stent procedure had been performed six (6) months prior to the acquisition of the data presented in FIG. 24. The interval selected for processing at 2402 is a hybrid interval that includes a general portion of the diastolic interval (DI) and the systolic interval (S1), wherein it is noted that slot 4 is centered on the S1 heart sound at 2404. This data set is focused on turbulent flow induced vibration PAL in the LMA, the LAD and the possibility of vibration from all four valves. Slots 1-3 acquire M and T valve vibration and slot 4 acquires A and P valve vibration.

The PSDs for the four slots defined in FIG. 24 for Case 062012 are presented in separate breakout subplots in FIG. 25 generally at 2500. The band-limited features F1 to F12, corresponding respectively to 2501 to 2512, are defined with three features identified in each slot interval. A swept frequency feature in the band 640 to 760 Hz is noted in slot 4 at 2520, Also, a 60 Hz harmonic "comb" is inserted with a 180 Hz (3-rd harmonic) and 300 Hz (5-th harmonic) identifiers at 2530. The swept frequency feature occurs in slot 4 and is coincident with high velocity, early systolic blood flow and the S1 heart sound. In FIG. 25 at 2532, the S1 "LUB" heart sound is coincident with a 10 to 12 dB increase in spectrum level below 180 Hz.

FIG. 26 generally at 2600 presents the transparent fish-tank view of the peaks in the CBF (top) and ABF (bottom) volumetric vibration intensity (VVI) scan. The CBF and ABF are in agreement with the maximum peak value location at (x, y, z)=(2.0, 1.75, 3.0) cm indicated at 2604 and 2606 for both the maximum peak value at 2607 and the maximum peak value at 2608. The maximum peak SNR for CBF is 4.6 dB at 2603 and for ABF is 15.5 dB at 2605. This is in accordance with the ABF design criterion, which is the maximization of signal-to-background noise ratio. The localization at 2604 and 2606 places the vibration source at the midpoint of the artery region at z=3.0 cm. Moreover, the x=2.0 cm coordinate is more suggestive of vibration localized in the left coronary artery than in the mitral valve.

FIGS. 27A-27B present a summary of the PAL analysis of the twelve (12) VB features identified in FIG. 25. Feature F1 with an ABF SNR=3.7 dB is below a 6 dB clinical significance threshold but could indicate mild LMA vibration. This result implies that a residual occlusive segment in a coronary artery remains six (6) months after a PCI involving a stent placement. Features F2 and F3 both have high SNR and depth z>5.5 cm that is consistent with mitral valve vibration. Features F4, F5 and F6 in slot 2 present an ABF SNR that exceeds the significance threshold and the (x, z) coordinates depth (2.5 cm<z<4 cm) are consistent with the generalized coronary artery and with the presumed location of the stent. Also, features F7, F8 and F9 in slot 3 all exceed the SNR significance threshold and are contained within the artery region. It is observed that F4 in slot 2 at 2504 (FIG. 25) could be linked to F7 in slot 3 in both frequency and localization proximity. While the structural mechanisms for transmission of vibration originating at the mitral valve propagating to the anterior surface of the heart are complex, the source location estimated by PAL processing of PCI Case 062012 is consistent with the expected depth of heart valves and the known location of the stenting device. The stenting device, while enabling increased blood flow, could represent a source of near laminar flow disruption and thereby produce an associated induced arterial vibration. Case 062012 uses Case 021813 slot 2 SNF for normalization FIG. 25. Relative to this SNF, Case 062012 in all slots presents a large spectrum level increase from 100 to 1000 Hz. This is not a frequency band limited effect and may indicate arterial occlusion that is spatially extended along the artery with a wide distribution of occlusion surface facet aspect angles and curvature.

Interpretation of Flow Induced Transient PSD Feature Characteristics

The transient nature of PSD features during a sequence of consecutive time slots is a result of the changing morphology of the heart during the heart cycle. The net effect of the muscular action of the heart is to control the blood flow velocity through a closed system containing occlusions to that flow in the form of arteries and valves that, in turn, can induce turbulence. As the heart muscle repeatedly contracts and relaxes, the effective hydraulic diameter of blood flow passages varies continuously with time. As a result of heart wall contraction and relaxation, arteries embedded in the heart wall are cyclically compressed in systole and opened in diastole. In addition, the blood flow velocity modulates with the operation of the valves and the pumping phase of the chambers. The nature of turbulence can be a tendency to induce temporally short, i.e. transient, intervals of nearly periodic pressure fluctuation on the tissue walls downstream from the locas of maximum flow restriction. Flow induced, near-periodicity can produce short intervals of very frequency band-limited vibrational energy. This intermittent quasi-periodic pressure fluctuation from turbulent flow through either arteries or valves as a source of contiguous transient tissue vibration is in contrast to a valve closure transient that within a single heart cycle is more impulsive from a single leaflet impact than periodic. The valve closure dynamics associated with leaflet and fluid mass impact results in a continuous swath of energy in frequency such as at 2210 in slot 4 presented in FIG. 22 at 2204. Referring back to FIG. 21, valve leaflet closure noise at 2110 and quasi-periodic valve turbulence noise at 2112 is observed below approximately 400 Hz. Artery and valve boundary layer turbulence induced noise is broad in spectrum as in F5 at 2105 and F8 at 2108. As an example of quasi-periodic transients, consider the four unnormalized slot PSDs in FIG. 28 generally at 2800. The Case 112115 shows features F6 and F7 at 2806 and 2807 respectively. FIG. 29 presents, generally at 2900, the same features F6 at 2906 and F7 at 2907 as FIG. 28 but the PSD for each of four sequential diastolic slots is normalized by the "normal" SNF baseline slot 2 PSD of Case 021813. In various embodiments, two aspects of transient features are described herein, In one aspect, a transient feature is an event that occurs only for a portion of an observation interval. For example, the transient feature can appear in one time slot but not in another time slot. Another aspect of a transient feature is that the instantaneous frequency of a feature changes continuously as a function of time as the morphology of an occluded artery or incompetent valve changes during a heart cycle. As observed in FIG. 29, this later aspect can be seen in features F7 in slot 2 and F6 in slot 4. Generally at 3000, this transient dynamic frequency behavior is emphasized in FIG. 30 that presents the same F6 and F7 features in an expanded PSD frequency band under the heading "Human Data" for Case 112115 at 3010. To the right of the human data figure is an expanded frequency PSD result from a numerically "Simulated Data" event at 3020. The frequencies of 555 Hz and 592 Hz are identified at 3050. Although the human and simulated PSD segments are not exactly the same, they are temporally similar enough to allow an analyst to interpret, in general terms, the behavior of an actual transient human PSD result as a time-variable, instantaneous frequency transient vibration produced by a rapid transition in flow vortex shedding frequency between 592 Hz and 555 Hz. The interpretive methodology for an understanding of the time slot PSD evolution is referred to as post (spectrum) analysis tracking (PAT).

The numerical PAT simulation was conducted for the simulation of F6 and F7 as in FIG. 30 according to the amplitude at 3152 and frequency 3154 verses time trajectories shown in FIG. 31 generally at 3100. The simulation demonstrates at slot time intervals 3161, 3162, 3163, and 3164, how the PAT slot-to-slot PSD analysis captures a mechanism wherein turbulent blood flow induces oscillatory vibration for which the frequency spectrum can be approximated by a discrete-frequency "hopping", time-varying instantaneous signal waveform. The instantaneous frequency modulates between 555 Hz at 3130 to 592 Hz at 3120. A necessary but not sufficient temporal representation of the instantaneous amplitude and frequency for the simulated vibration waveform is depicted in FIG. 31. Simulation can also illustrate that transient feature characteristics can occur both with blood flow turbulence originating at an artery source as well as at a heart valve source. The transient behavior is a result of the changing shape of the occlusion orifice during the observation intervals corresponding to the time slots. The characteristic turbulent flow shedding frequency varies instantaneously with the shape of the orifice and the velocity of blood flow through the orifice.

The effect of a frequency transition during a time slot corresponding to the Case 112115 human data features F6 and F7 from FIG. 30 is the distribution of energy across the Fourier analysis frequency band. With reference to FIG. 31, features F6 and F7 (artery location) are simulated numerically using a computer-generated waveform at a frequency hopping from 592 Hz and 555 Hz and then back to 592 Hz in conjunction with amplitude control. In FIG. 31, time is indicated on the horizontal axis at 3102. The amplitude-time schedule is given in the top subplot at 3110. In the bottom subplot the frequency-time schedule is presented. The overall amplitude schedule is signified in the top subplot at 3152 with 1 and 0 representing the full "on" at 3156 and "off" at 3158 respectively. A first frequency at 592 Hz is active at 3140 until the time of a linear frequency transition interval at 3160 to the frequency 555 Hz at 3150. At the end of the time interval 3156 the signal turns off as determined at 3158. If the instantaneous frequency of the simulated vibration waveform dwells at the two frequencies at different times during a slot, then the FFT PSD process will show a response at each frequency that is generally in proportion to the amount of time the frequency remained within each FFT frequency bin as discussed relative to FIG. 9.

Signals produced using the amplitude and frequency-timing diagrams of 3152 and 3154 plot time on a horizontal axis. For a time period indicated at 3156 the frequencies are "on" and change as indicated at 3160 at amplitude 1.0 a time period indicated at 3158 the frequencies are switched "off." The combined effect of 3110 and 3120 is a transient signal with PSDs as shown in FIG. 30 at 3020, Simulated Data, that approximate in 3020 F6 and F7 time slot PSDs shown in 3010, Human Data. The time line for the simulation of overlapping time slots is shown at 3161 through 3164 corresponding to the actual human data time slots. The simulation proceeds by transforming a time variable discrete frequency signal in each time slot as defined in FIG. 31 to the frequency domain. In one embodiment, this is done by simulating the method by which the vibrational cardiac data is processed in PAL using a Fast Fourier Transform (FFT) within a slot interval time series signal with frequency changes according to the variation prescribed in FIG. 31. The outcome of such a transformation on the frequency domain processing to obtain the PSD is illustrated in FIG. 30 below for both actual human data 3010 and the simulation data 3020. An observation of the PAT "footprint" for a transient signal with a time variable frequency in a PSD slot sequence allows a more complete understanding of the blood flow dynamics and, therefore, classification of the occlusion.

Valve Closure Transients

FIG. 11 at 1127, FIG. 15 at 1521, FIG. 16 at 1609 and FIG. 21/22 at 2210 all present PSD results for slot intervals that capture a valve closure snap event. The dominant feature produced by a valve snap exhibits a center frequency (CF) either in the region around 200 Hz or below and has a relatively smooth shape with a frequency extent, i.e. bandwidth (BW), up to 100 Hz. The feature shape has been referred to as a type of spectrum swath that presumably results from the physical contact of valve leaflets and fluid at the time of valve closure in a blood flow field. In addition to the swath, the overall broadband level of spectral energy resulting from boundary layer flow turbulence can be elevated coincidently as indicated in FIG. 11 by feature F4 at 1114. In FIGS. 21 and 22, feature F8 at 2108 exhibits a broadband level increase that is consistent with boundary layer turbulence in flow through the P and A valves and the S2 valve closure heart sound. The smooth swath shape would be the result of an impulse of vibrational energy occurring simultaneously at all frequencies in the swath band with intensities conforming to the PSD spectrum level in the frequency band of the swath. This is in contrast to the vibrational signal model suggested by oscillatory turbulent flow induced vibration, namely, a time-varying instantaneous discrete frequency waveform that may sweep through a spectral band and produce a "spikey" set of narrow frequency band features in the temporally averaged PSD estimate. An example of this turbulent flow induced spikey feature set is FIG. 22 at 2212/2220 in slots 2, 3 and 4. The impulse valve closure snap vibration waveform would not be as amenable to modeling by a linear predictive, all-pole system that is driven by broad frequency band independent noise. Instead, a linear system model containing zero locations is appropriate. Indeed, direct modeling of both discrete frequencies, time varying poles and shaped Butterworth-type, time varying zeros would seem to represent a powerful interpretive tool for a model-based understanding of vibrations emanating from valves and arteries. In the analysis presented herein, it is not necessary to presume a linear system model for the generation of vibrational signals. As such, the nonparametric approach herein is robust to any potential model mismatch and the associated spectral bias error that would result from this mismatch.

FIG. 32 illustrates, generally at 3200, a power spectral density (PSD) example that compares numerical simulations for a continuous spectrum, flat swath-type and spikey-type spectrum at 3210 and 3220 respectively. Amplitude level in dB is on the vertical axis at 3202 and frequency in Hz is on the horizontal axis at 3204. The simulated feature at 3210 results in a continuous, i.e. smooth, distribution of energy simultaneously at all frequencies over the frequency band 235-310 Hz at 3230. The spikey feature at 3220 is the result of a signal with a single discrete frequency that is swept through time slots in the frequency band 555-592 Hz at 3240 as described above in conjunction with FIG. 31. In summary, the difference in VB spectral signatures between valve snap and occlusion induced turbulence combined with a localization is critical for classification.

Input-Process-Output (IPO) Diagrams for PAL

The IPO flow chart in FIG. 33 illustrates, generally at 3300, the PAL method of localizing the source of the energy associated with a single feature in vibrational cardiac data, according to embodiments o the invention. With reference to FIG. 33, a process starts at a block 3302. At a block 3304, vibrational cardiac data from a selected time slot interval in the heart cycle is acquired from at least three transducers. The data ensemble acquired from a multiplicity of heart cycles is time synchronized between the transducers to preserve relative time delay information and insert a time marker in the heart cycle for an ensemble of heart cycles. This allows synchronized time and sensor averaging of heart cycle strobe time slot intervals over the temporal ensemble and increases the power spectral density (PSD) signal-to-noise ratio (SNR) as a result of reduced fluctuation in the estimated PSD. If vibration sources are to be localized in three dimensions, the data ensemble can be acquired from a small vibration transducer array with as few as three channels or an array with a large multiplicity of sensor channels. In some embodiments, the array will be a chest conformal line array having extent along three mutually orthogonal axes and placed over either one or more intercostal opening. In other embodiments, the array is made up of two or more linear conformal arrays over multiple intercostal spaces. In yet other embodiments, the array is a general conformal array of sensors placed over intercostal openings. Those of skill in the array design art will realize that an array can be constructed with the required extent along the orthogonal axes to provide various desired spatial resolutions for use when scanning the volume within the subject human's chest.

At a block 3306 an ensemble averaged power spectral density estimate (PSD) is created from the synchronized ensemble of data from the block 3304. A PSD is created for each channel that is used for processing the data from the heart cycles. The PSD estimation procedure can also include averaging the sensor channel PSD estimates over the channel number index. An identical procedure can be employed to analyze the vibrational field on the chest surface during both the diastolic (DI) and systolic (S1) intervals. Note that an interval of time employed to analyze the vibrational field can be flexibly selected to include the DI and the S1 or portions of the DI and the S1. Thus, the method described is robust and is not limited to the DI or S1 individually. In yet other embodiments, the entire heart waveform is processed which effectively means that an interval of time is equivalent to the entire duration of the heart waveform. PSD estimates can also be obtained from the spectra of the eigenvalues of the intersensor coherence-based gross-spectral density matrix (CSDM).

At a block 3308 a feature is identified in a PSD estimate, where the PSD is obtained from the block 3306. The feature can be identified either manually by a data analyst or by using an artificial intelligence (AI) logic block in cardiac data processing system. In various embodiments, features are analyzed using characteristics of features such as center frequency (CF), bandwidth (BW), Q-factor (Q=CF/BW), feature smoothness, PSD plateau spectrum level and signal-to-noise ratio (SNR) as described in conjunction with the figures above. CF modulation between slots can also be interpreted as discussed in FIGS. 28 through 32. One or more libraries of spectrum feature signature data can be used in method 3300 to identify a feature, for example in the block 3308. As used in this description of embodiments, a library of spectrum feature signature data is created from analysis results made on a plurality of features from either a single human or a plurality of humans.

At a block 3310, a vernier band (VB) of frequency is established for the feature identified in the block 3308. In some embodiments, a VB of frequency is established by filtering a signal in the time domain.

In the block 3312, the information in a VB is processed to obtain a location of a feature. This location information can be fused with ultrasonic imaging results for mutual validation. In some embodiments, a CSDM is created from the time ensemble averaging of the channel-by-channel, cross-channel products of the channel complex valued Fast Fourier Transform (FFT). In some embodiments, the CSDM is processed using a conventional beamformer (CBF) algorithm to obtain the localization of a feature. In some embodiments, the CSDM is processed using an adaptive beamformer (ABF) algorithm to obtain the localization of a feature. In some embodiments, time-delay beam forming is used to obtain a location of a feature. In yet other embodiments, triangulation is used to obtain a location for a feature.

At a block 3314 the location estimate obtained from the block 3312 is compared against a priori knowledge of the physiology, including in some embodiments ultrasonic images, for a human to determine if the location is consistent with either a coronary artery location or a heart valve source or has an unresolved location. At the block 3314 the location estimate obtained from the block 3312 is compared against any other archival physiological a priori data for a human to determine if the location is a location of an artery, a valve or both. In some cases, the location estimates from the block 3312 informs the potential utility of ancillary measurements from systems employing, for example, echocardiography, calcium scanning and perfusion imaging. As used in this description of embodiments, terms such as; "ancillary measurements," "ancillary imaging procedures," "ancillary spatially calibrated imaging procedure data" are used to refer to measurement techniques/data that do not use passive measurement of vibrational cardiac data acquired at a surface of a human. It is important to note that all of these "ancillary measurements," "ancillary imaging procedures," "ancillary spatially calibrated imaging procedure data," etc., collectively referred to herein as "ancillary measurements," do not produce a source location of the blood flow turbulence induced vibration. These ancillary measurements are merely used to assist in the analysis of the location data derived from turbulent blood flow by providing confirmation that there is in fact an artery or a heart valve in a location that is consistent with where the blood flow turbulence induced vibration analysis is locating a source. Such use of ancillary measurements provides at a minimum, a basic check, and at most, an independent topographical (spatial) calibration for the blood flow turbulence induced vibration analysis by other physical means that are provided by the ancillary measurements.

At a block 3318 a state of health of a subject is evaluated by incorporating a fusion of all a priori clinically relevant knowledge about the patient, the spectrum characteristics of all PSD features and the locations of all the identified features obtained from block 3314.

At a block 3320 the process stops.

FIG. 34 illustrates, generally at 3400, another perspective of the methodology for localizing a vibration source that produces a VB feature in the power spectral density (PSD) signature for cardiovascular vibrational sensor array data, according to embodiments of the invention. With reference to FIG. 34, a process begins at a block 3402.

At a block 3404 an unwanted event is separated from the vibrational cardiac data (VCD). In one or more embodiments, the unwanted event is general ambient noise, vibrational energy as a result of valve closure, respiratory system and digestive system noise. In other embodiments, the unwanted coronary event is vibrational motion from the environment. In other embodiments, the unwanted event is ambient electromagnetic noise from the environment. In some embodiments, the unwanted event is separated by breath-hold while the vibrational cardiac data is collected. In some embodiments, separating an unwanted event is performed by pruning a heart cycle from the group of heart cycles that comprise an ensemble of heart cycles. In some embodiments, the separation of an unwanted event is performed by the deselection of portions of the frequency spectrum for consideration with respect to either arterial or valve flow sources of vibration.

At a block 3406 the VCD is evaluated to identify a PSD VB feature and to select a vernier band (VB) of frequency associated with the feature over which the localization beamforming will be performed. In one or more embodiments, within the block 3406 a power spectral density (PSD) estimate process is performed on an ensemble of heart cycles for each channel of the three or more sensors used to collect the vibrational cardiac data. In some embodiments an analyst evaluates the PSD and selects one or more features based on characteristics of the feature as described in conjunction with the above discussion and figures. In other embodiments, a cardiac data processing system executes a logic routine that analyzes the vibrational cardiac data and extracts one or more features for localization. One or more libraries of spectrum feature signature data can be used in method 3400 to identify a feature, for example in the block 3406. As used in this description of embodiments, a library of spectrum feature signature data is created from analysis results made on a plurality of features from either a single human or a plurality of humans.

At a block 3408 the VCD is processed using the VB of frequency to establish a location for the feature source. In some embodiments, a cross (channel)-spectral density matrix (CSDM) is created in conjunction with the PSD estimation process for the multiplicity of vibration sensor array channels. In some embodiments, the CSDM is processed using a CBF algorithm to obtain a location of a feature. In some embodiments, the CSDM is processed using an ABF algorithm to obtain a location of a feature source. In yet other embodiments, the CSDM in a VB is processed in a VB using a CBF algorithm and an ABF algorithm to obtain locations of a feature source. In some embodiments, time-delay beam forming is used to obtain a location of a feature. In yet other embodiments, triangulation in a VB is used to obtain a location for a feature source.

At a block 3410 the location obtained from the block 3408 is compared against any other ancillary physiological a priori data for a human to determine if the location(s) is a location of an artery, a valve or both. In some cases, the location(s) estimates from the block 3312 informs the acquisition of new measurements from systems employing echocardiography, calcium imaging, perfusion imaging or the other measurement systems described above.

At a block 3410 the location obtained from the block 3408 is compared against archival patient data and assumed physiological data for a human to determine if the estimated location is consistent with the location of an artery.

At a block 3414 a state of health of a subject is evaluated by considering a fusion of the all a priori knowledge about the patient, the characteristics of the PSD signature identified features and the locations of the feature sources using either one or more locations estimated from blocks 3410.

At a block 3416 the process stops.

FIG. 35 illustrates, generally at 3500, different processes that can be used for localizing a feature source of vibrational cardiac data using the methods of FIG. 33 and FIG. 34, according to embodiments of the invention.

At a block 3502 vibrational cardiac data (VCD) is processed to obtain the location coordinates for a PSD feature source contained therein. The processes 3500 can be representative of the block 3312 from FIG. 33 or the block 3408 from FIG. 34. The location of the feature source is obtained, in various embodiments, by processing the VCD by one or more methods. In a block 3504 the vibrational cardiac data is processed in a VB using a CBF algorithm to obtain an estimate of the location of the source of the vibrational cardiac data for the feature. In a block 3506, the VCD in a VB is processed by an ABF algorithm to obtain an estimate of the location of a vibration source identified by a selected feature. In a block 3508 the VCD is processed in a VB using triangulation and cross fixing to obtain an estimate of the location of the source of the VCD for the feature. In a block 3510 the VCD is processed in a VB with a user-defined location estimation method to obtain an estimate of the location of the source of the vibrational cardiac data, i.e. localization, of the source of the vibration PSD feature. Such user-defined location estimation methods are not limited to a combination of triangulation and either ABF processing or CBF processing.

Localization of the Source of a Transient Feature

FIG. 36 illustrates, generally at 3600, the different processes that are linked sequentially for localizing a feature source of vibrational cardiac data using the methods of FIG. 33 and FIG. 34, according to embodiments of the invention. The sequence of processes begins at 3602 and, initially, acquires and synchronizes an ensemble of heart cycle recordings from a multiplicity of vibration sensors. At 3606 the ensemble is used to estimate an ensemble and sensor averaged Power Spectral Density (PSD) from which signature features are identified. These features are used to direct the analysis to frequency bands in the PSD for estimating the location of blood flow turbulence induced vibration sources using the PAL and PAT processing algorithms and blood flow dynamics principles in 3608 and 3610 respectively. In a process 3612, the PAL and PAT analyses results are fused with all relevant data, including ultrasound echo images, to classify the cardiovascular system under examination. At 3614 the sequence of processes is complete.

Occlusion Morphology Modulated Turbulence

The instantaneous frequency content and elastic vibration wave propagation mode of a turbulent blood flow induced tissue vibration are determined by a combination of the structural form (morphology) of the occluding aperture, the velocity of the blood through the occlusion orifice, the viscosity of the blood and the elasticity of the tissue contiguous to and surrounding the region of turbulence. In the case of either a coronary artery lesion or an incompetent heart valve both the morphology and the blood flow velocity radial profile and viscosity profile are functions of time. While an ensemble of acquired heart beat cycles can be parsed and time synchronized with some degree of accuracy, two heart cycles are never identical, however, the differences can be accommodated as random variations and treated statistically by averaging over the acquired ensemble of a multiplicity of parsed and synchronized heart cycles. As previously stated, the left side of FIG. 9 is a pictorial attempt to illustrate these random cycle-to-cycle differences by imparting slightly different frequency trajectories to each of the B heart cycles in the ensemble.

For purposes of discussing and understanding the embodiments of the invention, it is understood that various terms are used by those knowledgeable in the art to describe methodology, techniques and various alternative approaches. Furthermore, in the description, for purposes of explanation, numerous specific details are set forth in order to provide a thorough understanding of the present invention. It will be evident, however, to one of ordinary skill in the art that the present invention may be practiced without these specific details. In some instances, well-known structures and devices are shown in block diagram form, rather than in detail, in order to avoid obscuring the present invention. These embodiments are described in sufficient detail to enable those of ordinary skill in the art to practice the invention, and it is to be understood that other embodiments may be utilized and that logical, mechanical, electrical, computational and other changes may be made without departing from the scope of the present invention.

Some portions of the description may be presented in terms of algorithms and symbolic representations of operations on, for example, data bits within a computer memory. These algorithmic descriptions and representations are the means used by those of ordinary skill in the signal analysis and data processing arts to most effectively convey the substance of their work to others of ordinary skill in the art. An algorithm is herein, and generally, conceived to be a self-consistent sequence of acts leading to a desired result. The acts are those requiring physical manipulations of physical quantities. Usually, though not necessarily, these quantities take the form of mechanical, electrical or magnetic signals capable of being acquired, transformed, stored, transferred, combined, compared, and otherwise manipulated. It has proven convenient at times, principally for reasons of common usage, to refer to these signals represented as bits, values, elements, symbols, characters, terms, numbers, waveforms, data, sampled data, time series or the like.

It should be borne in mind, however, that all of these and similar terms are to be associated with the appropriate physical quantities and are merely convenient labels applied to these quantities. Unless specifically stated otherwise as apparent from the discussion, it is appreciated that throughout the description, discussions utilizing terms such as "analyzing" or "processing" or "computing" or "calculating" or "determining" or "displaying" or the like, can refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

An apparatus for performing the operations herein can implement the present invention. This apparatus may be specially constructed for the required purposes, or it may comprise a set of multiple transducers, general-purpose computer, selectively activated or reconfigured by a computer program stored in the computer. It may also consist of a combination of both a specially constructed device and a program-activated computer. Such a computer program may be stored in a computer readable storage medium, such as, but not limited to, any type of disk including floppy disks, hard disks, optical disks, compact disk read-only memories (CD-ROMs), and magnetic-optical disks, read-only memories (ROMs), random access memories (RAMs), electrically programmable read-only memories (EPROM) s, electrically erasable programmable read-only memories (EEPROMs), FLASH memories, magnetic or optical cards, etc., or any type of media suitable for storing electronic instructions either local to the computer or remote to the computer.

The algorithms and displays presented herein are not inherently related to any particular computer or other apparatus. Various general-purpose systems may be used with programs in accordance with the teachings herein, or it may prove convenient to construct a more specialized apparatus to perform the required method. For example, any of the methods according to the present invention can be implemented in hard-wired circuitry, by programming a general-purpose processor, or by any combination of hardware and software. One of ordinary skill in the art will immediately appreciate that the invention can be practiced with digital computing system configurations other than those described, including hand-held devices, multiprocessor systems, microprocessor-based or programmable consumer electronics, digital signal processing (DSP) devices, network PCs, cloud services, minicomputers, mainframe computers, parallel computing architectures and the like. The invention can also be practiced in distributed computing environments where tasks are performed by remote processing devices that are linked through a communications network.

The methods of the invention may be implemented using computer software. If written in a programming language conforming to a recognized standard, sequences of instructions designed to implement the methods can be either compiled and/or executed on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, application, driver, algorithm,), as taking an action or causing a result. Such expressions are merely a shorthand way of saying that execution of the software by a computer causes the processor of the computer to perform a desired action or produce a desired result.

It is to be understood that various terms and techniques are used by those knowledgeable in the art to describe communications, protocols, applications, implementations, mechanisms, etc. One such technique is the description of an implementation of a technique in terms of an algorithm or mathematical expression. That is, while the technique may be, for example, implemented as executing program algorithmic code on a computer, the expression of that technique may be more aptly and succinctly conveyed and communicated as a formula, algorithm, mathematical expression, flow diagram or flow chart. Thus, one of ordinary skill in the art would recognize a block denoting A+B=C as an additive function whose implementation in hardware and/or software would take two inputs (A and B) and produce a summation output (C). Thus, the use of formula, algorithm, or mathematical expression as descriptions is to be understood as having a physical embodiment in at least hardware and/or software (such as a computer system in which the techniques of the present invention may be practiced as well as implemented as an embodiment).

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices; electrical, optical, acoustical or other form of non-transitory signals; etc.; which do not encompass any transitory form of signal transmission.

As used in this description, "one embodiment" or "an embodiment" or similar phrases means that the feature(s) being described are included in at least one embodiment of the invention. References to "one embodiment" in this description do not necessarily refer to the same embodiment; however, neither are such embodiments mutually exclusive. Nor does "one embodiment" imply that there is but a single embodiment of the invention. For example, a feature, structure, act, etc. described in "one embodiment" may also be included in other embodiments. Thus, the invention may include a variety of combinations and/or integrations of the embodiments described herein.

While the invention has been described in terms of several embodiments, those of skill in the art will recognize that the invention is not limited to the embodiments described herein, but can be practiced with modification and alteration within the spirit and scope of the appended claims. The description is thus to be regarded as illustrative instead of limiting.

What is claimed:

1. An apparatus to obtain diagnostic cardiovascular data from a human comprising:
    means for acquiring vibrational cardiac data noninvasively from a surface of the human's body, proximal to the human's heart, at a plurality of locations simultaneously;
    means for identifying a band of frequency within the vibrational cardiac data that contains a feature; and
    means for processing the band of frequency to obtain a first three-dimensional spatial location for a source of a first energy maximum within the human's chest.

2. The apparatus of claim 1, further comprising:
    means for using physiological and clinical information derived from the feature to classify a type of vibration source that produced the feature.

3. The claim 1, further comprising:
    means for determining if the feature has a transient characteristic;

means for fusing other clinical test localization and classification data with the first three-dimensional spatial location; and means for assessing a quality of a classification for the feature based on a spectrally and spatially based estimate of source signal to background noise ratio (SNR) for the first three-dimensional spatial location.

4. The apparatus of claim 1, further comprising:

means for producing an assessment of a state of health of the human from independent a priori knowledge of valve and artery locations, echocardiographic test results, the first location, feature characteristics, and transient characteristics.

5. The apparatus of claim 1, further comprising:

means for producing an assessment of a state of health of the human from the first three-dimensional spatial location using power spectral density characteristics of the feature.

6. The apparatus of claim 1, further comprising:

means for reducing noise in the vibrational cardiac data.

7. The apparatus of claim 1, further comprising:

means for correlating the first three-dimensional spatial location with echocardiographic tests results and an ultrasound probe that has a thoracic field of view that is comparable with a field of view of the means for acquiring.

8. The apparatus of claim 1, wherein the means for identifying further comprising:

deselecting a portion of frequency from the band of frequency, wherein the portion contains an unwanted event.

9. The apparatus of claim 8, wherein the unwanted event is selected from the group consisting of general ambient noise, vibrational energy as a result of valve closure, respiratory system noise, digestive noise, and electromagnetic noise.

* * * * *